US008233633B2

(12) United States Patent
Kano

(10) Patent No.: US 8,233,633 B2
(45) Date of Patent: Jul. 31, 2012

(54) NOISE CONTROL DEVICE

(75) Inventor: Hiroyuki Kano, Hyogo (JP)

(73) Assignee: Panasonic Corporation, Osaka (JP)

(*) Notice: Subject to any disclaimer, the term of this patent is extended or adjusted under 35 U.S.C. 154(b) by 288 days.

(21) Appl. No.: 12/616,978

(22) Filed: Nov. 12, 2009

(65) Prior Publication Data

US 2010/0124341 A1 May 20, 2010

(30) Foreign Application Priority Data

Nov. 14, 2008 (JP) ................................ 2008-292246

(51) Int. Cl.
*A61F 11/06* (2006.01)
*H04B 15/00* (2006.01)

(52) U.S. Cl. .................... 381/71.8; 381/94.1; 381/94.3; 381/71.14; 381/71.11

(58) Field of Classification Search ................ 381/94.1, 381/94.3, 71.8, 71.14, 71.2, 71.1, 71.11
See application file for complete search history.

(56) References Cited

U.S. PATENT DOCUMENTS

2008/0310645 A1* 12/2008 Itabashi et al. .............. 381/71.6

FOREIGN PATENT DOCUMENTS

| | | |
|---|---|---|
| JP | 05-052645 | 3/1993 |
| JP | 05-067948 | 3/1993 |
| JP | 2000-347671 | 12/2000 |

OTHER PUBLICATIONS

P.A. Nelson and S.J. Elliott, "Active Control of Sound", Academic Press, pp. 176-178, 1992.

* cited by examiner

*Primary Examiner* — Devona Faulk
*Assistant Examiner* — George Monikang
(74) *Attorney, Agent, or Firm* — Wenderoth, Lind & Ponack, L.L.P.

(57) ABSTRACT

A noise control device includes a signal processor that detects a noise outputted from a noise source, and generates a control signal based on the noise and a control acoustic system that generates a control sound for canceling the noise, based on the control signal outputted from the signal processor. The noise control device also includes an output correction section that corrects the control signal outputted from the signal processor, in a frequency band for which a noise control process time τ, which is a time period from when the noise is outputted from the noise source to pass through the signal processor and the control acoustic system to when the control sound reaches the control point, is larger than a noise transfer time T, which is a time period from when the noise is outputted from the noise source to when the noise reaches the control point via the noise transfer system (τ>T).

7 Claims, 57 Drawing Sheets

NOISE CONTROL DEVICE

BACKGROUND OF THE INVENTION

1. Field of the Invention

The present invention relates to a noise control device, and more particularly to a noise control device which, even when a noise includes a frequency band for which a noise control process cannot be performed within a noise transfer time because of downsizing, cost reduction, and the like, reduces the noise in a frequency band for which the noise control process can be performed within the noise transfer time, while preventing an adverse effect in the frequency band for which the noise control process cannot be performed within the noise transfer time.

2. Description of the Background Art

There has been, for a long time, an idea of the so-called active noise control, in which a sound having the opposite phase to the phase of a noise outputted from a noise source is reproduced from a control speaker to thereby cancel the noise. Conventionally, a practical use of the active noise control using an analog feedback control (hereinafter referred to as a FB control) has been pursued, and these days, the analog FB control is generally used in a headphone and the like. FIG. 45 shows a fundamental configuration of a noise control device using the FB control.

When an analog FB control is used, costs can be suppressed to be relatively low. However, an analog FB control has a problem that it is difficult to realize complicated control characteristics, and moreover a problem that it is difficult to obtain a stable and excellent noise reduction effect because of an oscillation condition involved in the FB control. Even though there are the problems mentioned above, an analog FB control in a one-dimensional space, such as for a headphone, is an appropriate choice in consideration of cost performance, and in fact, there are a number of examples of the practical use thereof.

However, when the FB control using a digital control is performed in a three-dimensional space such as an automobile, a process for the FB control becomes more complicated than for a feed forward control (hereinafter referred to as an FF control), due to oscillation and the like. Accordingly, there are very few examples of a practical use in which the FB control is performed using the digital control. In addition, even in a one-dimensional control such as for a ventilation duct, a digital adaptive FF control is dominant, in consideration of a noise change and a secular change of control speaker characteristics, microphone characteristics, and the like. Therefore, the FF control will firstly be described.

FIG. 43 shows a fundamental configuration of the FF control.

A signal processor 300 processes a noise signal and generates a control signal, in time for a noise from a noise source 1 reaching a control point 4 via a noise transfer system 200. Then, at the control point 4, the signal processor 300 applies the control signal to the noise that reaches the control point 4 via the noise transfer system 200. As a result of a synthesis of the control signal and the noise at the control point 4, the noise is reduced. That is, the signal processor 300 may generate a control signal having the opposite characteristics (the same amplitude and the opposite phase) to the characteristics of the noise that reaches the control point 4 via the noise transfer system 200. In addition, as clear from FIG. 43, in the FF control, a noise transfer time T in the noise transfer system 200 and a processing time $\tau$ in the signal processor 300 have to satisfy the relationship of $\tau$=T. Here, when the FF control shown in FIG. 43 is realized using a digital process, the signal processor 300 is normally formed with a digital filter such as an FIR filter. Therefore, the process performed by the signal processor 300 inevitably becomes a time-delay process due to a digital delay. Accordingly, since a delay time can be finely adjusted by a coefficient of the FIR filter for example, a condition for the processing time in the signal processor 300 may be $\tau \leqq T$. Thus, a noise control process can be performed within a noise transfer time.

FIG. 43 is on the assumption that the noise transfer system 200 does not vary, but in fact, the noise transfer system 200 often varies. For example, in a case where the noise transfer system 200 is applied to an exhaust pipe or the like: an acoustic velocity changes depending on a temperature; and, in a noise of a running automobile, a noise (transfer characteristics) changes depending on a running state such as a road surface and a speed, or the number of passengers and positions of the passengers, and the like. In order to absorb these changes, an adaptive FF control is performed. FIG. 44 shows a fundamental configuration of a noise control device in a case where the adaptive FF control is used. As shown in FIG. 44, a result in the control point 4 is, as an error signal, returned to the signal processor 300, and the signal processor 300 changes control characteristics (a coefficient) of the signal processor 300, based on the error signal.

Here, when the adaptive FF control shown in FIG. 44 is used, a correlativity (coherence) between a reference signal (a signal a of FIG. 44), which is a noise signal outputted from the noise source 1, and the error signal (a signal b of FIG. 44) is important, for an accurate convergence of the control characteristics (a coefficient) of the signal processor 300. When the correlativity is low, an accurate coefficient cannot be obtained, and as a result, a sufficient noise reduction effect cannot be obtained (for example, Japanese Laid-Open Patent Publication No. 5-52645; and ACTIVE CONTROL OF SOUND, P. A. Nelson & S. J. Elliott, ACADEMIC PRESS, P177). Particularly, Japanese Laid-Open Patent Publication No. 5-52645 also mentions a multiple coherence in a case of a three-dimensional control, and shows that, in this case as well, the higher the coherence is, the larger the obtained noise reduction effect becomes.

From the above, it can be said that, in the adaptive FF control, conditions for obtaining the maximum noise reduction effect are that:

(1) the noise control process can be performed within the noise transfer time; and (2) the correlativity between the reference signal and the error signal is high.

In order that the noise control process can be performed within the noise transfer time, it is necessary that, in FIGS. 43 and 44, the processing time $\tau$ in the signal processor 300 is shorter than the noise transfer time T, which however cannot always be satisfied because of the problem of costs and the like. For example, as a method for shortening the processing time $\tau$ in the digital control, increasing a sampling frequency can be mentioned firstly. In this case, on the contrary, a problem occurs that a time usable for a signal process is shortened (because a time usable as the processing time is given as the inverse of the sampling frequency) and thus a sufficient amount of operations cannot be ensured, and the like. Consequently, it is necessary to reduce the total amount of operations such that the operations can be performed within the processing time by reducing the number of control filter taps in the signal processor 300 or, in a three-dimensional control, by reducing the number of noise processes (=the number of control filters). As a result, a noise reduction effect cannot be obtained in a low frequency range due to a lack of the number of taps, or an efficient noise reduction effect cannot be obtained because the multiple coherence is lowered due to a lack of the number of noise processes.

On the other hand, when the sampling frequency is lowered for ensuring the time for operations, the processing time $\tau$ in the signal processor 300 is increased, and it becomes necessary to increase the noise transfer time T by the amount of the increase of the processing time $\tau$ in order that the noise control process can be performed within the noise transfer time. This normally means increasing a length from the noise source 1 to the control point 4. As a result, a noise control system as a whole is increased in size, and a problem may occur that this noise control system cannot be applied to a small-size product such as headphones and vacuum cleaners. Moreover, actually, when the length from the noise source 1 to the control point 4 is increased, the correlativity between the reference signal and the error signal is often lowered. For example, in a case of a ventilation duct, a noise of a fan which is a noise source, and the like, transfers within the duct, and exhaust air as a fluid also passes together with the noise. Therefore, a turbulent flow or the like is generated in a region between the noise source 1 to the control point 4, to lower the correlativity. Thus, the longer the distance from the noise source 1 to the control point 4 is, the more likely the turbulent flow is to occur to lower the correlativity. In another example, in a noise of a running automobile, train, and the like, many noises, such as not only an engine noise and a motor noise but also a road noise, a wind noise, noises of surrounding vehicles, enter the inside of a vehicle. Therefore, it is difficult to ensure that, for all noises, noise signals as reference signals are detected at noise sources which are originating points of the noises. Consequently, the noise signal is detected in the middle of a noise transfer system. In such a case, as a point at which the noise signal is detected is nearer the control point 4, the correlativity between a reference signal and an error signal becomes higher. In other words, the longer the distance from the noise source 1 to the control point 4 is, the lower the correlativity becomes.

In this manner, in a normal noise environment, shortening a time for the noise control process and increasing the correlativity between the reference signal and the error signal are incompatible with each other. Therefore, conventionally, they are balanced with each other, for the practical use.

Here, an influence in a case where the noise control process cannot be performed within the noise transfer time will be described in more detail.

FIG. 46 shows a control coefficient and a noise reduction effect in a case where the signal processor 300 shown in FIG. 43 or FIG. 44 can perform the noise control process within the noise transfer time. In FIG. 46: (1) shows impulse characteristics of the control coefficient (when an FIR filter having 2048 taps is used, for example) of the signal processor 300; (2) shows, in its upper section, noise characteristics before a control (control "OFF") and noise characteristics after the control (control "ON"); and (2) shows, in its lower section, control OFF-ON difference characteristics, that is, the amount of the noise reduction effect. In FIG. 46, since the noise control process can be performed within the noise transfer time; in the control coefficient, a peak of an impulse is expressed in a good manner within coefficient taps, and also the noise reduction effect of approximately 60 dB can be obtained for all the frequencies.

On the other hand, FIG. 47 shows a control coefficient and a noise reduction effect in a case where the signal processor 300 shown in FIG. 43 or FIG. 44 cannot perform the noise control process within the noise transfer time. In impulse characteristics shown in (1), a peak of an impulse is not placed within coefficient taps but is beyond the 0th tap. That is, the fact that the noise control process cannot be performed within the noise transfer time is expressed as the control coefficient. Moreover, in the noise reduction effect of (2), a noise is not reduced at all for all the frequencies. In this manner, in the case where the noise control process cannot be performed within the noise transfer time, a problem occurs that the noise reduction effect cannot be obtained. Here, FIG. 47 shows a condition in a case where the noise control process cannot be performed within the noise transfer time for all the frequencies. However, actually, the noise control process often cannot be performed within the noise transfer time only for a certain frequency band. This will be indicated below.

FIG. 48 is a re-description of FIG. 43, showing a configuration similar to an actual example in which an analog is mixed. In FIG. 48, an AD (analog-digital) converter 5, a DA (digital-analog) converter 6, analog LPFs (low pass filters) 7 and 8 for anti-aliasing are added before and after the signal processor 300. Here, when a delay (the same value in all the frequencies) of the AD converter 5 is defined as $\tau 1$, a delay (the same value in all the frequencies) of the DA converter 6 is defined as $\tau 2$, and each of delays (maximum group delays) of the LPFs 7 and 8 is defined as $\tau 3$, $$\tau+\tau 1+\tau 2+2\times\tau 3\leqq T$$

has to be satisfied in order to perform the noise control process within the noise transfer time. Here, FIG. 49 shows characteristics of the analog LPF of FIG. 48. When the LPFs 7 and 8 have the characteristics shown in FIG. 49, the maximum group delay $\tau 3$ is equal to or greater than 30 samples around 10 kHz (30/48000=0.625 msec, when a sampling frequency is 48 kHz). Since each of the values of $\tau$, $\tau 1$, and $\tau 2$ is the same in all the frequencies, the point of the control is whether or not the noise control process can be performed within the noise transfer time at a frequency of around 10 kHz which corresponds to the maximum group delay $\tau 3$ of the LPFs 7 and 8.

FIG. 50 shows (1) a control coefficient and (2) a noise reduction effect in a case where the noise control process cannot be performed within the noise transfer time in FIG. 49. As seen from FIG. 50(2), the amount of reduced noise is 20 to 30 dB in a low frequency range, but the effect deteriorates in a higher range, and conversely the noise increases at a frequency around 10 kHz which corresponds to the maximum group delay $\tau 3$ of the LPFs 7 and 8. Also in FIG. 50(1), a peak of impulse characteristics of the coefficient is not placed within coefficient taps.

For reference, FIG. 51 shows (1) a control coefficient and (2) a noise reduction effect in a case where the noise control process can be performed within the noise transfer time in FIG. 49. Referring to the noise reduction effect in FIG. 51(2), the amount of reduced noise becomes small at a frequency equal to or higher than 10 kHz, but unlike FIG. 50(2), the noise does not increase. Also, in the control coefficient in FIG. 51(1), a peak of impulse characteristics of the coefficient is placed within coefficient taps, and the noise control process can be performed within the noise transfer time. In FIG. 51(2), the amount of reduced noise becomes small at a frequency equal to or higher than 10 kHz, and this is because the level of the LPFs 7 and 8 is drastically lowered as shown in FIG. 49(1). Since the signal processor 300 receives an influence thereof, the amount of reduced noise becomes small at a frequency equal to or higher than 10 kHz. If the noise control process can be performed within the noise transfer time, the noise is not increased but can be reduced.

In the above, the decrease of the amount of reduced noise and the noise increase in a high frequency range, due to the influence of a time for the noise control process, have been described. However, in a low frequency range as well, a decrease of the amount of reduced noise and a noise increase may occur. In a low frequency range, a main factor of a delay of the noise control process is a group delay of a control speaker. FIG. 52 shows characteristics of a general speaker. A resonant frequency fo of the speaker is approximately 150 Hz. Referring to group delay characteristics of FIG. 52(3), the speaker exhibits a group delay of 2 msec at the resonant frequency fo. The speaker exhibits a larger group delay at a frequency equal to or lower than the resonant frequency fo, but exhibits a smaller group delay at a frequency equal to or higher than the resonant frequency fo.

Similarly to the description of the amount of reduced noise and the noise increase in a high frequency range, the amount of reduced noise and a noise increase in a low frequency range will be described, by using a HPF (high pass filter) to realize the speaker characteristics. FIG. 53 is a diagram showing HPFs being additionally inserted to an output of the signal processor shown in FIG. 43. FIG. 54 shows amplitude characteristics and group delay characteristics of first-order HPFs 9 and 10 shown in FIG. 53. Here, in FIG. 52(1), a level of the speaker in a low frequency range drops at −12 dB/oct. Therefore, by using two first-order HPFs having the same cutoff frequency fc=150 Hz and the same cutoff characteristics of −6 dB/oct., the characteristics shown in FIG. 52 are approximated. As shown in FIG. 54(2), a group delay of each of the first-order HPFs 9 and 10 at 150 Hz is 25 samples (25/48000=0.521 msec). Accordingly, a group delay obtained by using the two first-order HPFs 9 and 10 is approximately 1 msec. The group delay of the first-order HPFs 9 and 10 of FIG. 54 is smaller than the group delay of the speaker of FIG. 52. However, in a case where the noise control process cannot be performed within the noise transfer time, the noise reduction effect deteriorates in a lower range, and the noise increases at a frequency equal to or lower than 100 Hz, as shown in FIG. 55(2). That is, the same situation as the deterioration of the noise reduction effect and the noise increase in a high frequency range occurs in a low frequency range, too, due to the group delay of the speaker. For reference, FIG. 56 shows (1) a control coefficient and (2) a noise reduction effect in a case where the noise control process can be performed within the noise transfer time in FIG. 53. Referring to the noise reduction effect in FIG. 56(2), similarly to in a high frequency range, the amount of reduced noise becomes smaller in a lower range, but unlike in FIG. 55(2), the noise does not increase, if the noise control process can be performed within the noise transfer time.

As above, it can be understood that the noise reduction effect can be obtained in a frequency band for which a group delay is small and the noise control process can be performed within the noise transfer time, but if there is a frequency band for which a group delay is large and the noise control process cannot be performed within the noise transfer time, a noise increase occurs in the frequency band.

A phenomenon that, while the noise reduction effect can be obtained in a certain frequency band, a noise increase occurs in another frequency band, and the like, is a problem often faced when the noise control is practically used, such as the above-described problem of the group delay. A method for preventing such a disadvantage in a certain frequency band has been conventionally proposed (for example, Japanese Laid-Open Patent Publication No. 5-67948). This method tries to prevent occurrence of a problem by suppressing, in an adaptive filter that performs the noise control, an increase of a coefficient gain for a frequency band in which the problem occurs (a noise increases).

In the following, a conventional method will be described. FIG. 57 shows a fundamental configuration disclosed in Japanese Laid-Open Patent Publication No. 5-67948. In a noise control device shown in FIG. 57, there is a noise source 101 in a casing 102 having an opening at one end thereof. From the noise source 101 toward the opening, a noise detection microphone 103, a sound cancellation speaker 105, and a sound cancellation error detection microphone 104 are placed in this order. In the noise control device shown in FIG. 57, a control circuit using an adaptive digital filter is provided. The adaptive digital filter is formed with a main adaptive digital filter portion and an auxiliary adaptive digital filter portion. The main adaptive digital filter portion is formed with an FIR digital filter 106 and a coefficient controller 108 that is controlled based on an LMS (Least-Mean-Square) algorithm. The auxiliary adaptive digital filter portion is formed with a FIR digital filter 110 and a coefficient controller 111 that is controlled based on the LMS algorithm. The two FIR digital filters 106 and 110 share a coefficient sequence ha(i). Moreover, a filter 109 is connected to a signal input section of the FIR digital filter 110, and a digital filter 107 is connected to the coefficient controller 108.

In the noise control device, a noise detected by the noise detection microphone 103 is converted into a digital signal by an A/D converter 115 via a preamplifier 112, and a noise signal u(n) is generated. Then, the noise signal u(n) is inputted to the digital filters 107 and 109, and the FIR digital filter 106. In the FIR digital filter 106, a control coefficient is calculated based on the predetermined coefficient sequence ha(i), and a noise cancellation signal y(n) is generated. The noise cancellation signal y(n) is converted into an analog signal by a D/A converter 116, and inputted to the sound cancellation speaker 105 via a power amplifier 113. Then, a sound wave outputted from the noise source 101 and a sound wave outputted from the sound cancellation speaker 105 interfere with each other, and thereby the noise outputted from the noise source 101 is canceled. A result of the sound cancellation is detected by the sound cancellation error detection microphone 104, outputted as an error signal e0(*n*) via a preamplifier 114 and an A/D converter 117, and inputted to the coefficient controller 108. In the coefficient controller 108, the coefficient sequence ha(i) is updated and controlled so as to minimize the inputted error signal e0(*n*). Here, the digital filter 107 is inserted for correcting the noise signal u(n) to thereby control the coefficient with an increased accuracy.

On the other hand, in the digital filter 109, the noise signal u(n) is inputted and an output signal u1(*n*) is outputted. Here, the digital filter 109 has high-pass-type frequency characteristics which cause the noise cancellation signal y(n) to have a frequency-characteristics restriction for not outputting an uncontrollable high-frequency sound. The output signal u1(*n*) outputted from the digital filter 109 is inputted to the FIR digital filter 110. In the FIR digital filter 110, a control coefficient is calculated based on the predetermined coefficient sequence ha(i), and an error signal e1(*n*) is generated. The coefficient controller 111 updates the coefficient sequence ha(i), based on the output signal u1(*n*) outputted from the digital filter 109 and the error signal e1(*n*). In other words, the coefficient sequence ha(i) is updated and controlled in such a manner that when a high-frequency signal passing through the digital filter 109 is inputted to the FIR digital filter 110, the signal is made zero.

In this manner, in the noise control device shown in FIG. 57, the high-frequency signal which is disturbing is cut off, and a sound cancellation control by the adaptive digital filter is performed in a frequency band that allows a stable adaptive operation control.

The noise control device shown in FIG. 57 tries to prevent an occurrence of the problem by suppressing an increase of a coefficient gain for a frequency band in which the problem occurs (a noise increases), by using an adaptive filter that performs a noise control. However, the noise control device shown in FIG. 57 is on the assumption that the noise control process can be performed within the noise transfer time. Therefore, as described with reference to FIGS. 43 to 56, if there is a frequency band for which the noise control process cannot be performed within the noise transfer time, an occurrence of a noise increase in the frequency band cannot be prevented.

In addition, when a configuration and conditions (such as a sampling frequency and the number of taps) of the noise control device are determined, a processing time required by the whole of the device is determined. However, in the conventional method, the only method for performing the noise control process within the noise transfer time in the total processing time (for example, the time τ in FIG. 43) is to increase the length from the noise source to the control point (for example, to increase the noise transfer time T of the noise transfer system of FIG. 43). In this case, as described above, a noise control system as a whole is enlarged, to cause a problem that the size of a product is increased, that a practical use is impossible because a product having an assumed size cannot be obtained, or the like. Moreover, a distance from the noise source to the control point becomes long. Therefore, in a case of FIG. 44 for example, the correlativity between the reference signal a and the error signal b of the signal processor 300 is lowered, and the coefficient of the signal processor 300 cannot be accurately obtained. This causes a problem that a desired noise reduction effect cannot be obtained.

SUMMARY OF THE INVENTION

Therefore, an object of the present invention is to provide a noise control device capable of reducing a noise in a frequency band for which a noise control process can be performed within a noise transfer time while suppressing a noise increase in a frequency band for which the noise control process cannot be performed within the noise transfer time.

The present invention is directed to a noise control device for solving the above-described problems. A noise control device according to the present invention is a noise control device that transmits a noise outputted from a noise source via a noise transfer system and synthesizes the transmitted noise and a control sound at a control point to thereby reduce the noise. The noise control device includes: a signal processor that detects the noise outputted from the noise source, and generates a control signal based on the noise; a control acoustic system that generates the control sound for canceling the noise, based on the control signal outputted from the signal processor; and an output correction section that corrects the control signal outputted from the signal processor, in a frequency band for which a noise control process time τ, which is a time period from when the noise is outputted from the noise source to pass through the signal processor and the control acoustic system to when the control sound reaches the control point, is larger than a noise transfer time T, which is a time period from when the noise is outputted from the noise source to when the noise reaches the control point via the noise transfer system (τ>T).

A preferable output correction section corrects the control signal outputted from the signal processor such that noise transfer characteristics of the noise that reach the control point via the noise transfer system and noise control transfer characteristics of the control sound outputted from the control acoustic system have the same amplitude and opposite phases.

Moreover, a preferable output correction section includes: an adder to which the control signal outputted from the signal processor is inputted; a filter circuit that extracts a signal in the frequency band, from a signal outputted from the adder; and a gain adjuster that adjusts a level of the signal extracted by the filter circuit. The adder: adds the signal of which the level is adjusted by the gain adjuster, to the control signal which is outputted from the signal processor and inputted to the adder; and outputs the control signal thus corrected to the control acoustic system.

Furthermore, it is preferable that the adder, the filter circuit, and the gain adjuster form one feedback system, and that the output correction section includes a plurality of the feedback systems, and the plurality of the feedback systems are connected in series.

Furthermore, it is preferable that a signal obtained by synthesizing, at the control point, the noise transmitted via the noise transfer system and the control sound outputted from the control acoustic system is inputted to the signal processor, as an error signal, and that the signal processor: detects the noise outputted from the noise source, and uses the detected noise as a reference signal; and generates the control signal based on the reference signal and the error signal, such that a level of the error signal is minimized.

Furthermore, a noise control device according to the present invention is a noise control device that transmits a noise outputted from a noise source via a noise transfer system and synthesizes the transmitted noise and a control sound at a control point to thereby reduce the noise. The noise control device includes: a FIR (Finite Impulse Response) filter that detects the noise outputted from the noise source, and generates a control signal based on the noise; and a control acoustic system that generates the control sound for canceling the noise, based on the control signal outputted from the FIR filter. The FIR filter corrects the control signal such that noise transfer characteristics of the noise that reach the control point via the noise transfer system and noise control transfer characteristics of the control sound outputted from the control acoustic system have the same amplitude and opposite phases, in a frequency band for which a noise control process time τ, which is a time period from when the noise is outputted from the noise source to pass through the signal processor and the control acoustic system to when the control sound reaches the control point, is larger than a noise transfer time T, which is a time period from when the noise is outputted from the noise source to when the noise reaches the control point via the noise transfer system (τ>T). That is, the FIR filter has characteristics that approximate to the characteristics obtained by synthesizing the signal processor and the output correction section described above.

As described above, according to the present invention, a noise control device capable of reducing a noise in a frequency band for which a noise control process can be performed within a noise transfer time while suppressing a noise increase in a frequency band for which the noise control process cannot be performed within the noise transfer time, can be realized.

The noise control device according to the present invention can reduce a noise in a frequency band for which a noise control process can be performed within a noise transfer time while suppressing a noise increase in a frequency band for which the noise control process cannot be performed within the noise transfer time. The noise control device according to the present invention is widely applied in all fields that require a noise reduction, such as home appliances including vacuum cleaners, refrigerators, and air conditioners, transportation facilities including automobiles and aircrafts, and industrial equipments for use in factories and the like.

These and other objects, features, aspects and advantages of the present invention will become more apparent from the following detailed description of the present invention when taken in conjunction with the accompanying drawings.

DESCRIPTION OF THE PREFERRED EMBODIMENTS

Hereinafter, embodiments of the present invention will be described with reference to FIGS. 1 to 42.

First Embodiment

Figure 1:
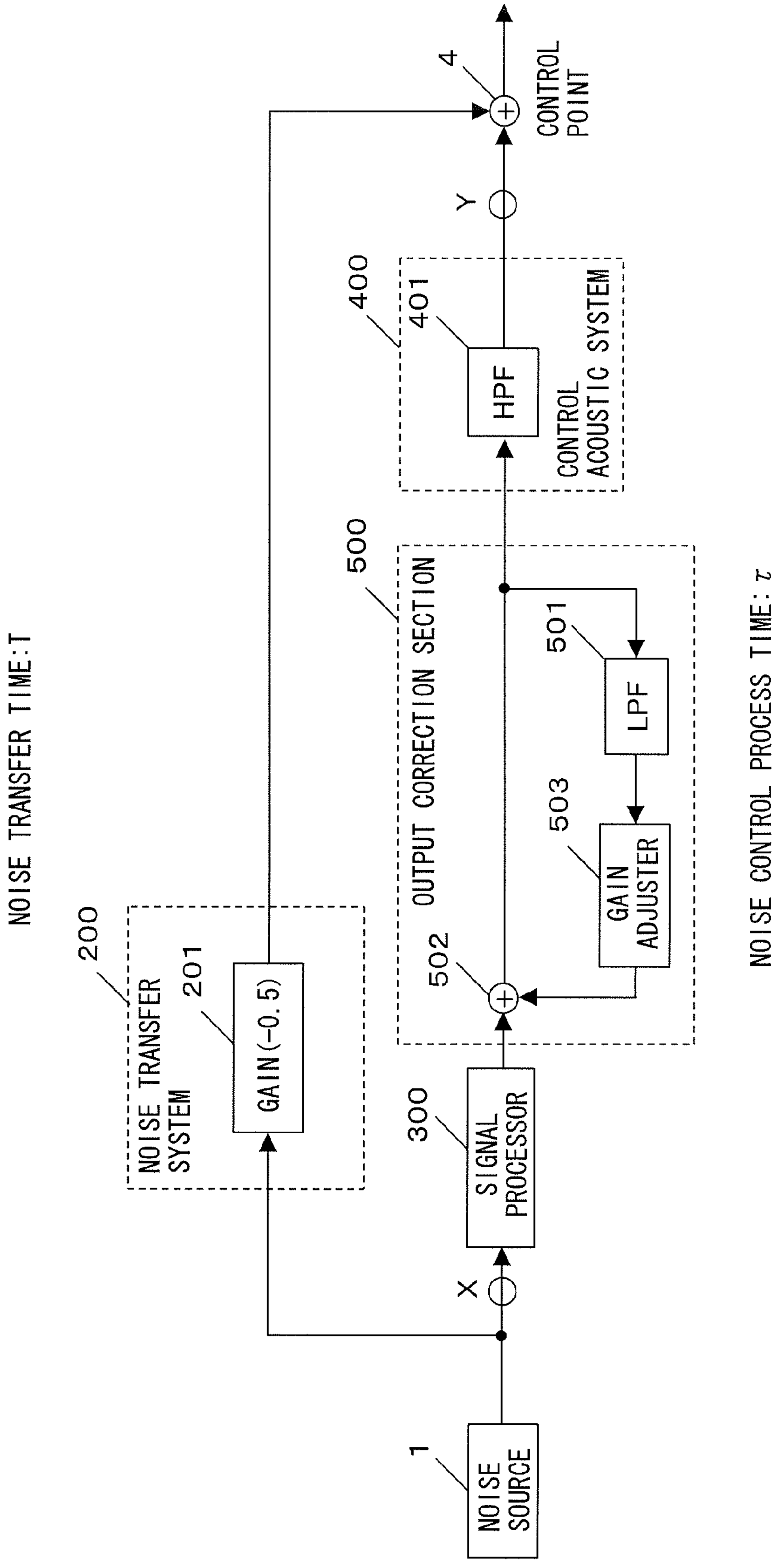
FIG. 1 shows a circuit configuration of a noise control device according to a first embodiment.
Figure 2:
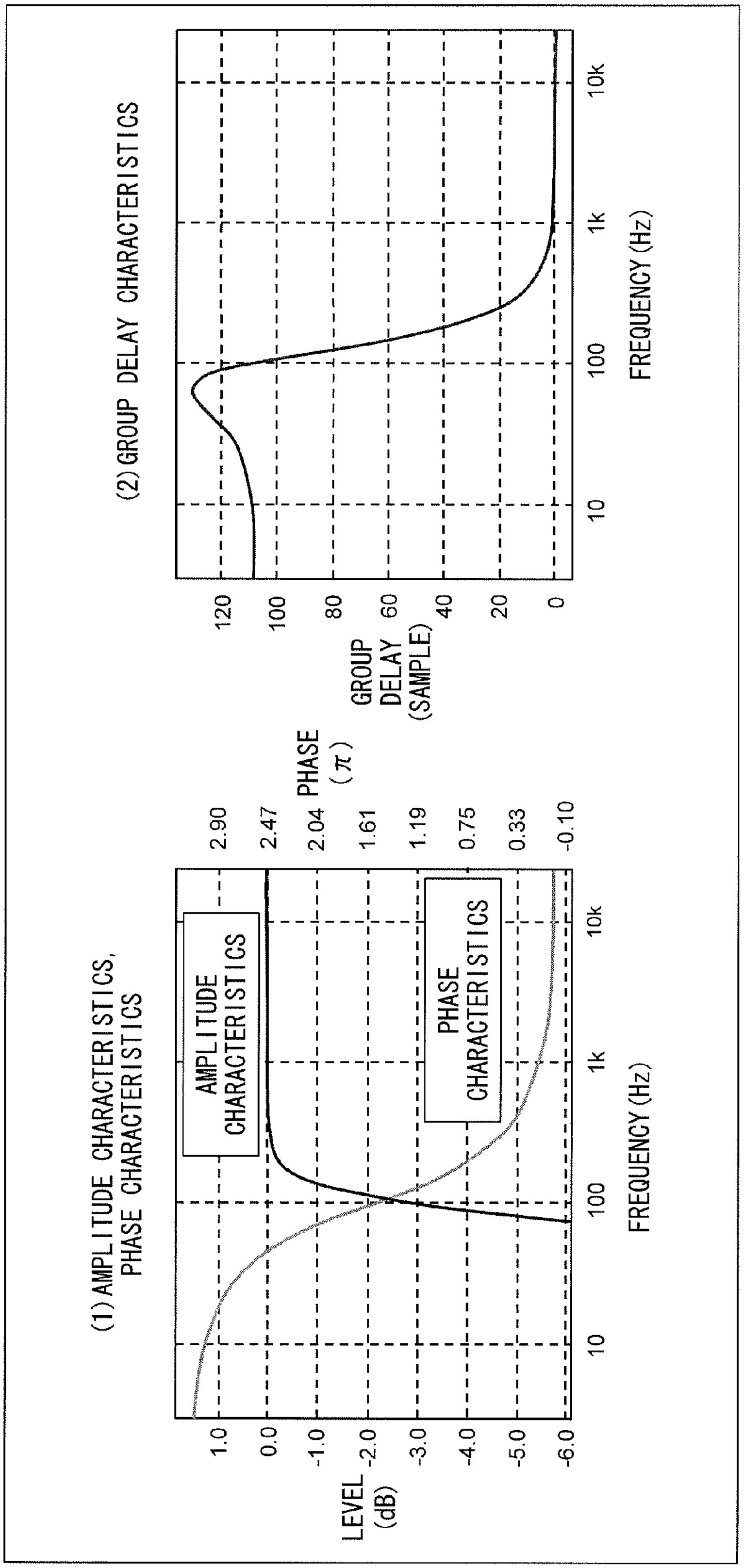
FIG. 2 shows characteristics of a HPF 401 of a control acoustic system 400 shown in FIG. 1.

A configuration of a noise control device according to a first embodiment of the present invention will be described. FIG. 1 shows a circuit configuration of the noise control device according to the first embodiment.

In FIG. 1, a noise signal outputted from a noise source 1 reaches a control point 4 via a noise transfer system 200. At the same time, a signal processor 300 processes the noise signal outputted from the noise source 1, and an output correction section 500 processes the signal that has been processed by the signal processor 300. Then, the signal processed by the output correction section 500 reaches the control point 4 via a control acoustic system 400, and is added to the noise signal outputted from the noise transfer system 200. A time period from when a noise is outputted from the noise source 1 to when the noise reaches the control point 4 via the noise transfer system 200 is defined as a noise transfer time T, and a time period from when a noise is outputted from the noise source 1 to pass through the signal processor 300 and the control acoustic system 400 to when a control sound reaches the control point 4 is defined as a noise control process time T. Here, a gain 201 having a value of −0.5 is set in the noise transfer system 200, and a HPF 401 is set in the control acoustic system 400. The HPF 401 is a second-order HPF having characteristics shown in FIG. 2 and having a resonant frequency fc=100 Hz.

Figure 3:
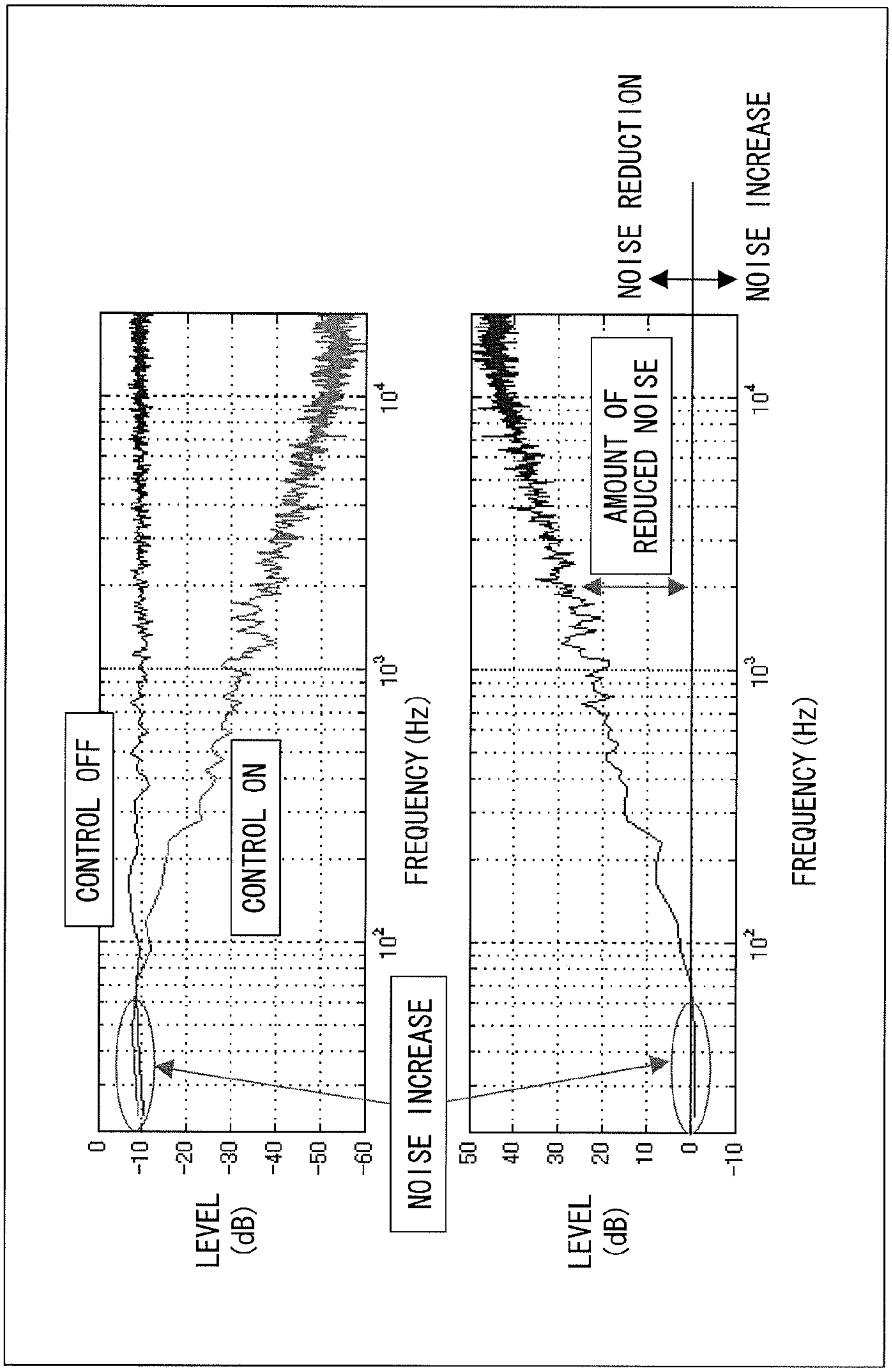
FIG. 3 shows a noise reduction effect at a control point 4 in a case where an output correction section 500 shown in FIG. 1 is not operated.

Firstly, the output correction section 500 is not operated, and a signal processed by the signal processor 300 is, without any change, inputted to the HPF 401 of the control acoustic system 400. The characteristics of the signal processor 300 are set such that, in a state where the output correction section 500 is not operated, a noise signal reaching the control point 4 via the noise transfer system 200 can be reduced. Here, since the noise transfer system 200 is formed with only the gain 201, a delay of the noise transfer system 200 is zero. On the other hand, in the control acoustic system 400, there is a group delay of the HPF 401 having the characteristics shown in FIG. 2, and therefore a noise control process cannot be performed within the noise transfer time in a low frequency range in which the group delay is large. Accordingly, in a control effect at the control point 4, the lower the frequency is, the smaller the noise reduction effect becomes, and a noise increases, though a little, at a frequency equal to or lower than 60 Hz, as shown in FIG. 3.

Figure 4:
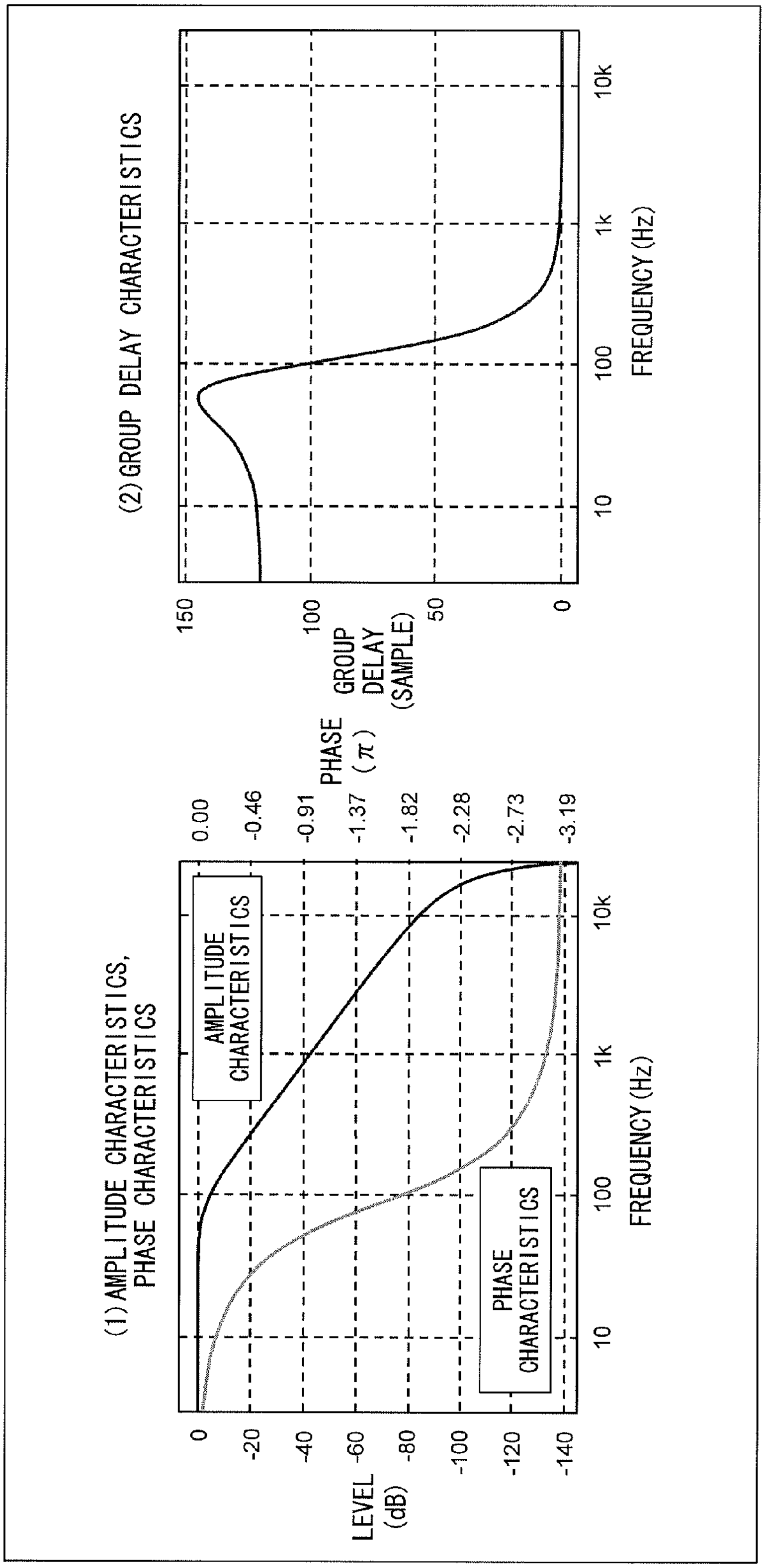
FIG. 4 shows characteristics of a LPF 501 of the output correction section 500 shown in FIG. 1.
Figure 5:
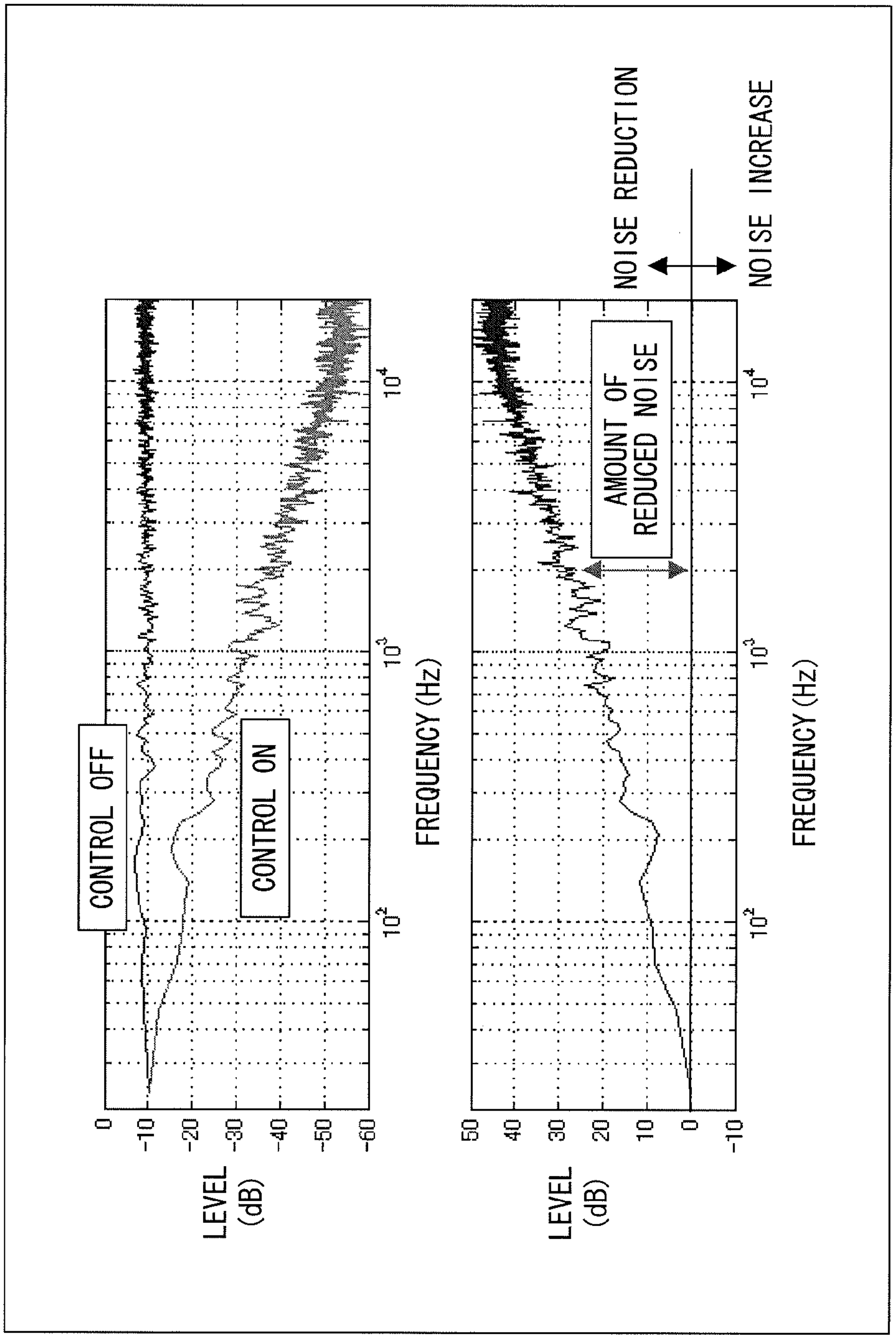
FIG. 5 shows a noise reduction effect at the control point 4 in a case where the output correction section 500 (the characteristics of FIG. 4) shown in FIG. 1 is operated.

Next, a second-order LPF shown in FIG. 4 having a resonant frequency fc=90 Hz is applied to the LPF 501, and a gain adjuster 503 appropriately adjusts the level of an output signal outputted from the LPF 501. The signal of which the level is adjusted by the gain adjuster 503 is inputted to an adder 502, and fed back. In this manner, the output correction section 500 forms an FB. Here, the FB formed in the output correction section 500 becomes a negative feedback when a negative value such as −1.0 is set in the gain adjuster 503, and becomes a positive feedback when a positive value such as +1.0 is set in the gain adjuster 503. When the output correction section 500 is operated to perform a positive feedback, an effect shown in FIG. 5 is obtained. Referring to FIG. 5, the noise increase at 60 Hz in FIG. 3 is prevented, and in addition the noise is reduced. Moreover, the noise reduction effect at a frequency equal to or lower than 200 Hz is improved.

The reason for this will be described below.

Figure 6:
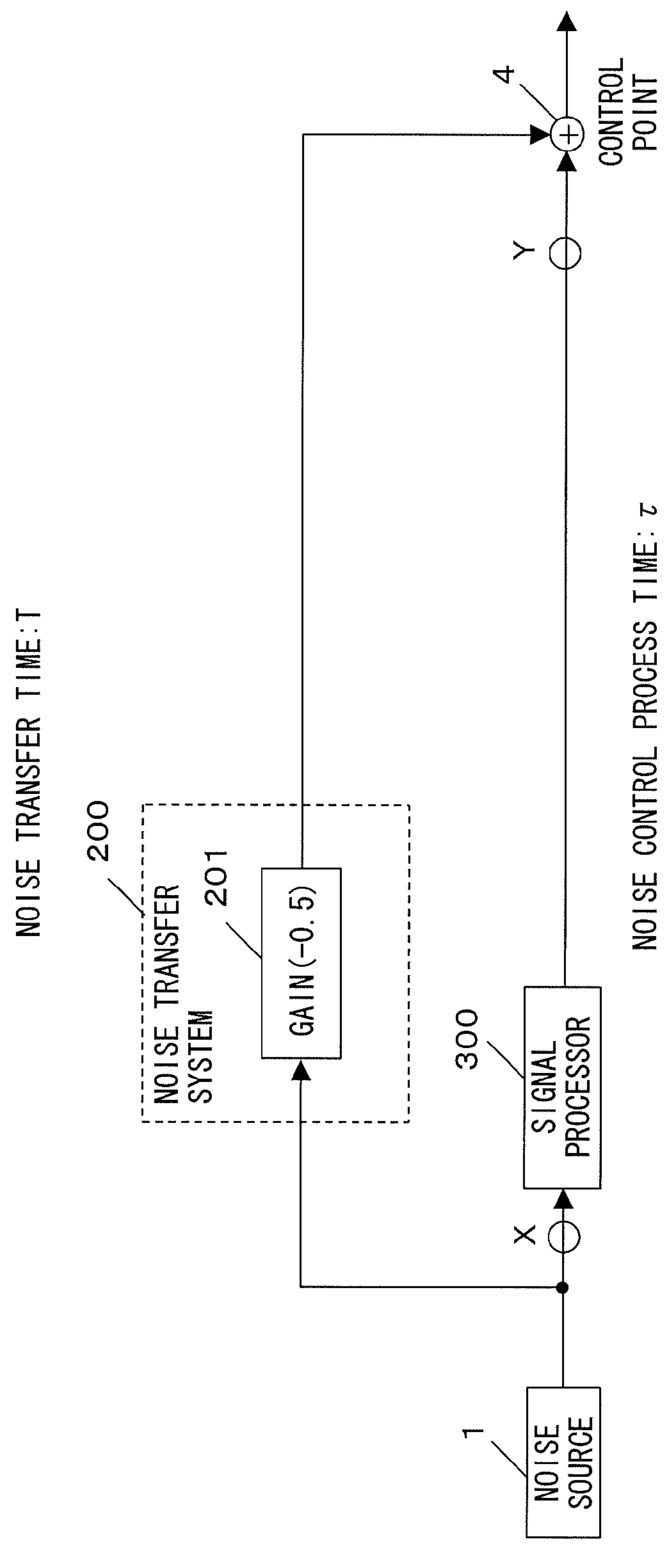
FIG. 6 shows a noise control device in which the output correction section 500 and the control acoustic system 400 shown in FIG. 1 are not provided.
Figure 7:
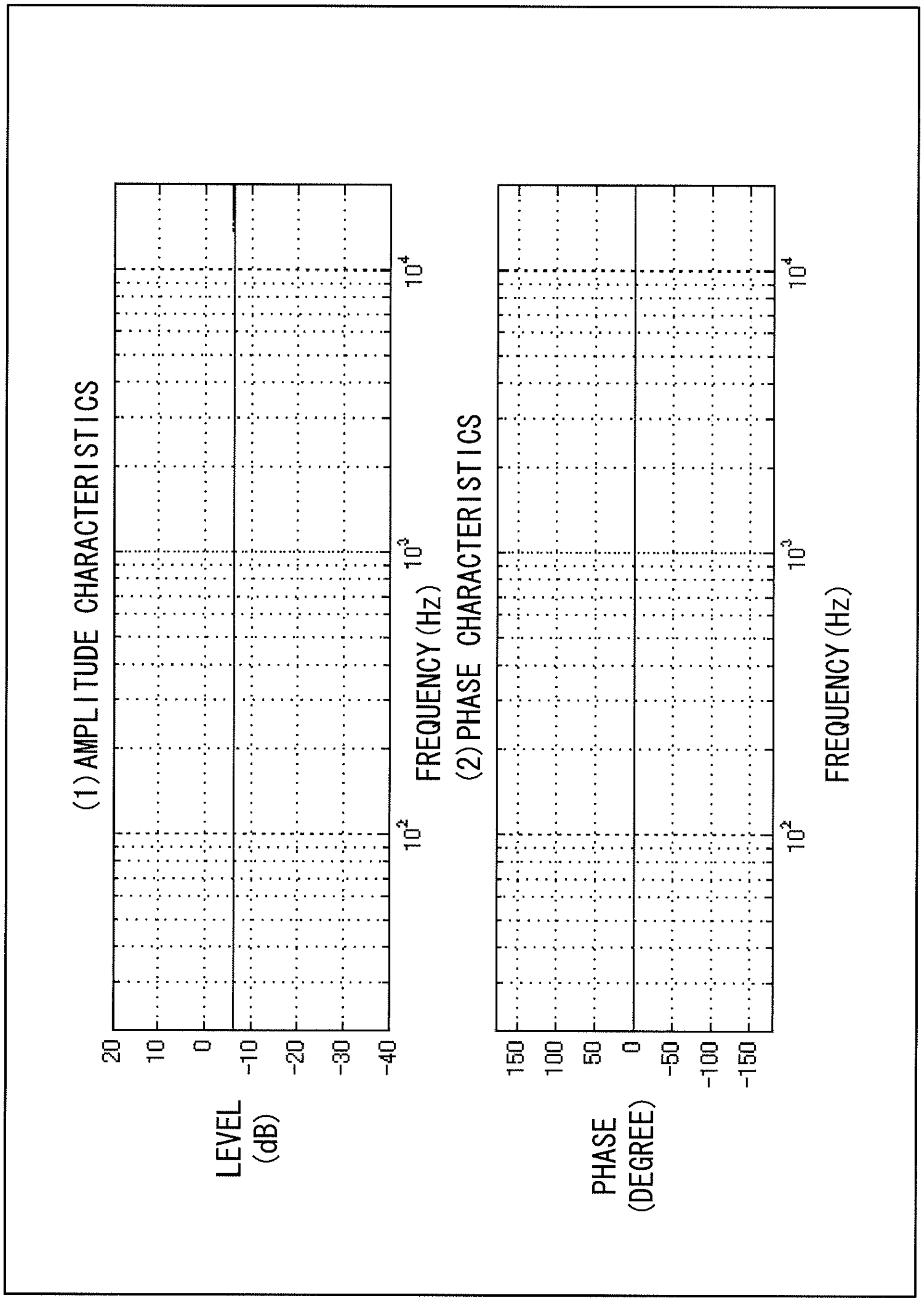
FIG. 7 shows transfer characteristics for transfer from a point X to a point Y of the noise control device shown in FIG. 6.

FIG. 6 shows a noise control device in which the output correction section 500 and the control acoustic system 400 of the noise control device shown in FIG. 1 are not provided. In FIG. 6, since a delay of the signal processor 300 and a delay of the noise transfer system 200 are the same, the noise control process can be performed within the noise transfer time. Characteristics of the signal processor 300 are the same as transfer characteristics for transfer from a point X to a point Y, and are as shown in FIG. 7. As clear from FIG. 7, the transfer characteristics for transfer from the point X to the point Y have the same amplitude as and the opposite phase to (that is, gain characteristics of +0.5) those of the transfer characteristics of the noise transfer system 200.

Figure 8:
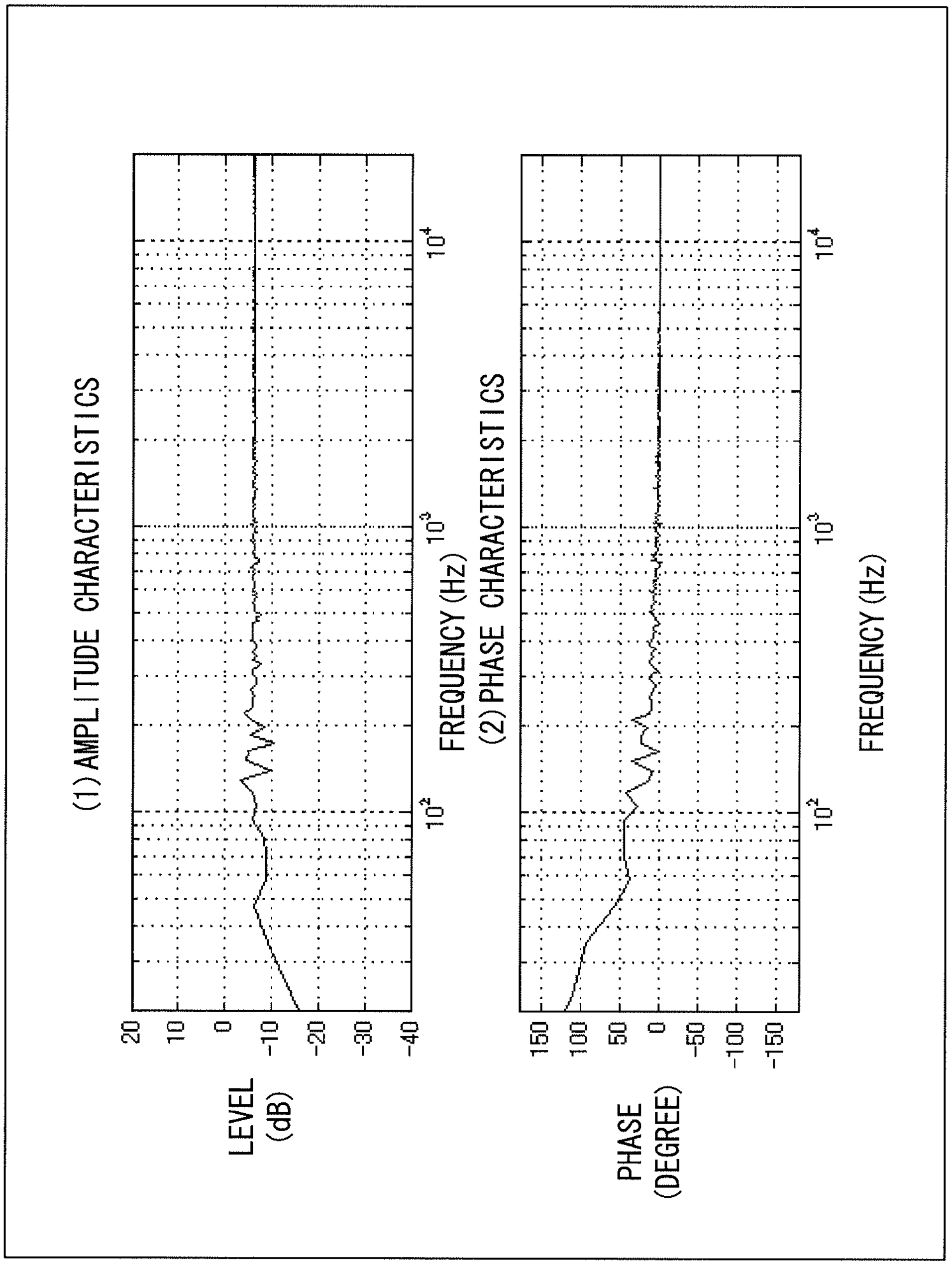
FIG. 8 shows transfer characteristics for transfer from the point X to the point Y in a case where the output correction section 500 shown in FIG. 1 is not operated.
Figure 9:
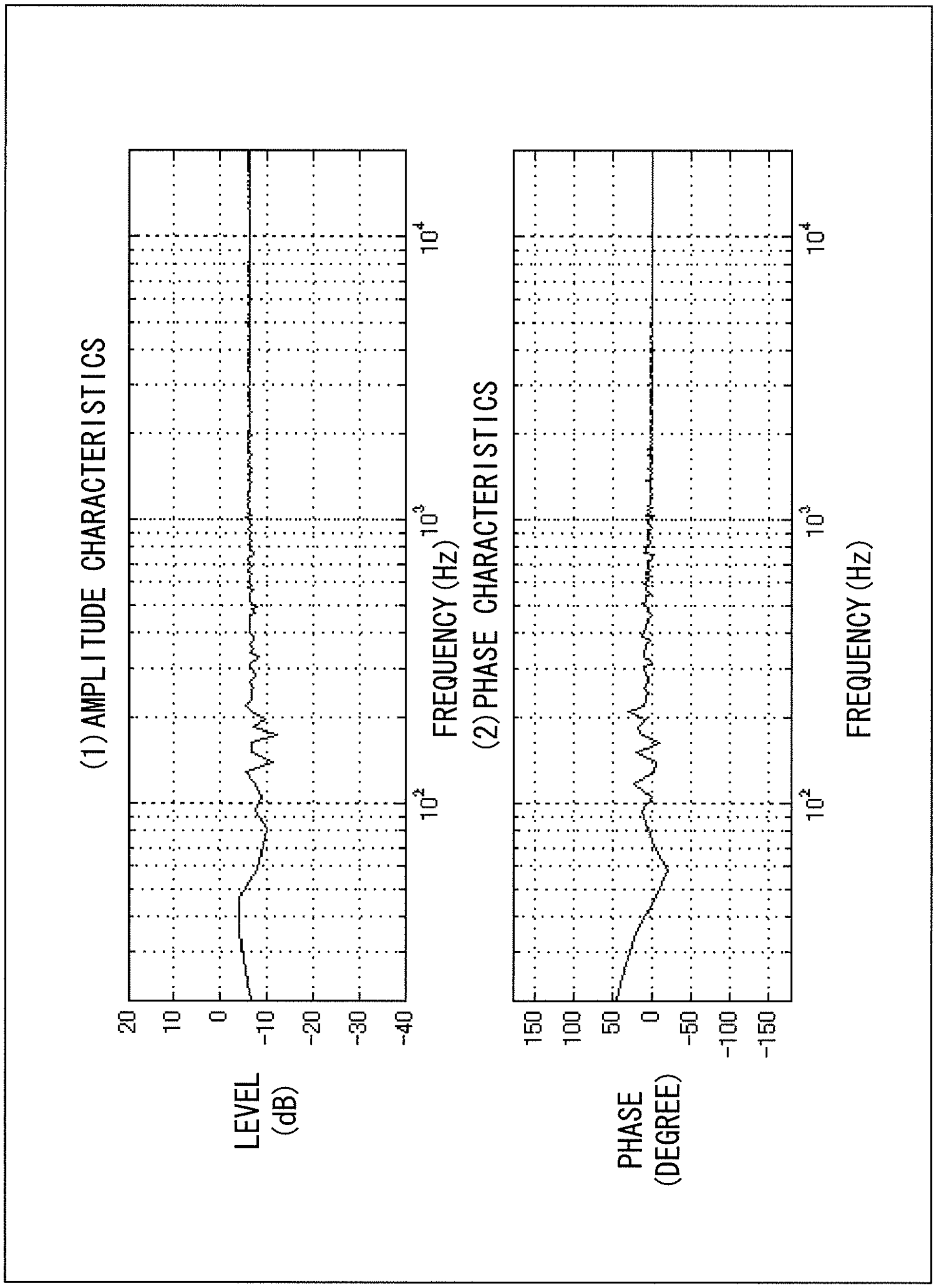
FIG. 9 shows transfer characteristics for transfer from the point X to the point Y in a case where the output correction section 500 (the characteristics of FIG. 4) shown in FIG. 1 is operated.

FIG. 8 shows transfer characteristics for transfer from the point X to the point Y in a case where the output correction section 500 of the noise control device shown in FIG. 1 is not operated (=the effect shown in FIG. 3). On the other hand, FIG. 9 shows transfer characteristics for transfer from the point X to the point Y in a case where the output correction section 500 of the noise control device shown in FIG. 1 is operated (=the effect shown in FIG. 5). In FIG. 8(1), the amplitude is reduced in a low frequency range equal to or lower than 40 Hz. In FIG. 8(2), the phase is shifted from zero degrees in a low frequency range equal to or lower than 200 Hz. In contrast, in FIG. 9(1), the amplitude is generally −6 dB, and in FIG. 9(2), the phase is maintained at or near zero degrees even in a low frequency range. In this manner, the characteristics shown in FIG. 9 are close to the characteristics shown in FIG. 7. That is, even if there is a low frequency range for which the noise control process cannot be performed within the noise transfer time due to the group delay of the HPF 401 of the noise control device shown in FIG. 1, the noise control device shown in FIG. 1 operates the output correction section 500 to thereby perform a process that is close to the control performed by the noise control device shown in FIG. 6 in which the noise control process can be performed within the noise transfer time.

Figure 10:
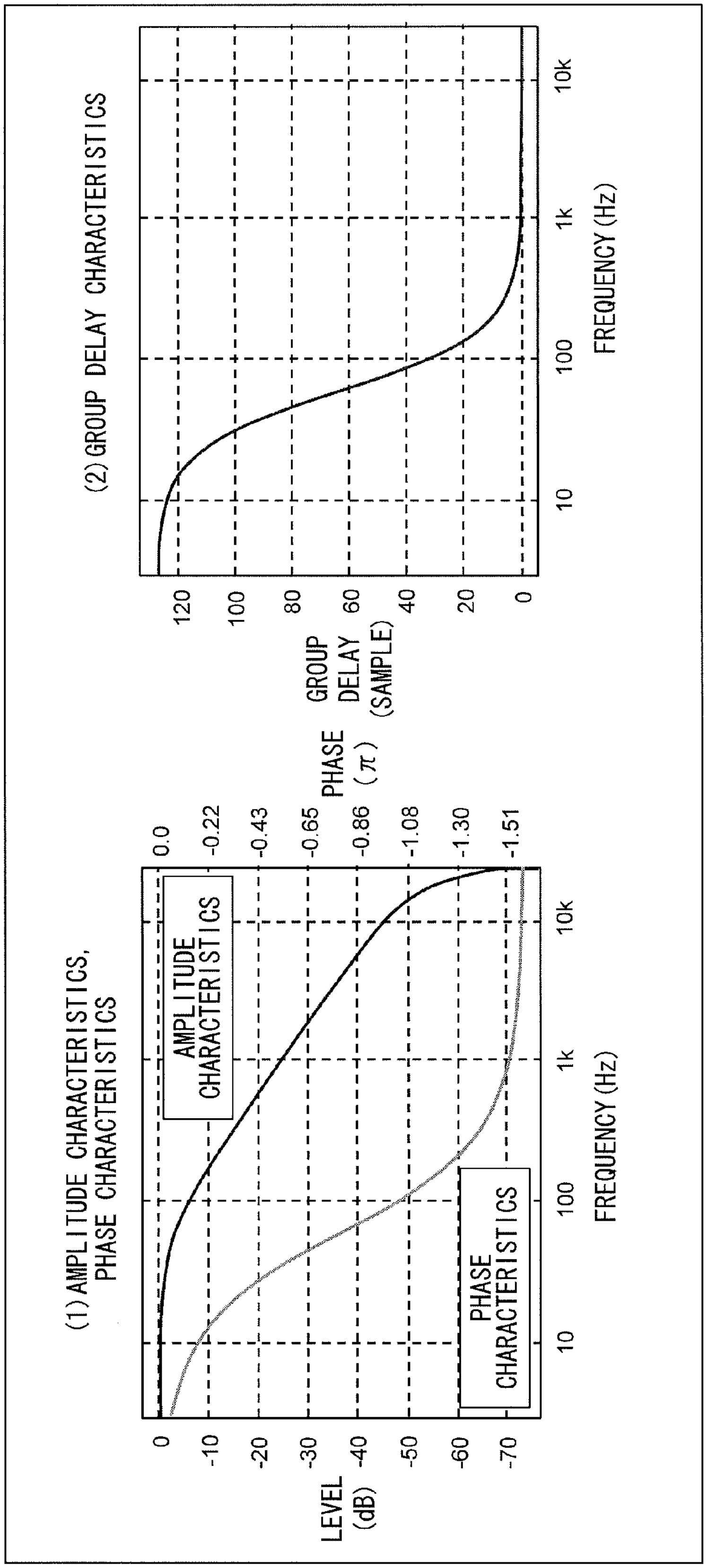
FIG. 10 shows other characteristics of the LPF 501 of the output correction section 500 shown in FIG. 1.
Figure 11:
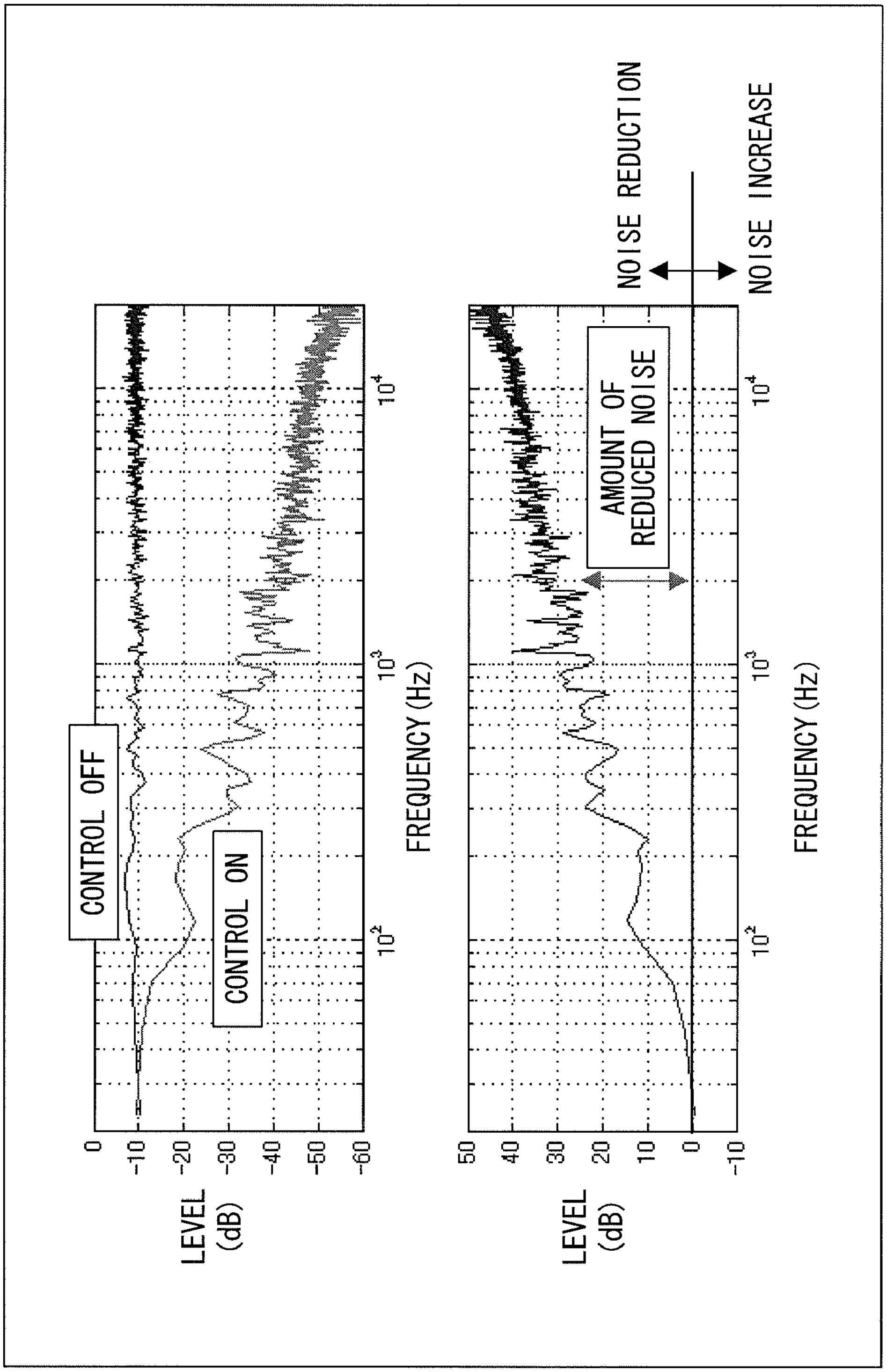
FIG. 11 shows a noise reduction effect at the control point 4 in a case where the output correction section 500 (the characteristics of FIG. 10) shown in FIG. 1 is operated.
Figure 12:
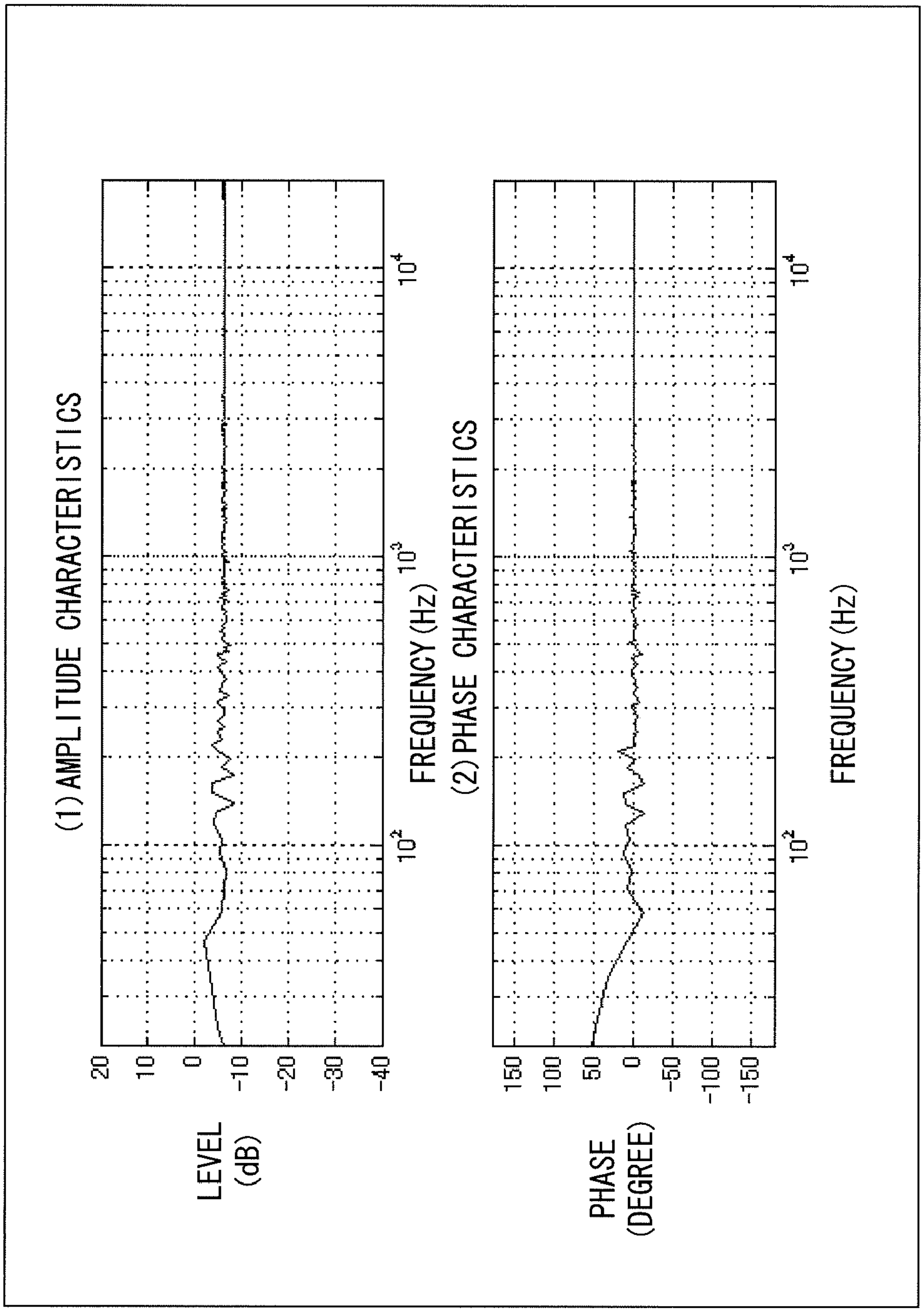
FIG. 12 shows transfer characteristics for transfer from the point X to the point Y in a case where the output correction section 500 (the characteristics of FIG. 10) shown in FIG. 1 is operated.

When, as another example, when a first-order LPF having a resonant frequency fc=60 Hz shown in FIG. 10 is applied to the LPF 501, a noise reduction effect shown in FIG. 11 is obtained. In FIG. 11, the noise increase at 60 Hz in FIG. 3 is prevented, and in addition the noise is reduced. Moreover, the noise reduction effect at a frequency equal to or lower than 2 kHz is improved. At this time, the transfer characteristics for transfer from the point X to the point Y of the noise control device shown in FIG. 1 are as shown in FIG. 12. In FIG. 12(1), the amplitude is generally −6 dB, and in FIG. 12(2), the phase is maintained at or near zero degrees.

What kind of characteristics a LPF to be applied to the LPF 501 has, may be selected depending on the situation. For example, when importance is placed on a low frequency range equal to or lower than 100 Hz, a second-order LPF having fc=90 Hz, by which the effect shown in FIG. 5 can be obtained, may be applied to the LPF 501. When importance is placed on a middle range equal to or higher than 100 Hz, a first-order LPF having fc=60 Hz, by which the effect shown in FIG. 11 can be obtained, may be applied to LPF 501. What matters is that, in a state where a LPF having such characteristics is applied to the LPF 501, the transfer characteristics for transfer from the point X to the point Y of the noise control device shown in FIG. 1 are made as equal as possible to the characteristics having the same amplitude as and the opposite phase to those of the transfer characteristics of the noise transfer system 200.

Figure 13:
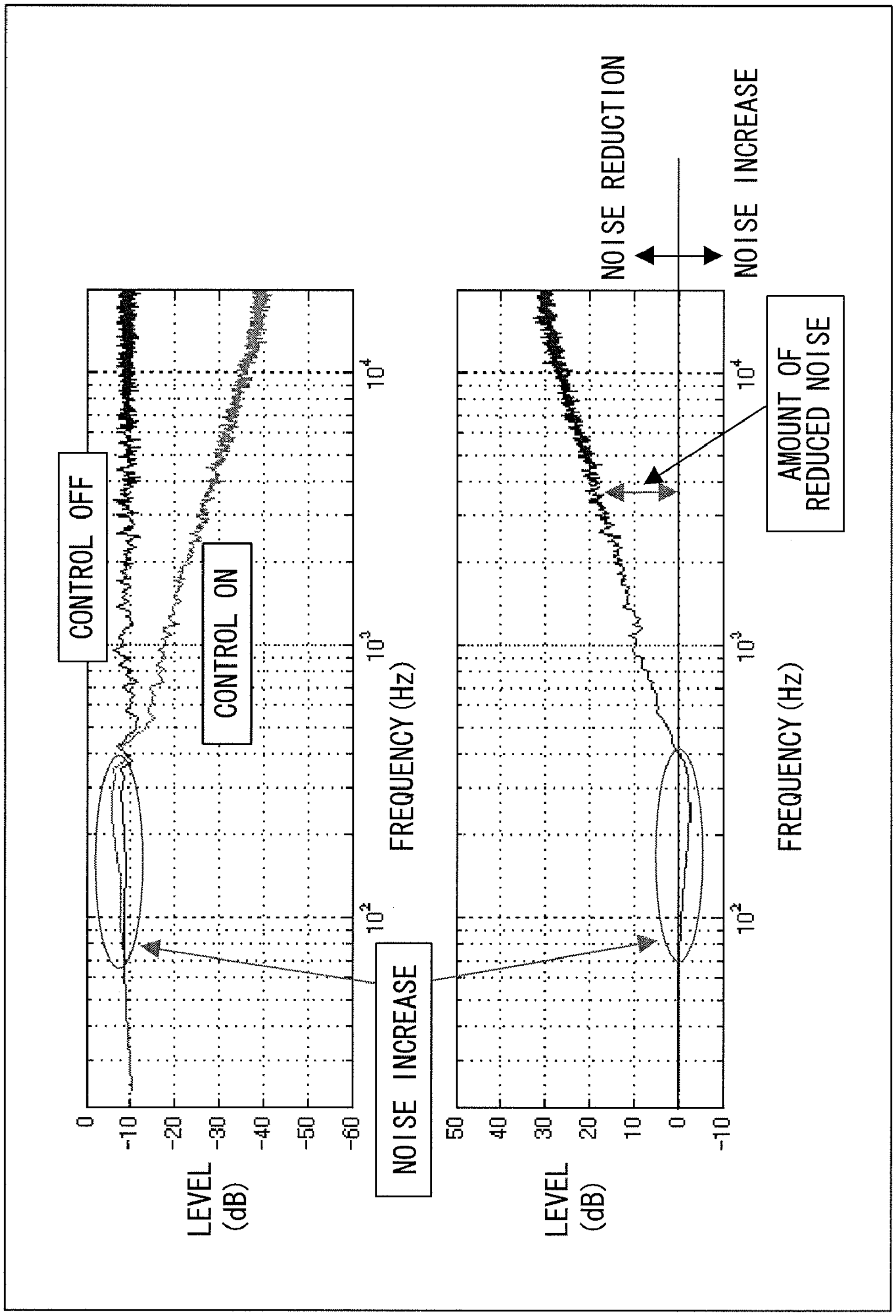
FIG. 13 shows a noise reduction effect in a case where a second-order HPF having a resonant frequency fc=1 kHz is applied to the HPF 401 shown in FIG. 1.
Figure 14:
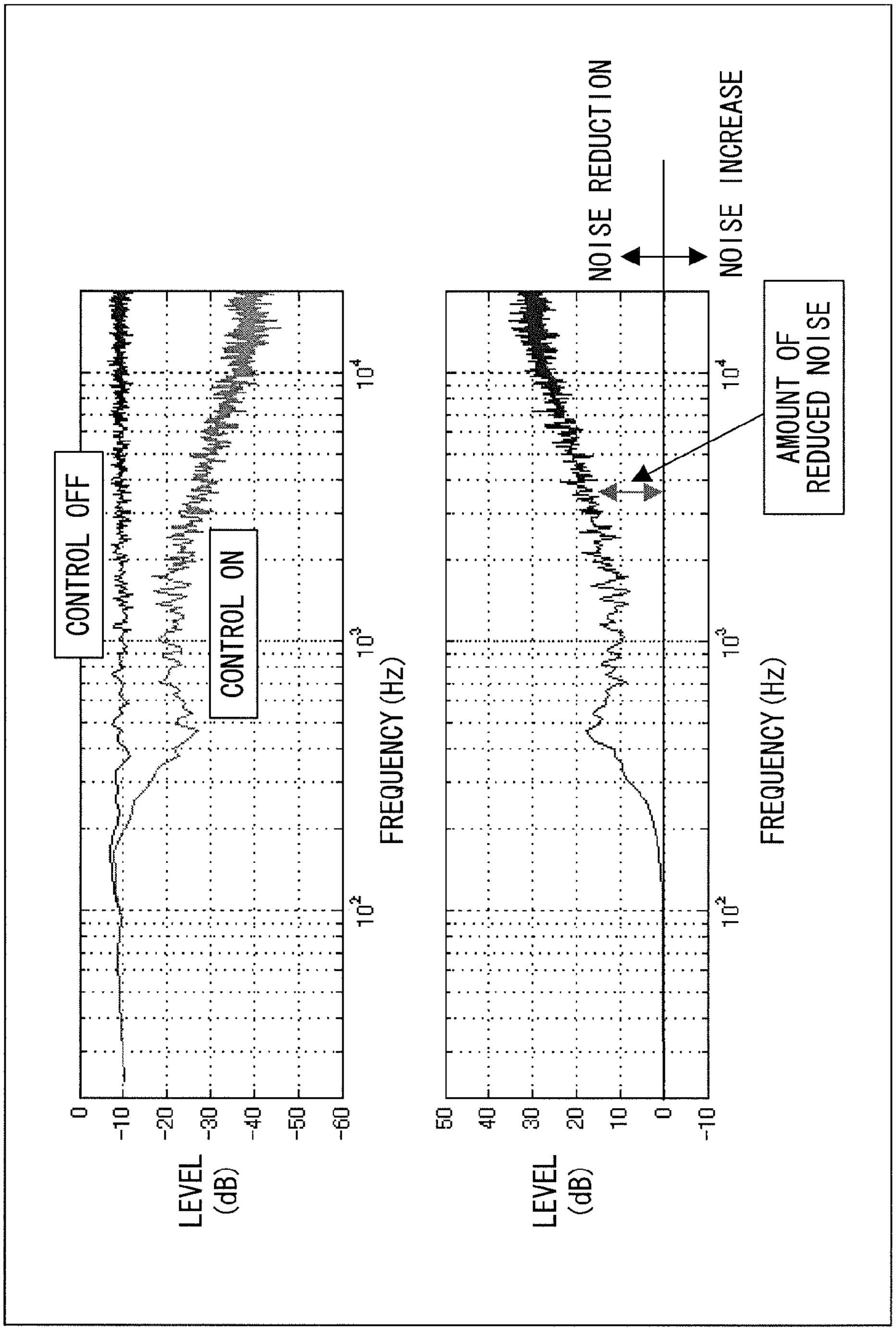
FIG. 14 shows a noise reduction effect in a case where, in the output correction section 500 shown in FIG. 1, a second-order LPF having a resonant frequency fc=600 Hz is applied to the LPF 501 and a positive feedback is performed.
Figure 15:
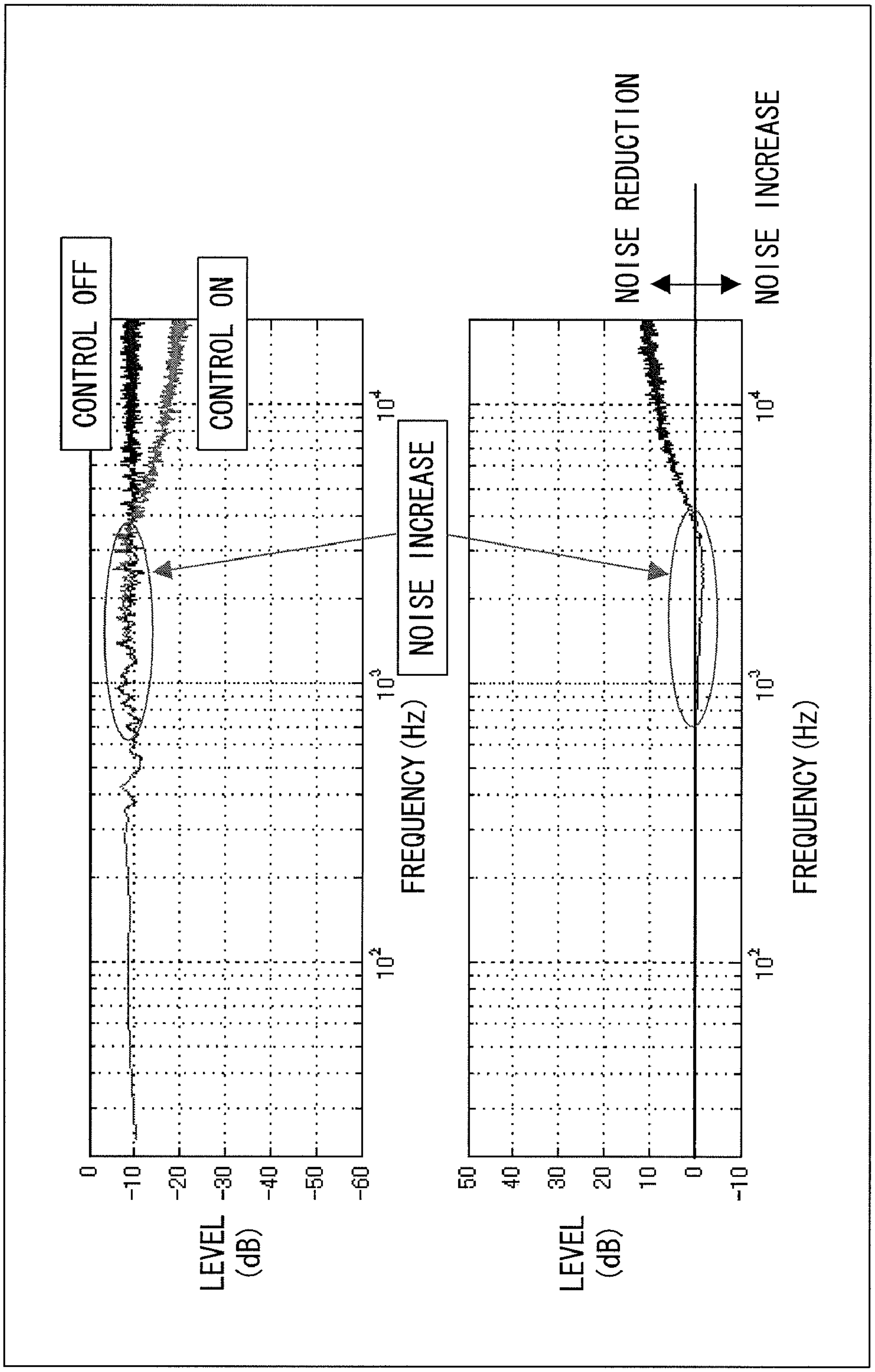
FIG. 15 shows a noise reduction effect in a case where a second-order HPF having a resonant frequency fc=10 kHz is applied to the HPF 401 shown in FIG. 1.
Figure 16:
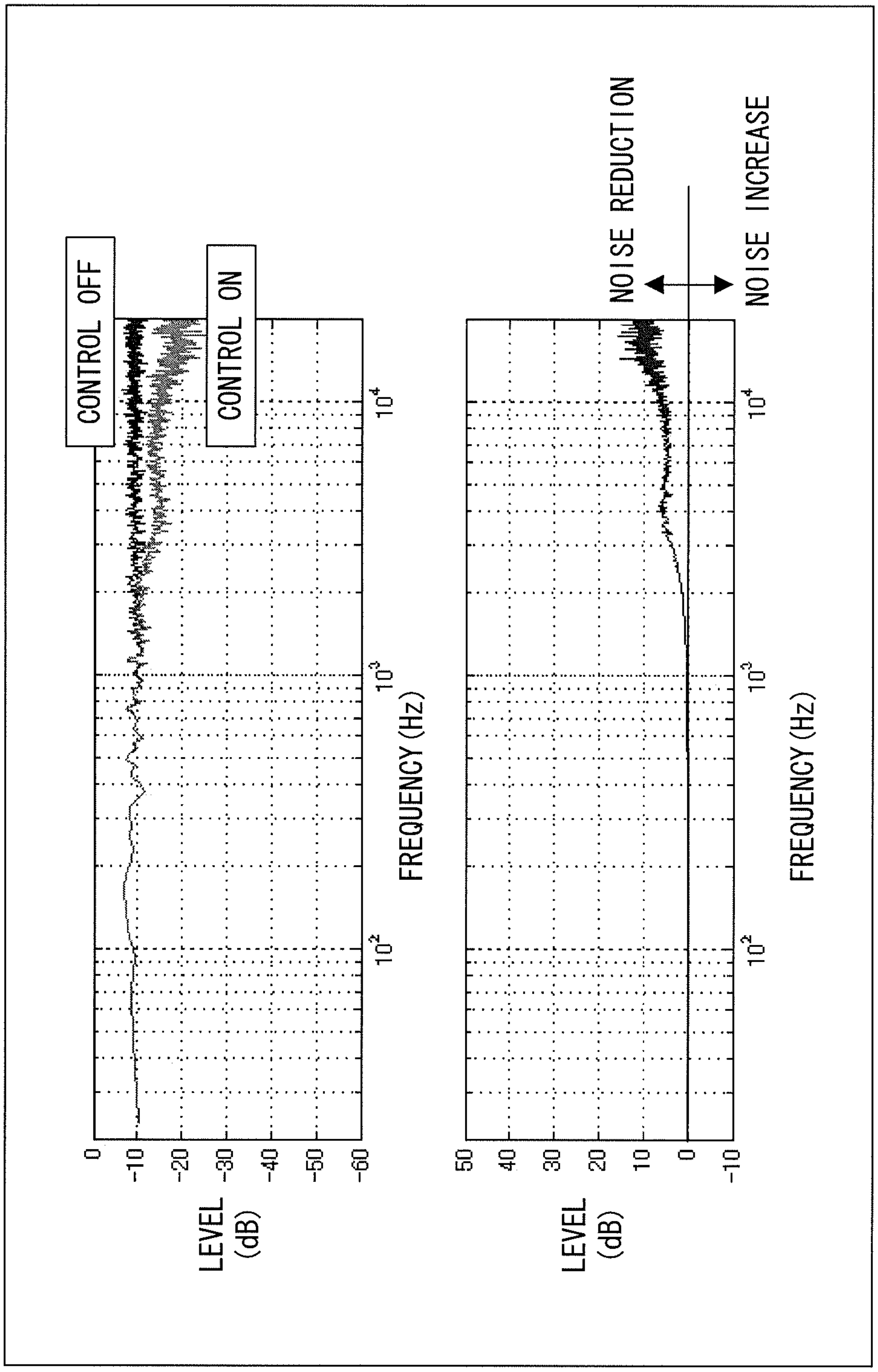
FIG. 16 shows a noise reduction effect in a case where, in the output correction section 500 shown in FIG. 1, a second-order LPF having a resonant frequency fc=6 kHz is applied to the LPF 501 and a positive feedback is performed.

Next, whether or not the noise control device shown in FIG. 1 can perform such a control as to provide the above-described noise reduction effect when the resonant frequency of the HPF 401 of FIG. 1 is set to a high frequency range, will be examined. FIG. 13 shows a noise reduction effect in a case where a second-order HPF having a resonant frequency fc=1 kHz is applied to the HPF 401. The noise increases at 80 to 400 Hz. On the other hand, FIG. 14 shows a noise reduction effect in a case where: a second-order LPF having a resonant frequency fc=600 Hz is applied to the LPF 501 of FIG. 1; an appropriate positive value is set in the gain adjuster 503; and an FB formed in the output correction section 500 is made a positive feedback. As shown in FIG. 14, a noise increase is suppressed at 80 to 400 Hz, and moreover the noise reduction effect is improved at a frequency equal to or lower than 1 kHz. In the same manner, FIG. 15 shows a noise reduction effect in a case where a second-order HPF having a resonant frequency fc=10 kHz is applied to the HPF 401. The noise increases at 800 to 4000 Hz. On the other hand, FIG. 16 shows a noise reduction effect in a case where: a second-order LPF having a resonant frequency fc=6 kHz is applied to the LPF 501 of FIG. 1; an appropriate positive value is set in the gain adjuster 503; and an FB formed in the output correction section 500 is made a positive feedback. As shown in FIG. 16, a noise increase is suppressed at 800 to 4000 Hz, and moreover the noise reduction effect is improved at a frequency equal to or lower than 6 kHz.

From the above, it can be seen that, even when the resonant frequency of the HPF 401 of FIG. 1 is set to a high frequency range, that is, even when the resonant frequency fo of a control speaker is at a high-frequency side, the noise control device shown in FIG. 1 can perform such a control as to suppress the above-described noise increase and also can improve the noise reduction effect.

The noise control device shown in FIG. 1 has been described with the HPF 401 serving as a control speaker in the control acoustic system 400. In the following, an operation performed when a real speaker is used will be described.

Figure 17:
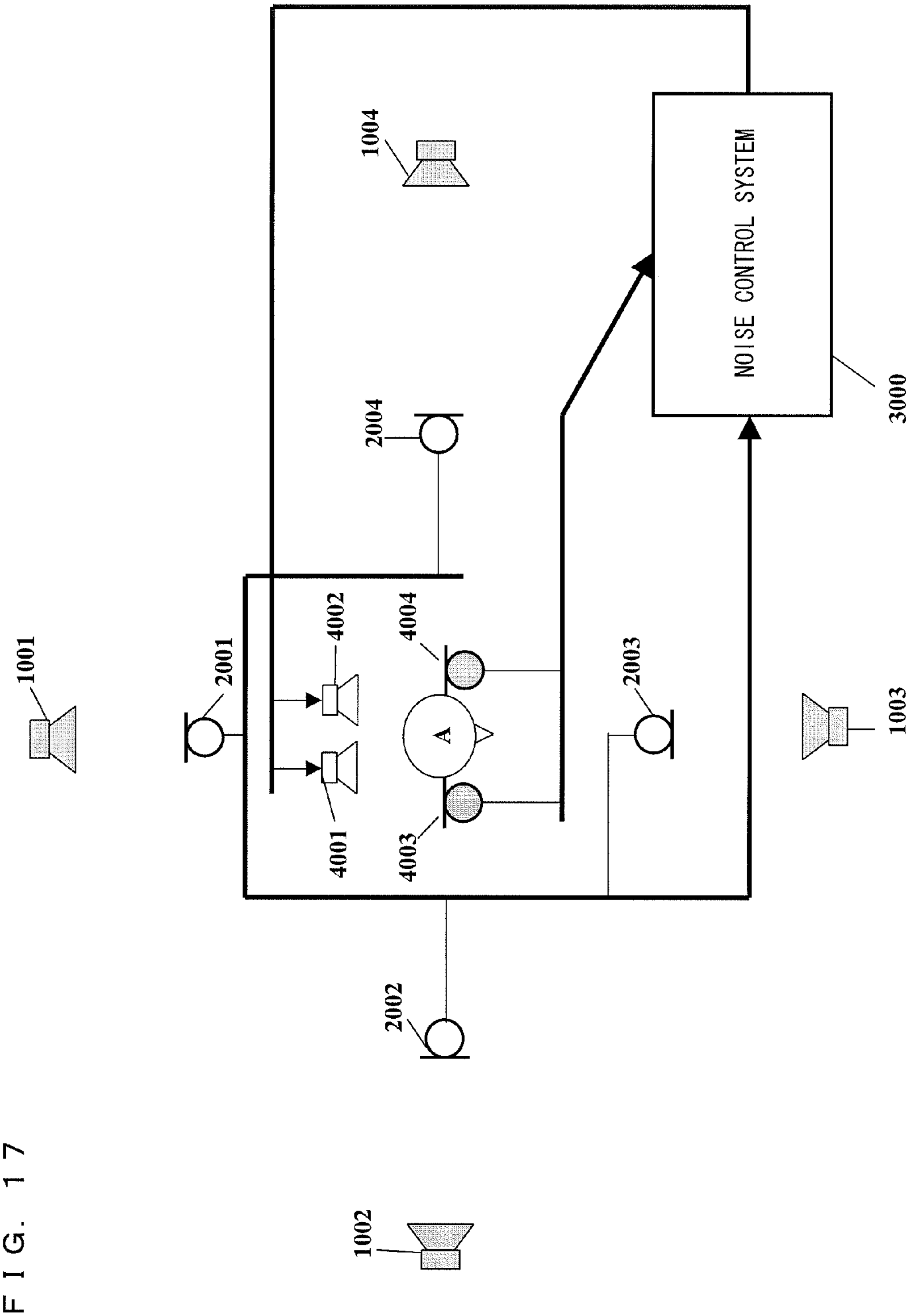
FIG. 17 shows an overall configuration of a noise control device in a case where a real speaker is used for a control acoustic system.
Figure 18:
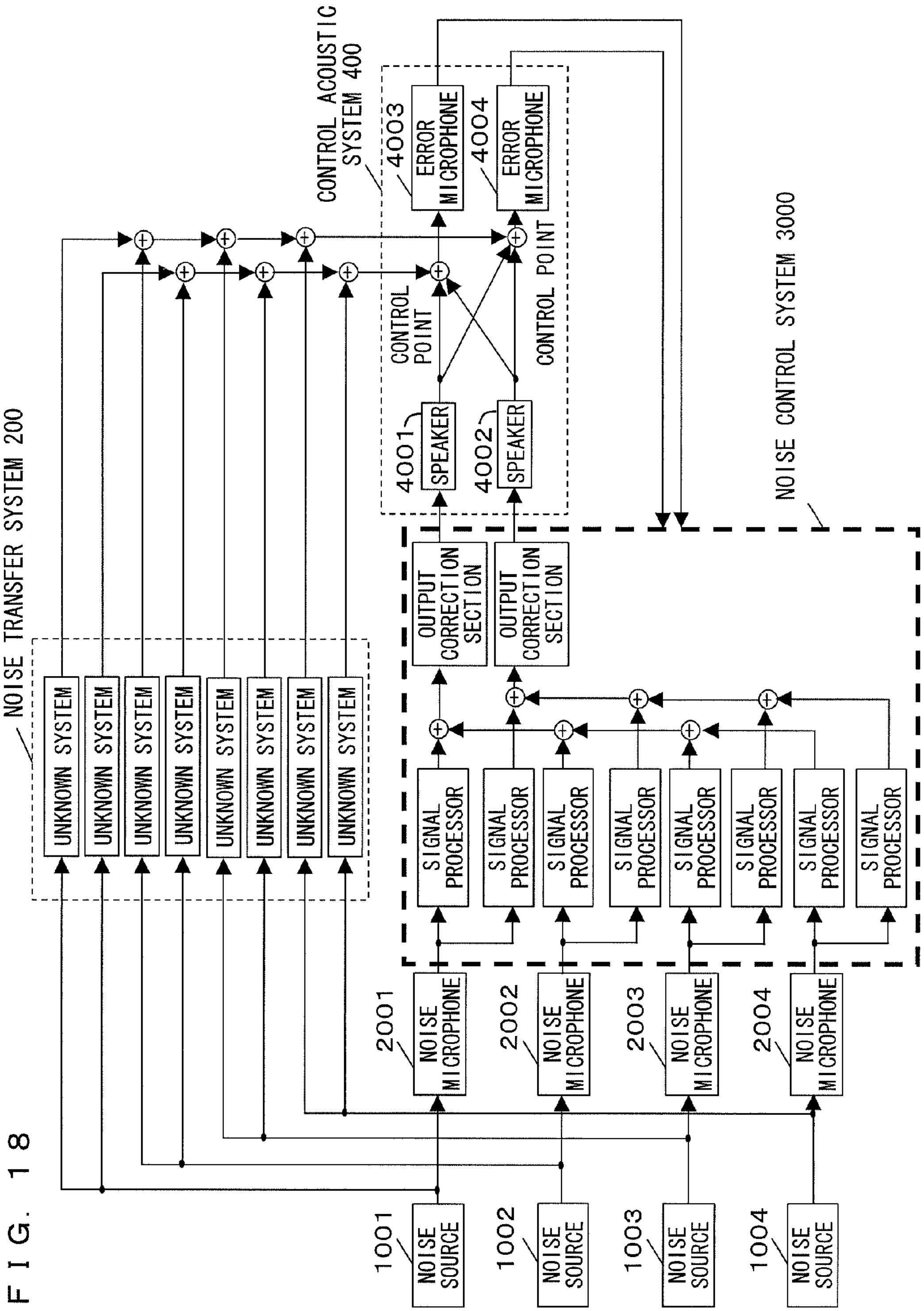
FIG. 18 schematically shows the noise control device shown in FIG. 17, as a signal process block diagram.

FIG. 17 shows an overall configuration of a noise control device in a case where a real speaker is used for a control acoustic system. In FIG. 17, the noise control device detects a plurality of noise sources 1001 to 1004 by a plurality of corresponding noise microphones 2001 to 2004, respectively, and processes a detected noise in a noise control system 3000. Then, the noise control device reproduces an output signal outputted from the noise control system 3000 by a plurality of speakers 4001 and 4002, thereby reducing a noise at a plurality of control points 4003 and 4004. FIG. 18 schematically shows the noise control device shown in FIG. 17, as a block diagram similar to that of FIG. 1. In FIG. 18, the noise control system 3000 firstly operates signal processors without operating output correction sections (outputs inputs of the output correction sections without any change), to perform a signal process on noise signals outputted from the noise sources 1001 to 1004 detected by the noise microphones 2001 to 2004. The noise signals having the signal process performed thereon are reproduced by the speakers 4001 and 4002. At error microphones 4003 and 4004 which are the control points, the noise signals outputted from the speakers 4001 and 4002 interfere with noises that are outputted from the noise sources 1001 to 1004 and reach the error microphones 4003 and 4004 via a noise transfer system 200 which is an unknown system. Error signals remaining as a result of this cancellation are inputted to the noise control system 3000. The noise control system 3000 obtains characteristics (a coefficient) of the signal processor such that the inputted error signal can be minimized. Consequently, noises at the error microphones 4003 and 4004 which are the control points can be reduced.

Figure 19:
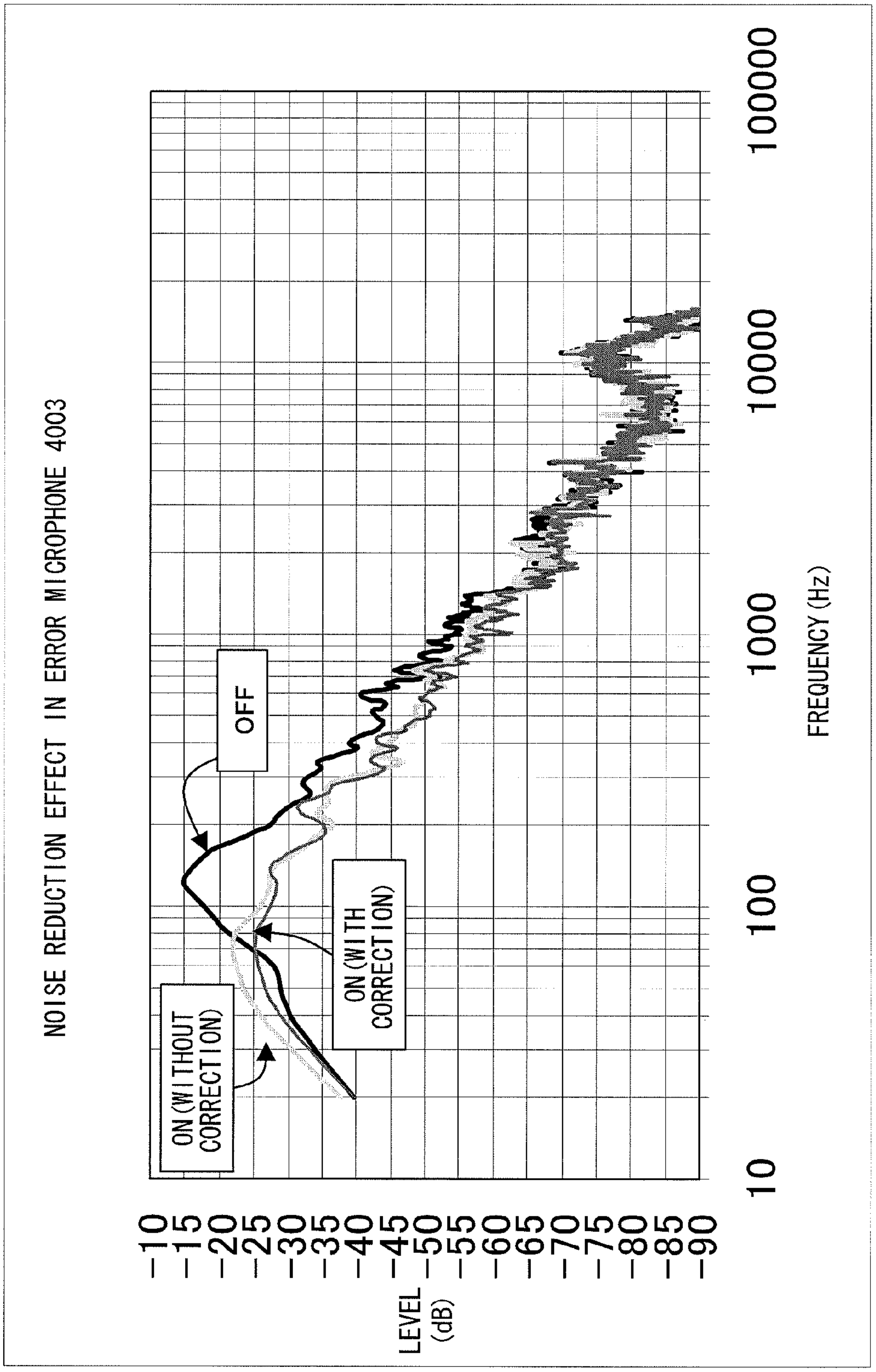
FIG. 19 shows a noise reduction effect at an error microphone 4003 shown in FIGS. 17 and 18.
Figure 20:
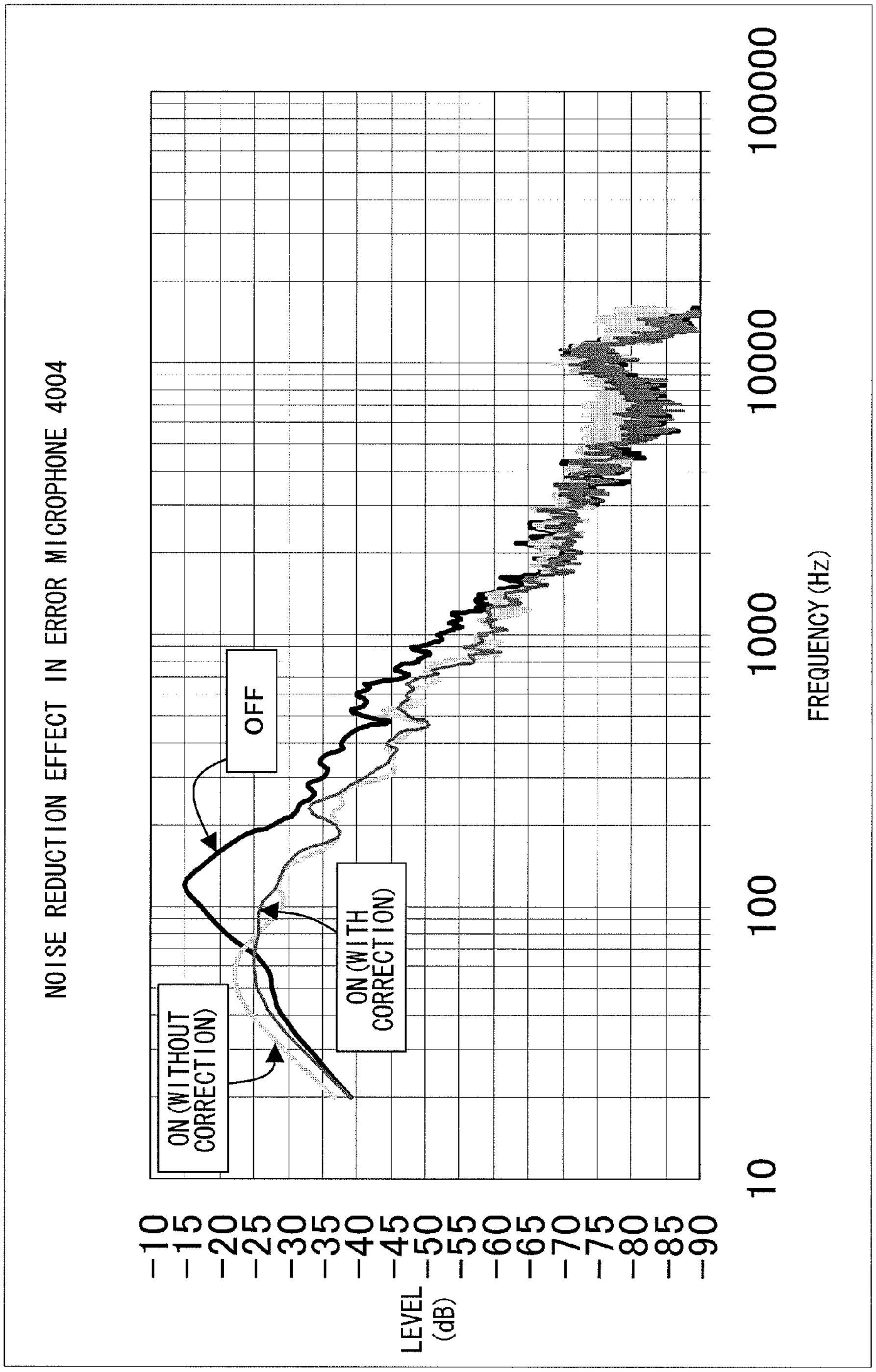
FIG. 20 shows a noise reduction effect at an error microphone 4004 shown in FIGS. 17 and 18.

Then, by using the obtained coefficient, the noise control system 3000 causes the signal processor to operate as a fixed coefficient filter, and causes the output correction section to operate. The output correction section has, for example, a configuration similar to that of the output correction section 500 of FIG. 1, and sets a parameter such as a filter coefficient of the LPF 501 and a gain of the gain adjuster 503 in the output correction section 500, to an appropriate value thus far described above. FIG. 19 shows a noise reduction effect in the error microphone 4003 shown in FIGS. 17 and 18. FIG. 19 shows noise characteristics “OFF” obtained in a case where the noise control is not performed, noise characteristics “ON (without correction)” obtained in a case where the noise control is performed without the output correction section being operated, and noise characteristics “ON (with correction)” obtained in a case where the noise control is performed with the output correction section being operated. As shown in FIG. 19, in the noise characteristics “ON (without correction)”, as compared with in the noise characteristics “OFF”, there is a noise increase of 5 dB or more at a frequency equal to or lower than 80 Hz. On the other hand, in the noise characteristics “ON (with correction)”, this noise increase is suppressed to less than 0 to 5 dB. In the same manner, FIG. 20 shows a noise reduction effect in the error microphone 4004 shown in FIGS. 17 and 18. As shown in FIG. 20, in the noise characteristics "ON (without correction)", as compared with in the noise characteristics "OFF", there is a noise increase of 5 dB or more at a frequency equal to or lower than 70 Hz. On the other hand, in the noise characteristics "ON (with correction)", this noise increase is suppressed to less than 0 to 5 dB. From the above, it can be confirmed that the noise control device according to the present invention is effective also when a real speaker is used.

Figure 21:
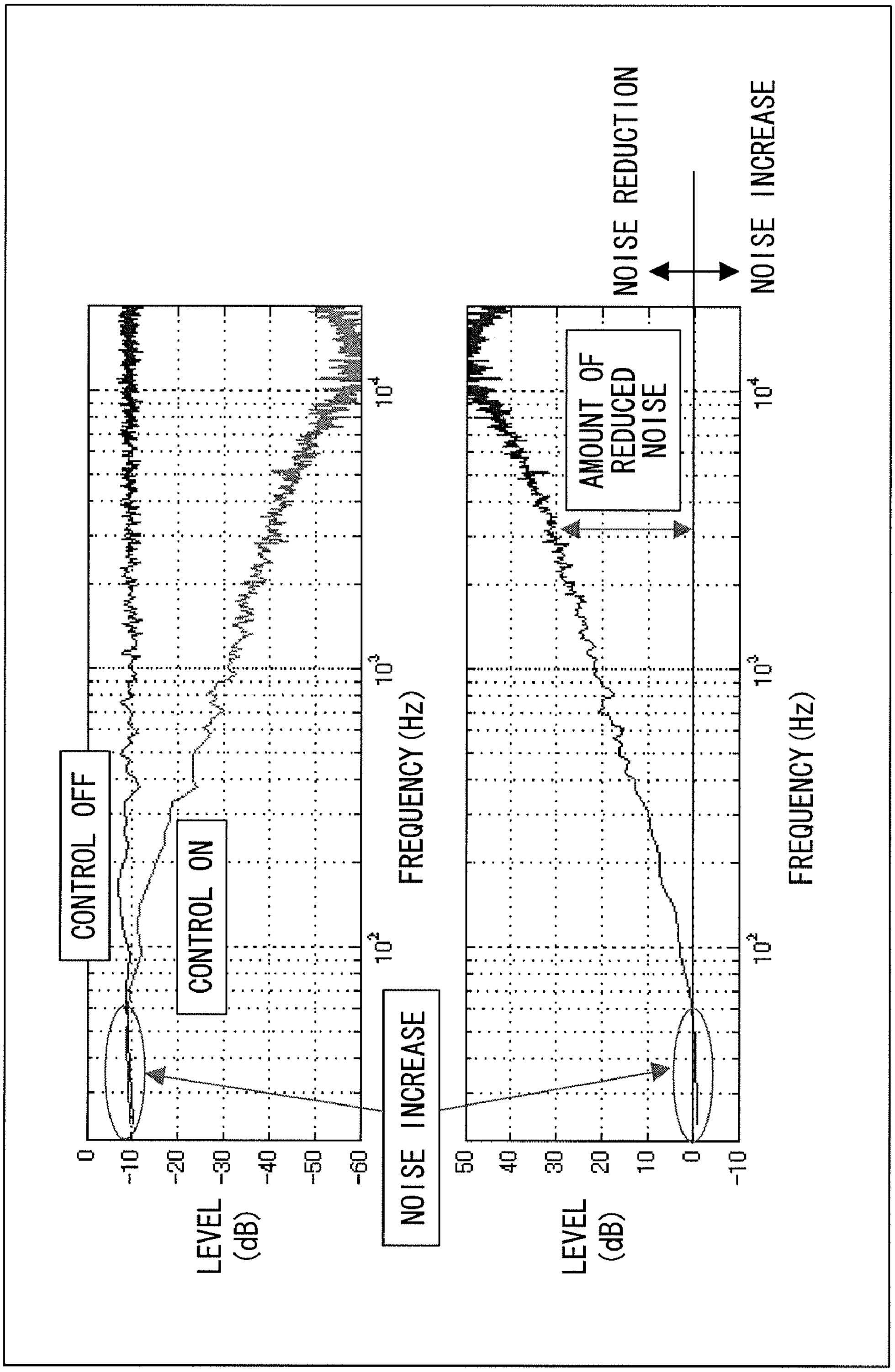
FIG. 21 shows a noise reduction effect in a case where, in the output correction section 500 shown in FIG. 1, a first-order LPF having a resonant frequency fc=60 Hz is applied to the LPF 501 and a negative feedback is performed.
Figure 22:
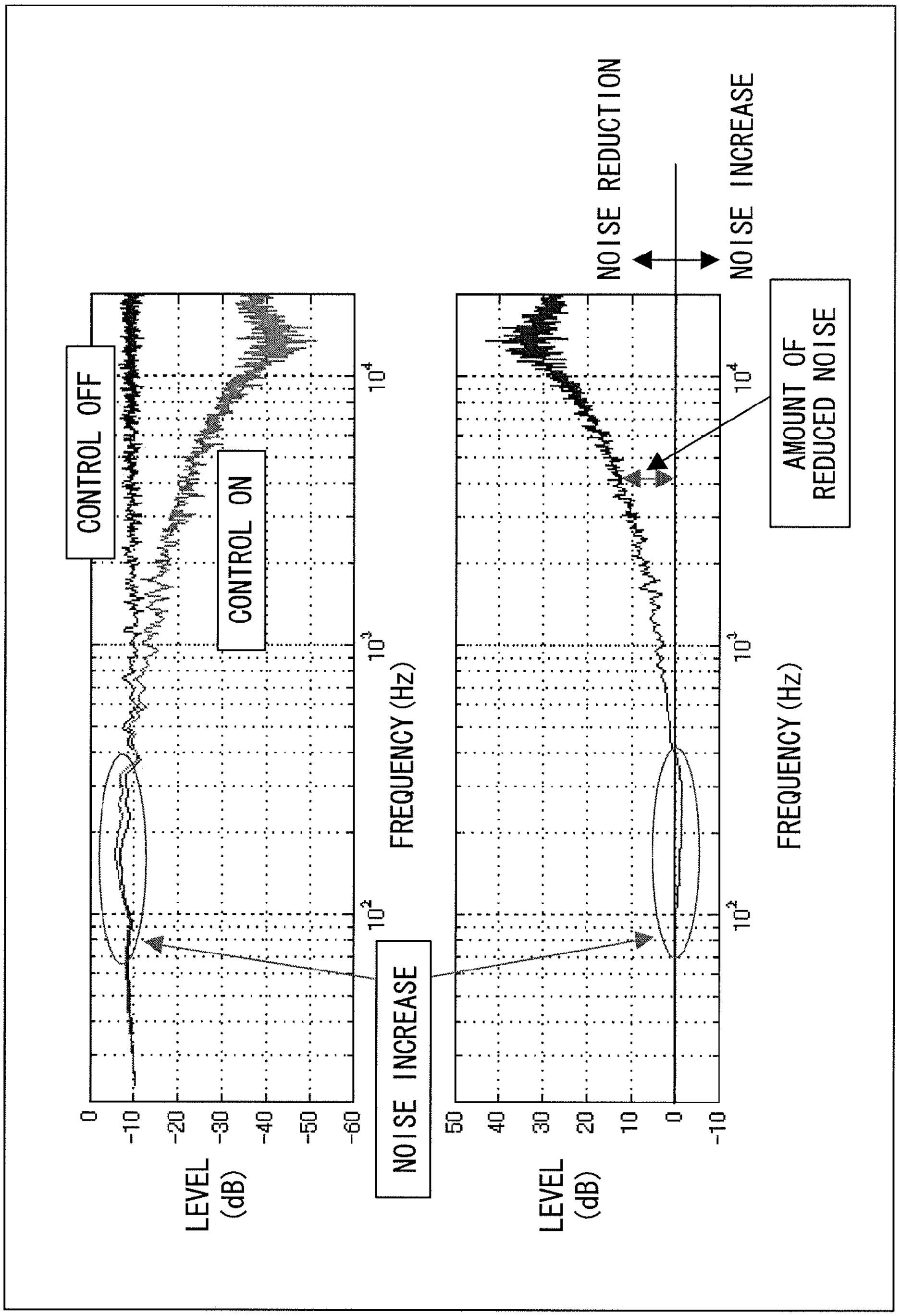
FIG. 22 shows a noise reduction effect in a case where, in the output correction section 500 shown in FIG. 1, a first-order LPF having a resonant frequency fc=600 Hz is applied to the LPF 501 and a negative feedback is performed.
Figure 23:
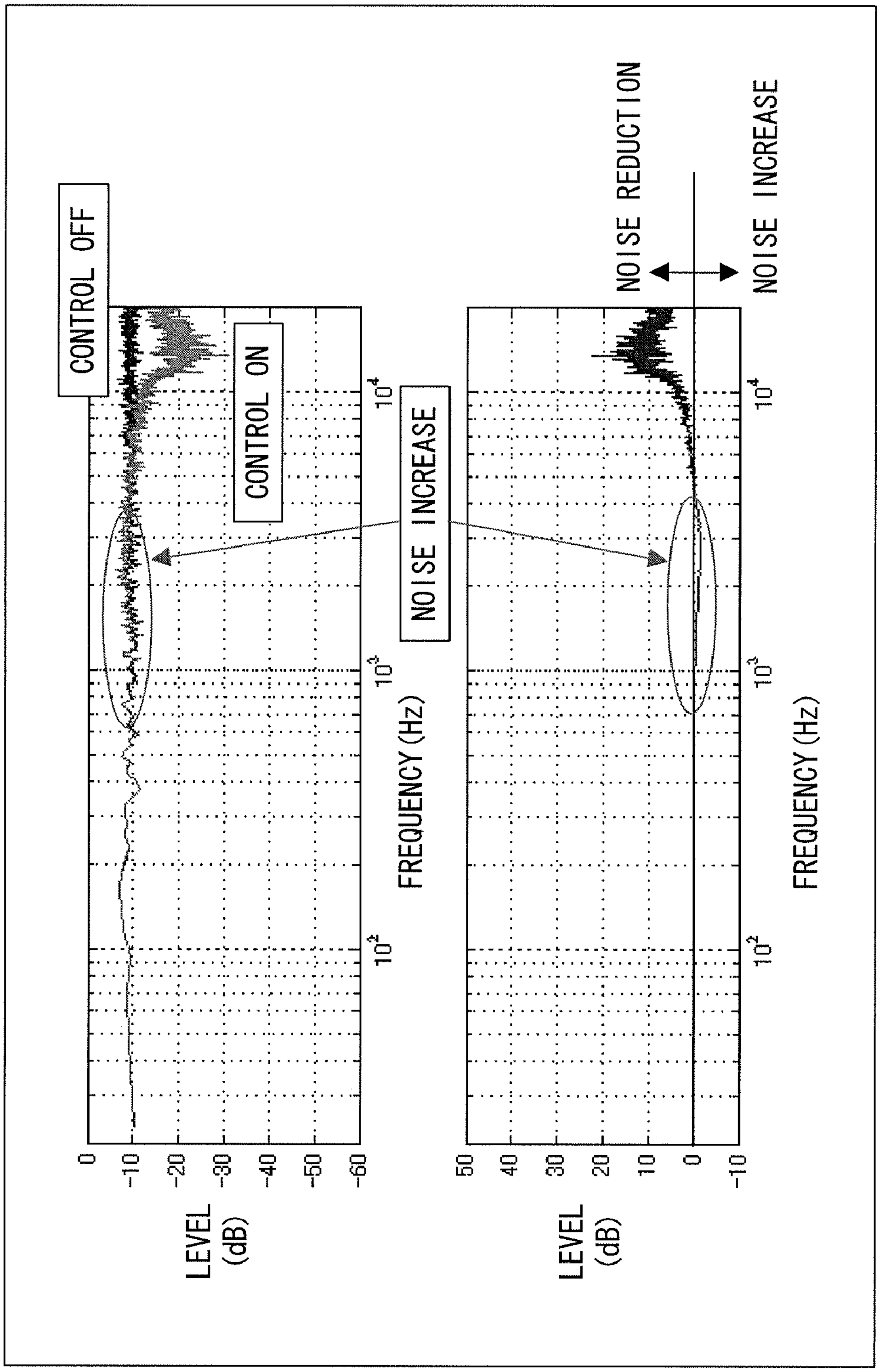
FIG. 23 shows a noise reduction effect in a case where, in the output correction section 500 shown in FIG. 1, a first-order LPF having a resonant frequency fc=6 kHz is applied to the LPF 501 and a negative feedback is performed.

Hereinbefore, the positive feedback in which a positive value is set in the gain adjuster 503 of FIG. 1 has been described. Hereinafter, a negative feedback in which a negative value is set will be described. The noise reduction effect in a case where a second-order HPF having a resonant frequency fc=100 Hz is applied to the HPF 401 of FIG. 1 and the output correction section 500 is not operated, is shown in FIG. 3. Thus, when: a first-order LPF having a resonant frequency fc=60 Hz is applied to the LPF 501 of FIG. 1; an appropriate negative value is set in the gain adjuster 503; and a negative feedback is performed, a noise reduction effect as shown in FIG. 21 is obtained. In FIG. 21, as compared with in FIG. 3, the noise increase at a frequency equal to or lower than 60 Hz is decreased, but not completely eliminated. Also, at a frequency equal to or higher than 100 Hz, the noise reduction effect deteriorates. In the same manner, when: a second-order HPF having a resonant frequency fc=1 kHz is applied to the HPF 401 of FIG. 1; a first-order LPF having a resonant frequency fc=600 Hz is applied to the LPF 501; an appropriate negative value is set in the gain adjuster 503; and a negative feedback is performed, a noise reduction effect as shown in FIG. 22 is obtained. In FIG. 22, as compared with in FIG. 13, the noise increase at a frequency equal to or lower than 400 Hz is decreased, but not completely eliminated. Also, at a frequency equal to or higher than 600 Hz, the noise reduction effect deteriorates. Furthermore, when: a second-order HPF having a resonant frequency fc=10 kHz is applied to the HPF 401 of FIG. 1; a first-order LPF having a resonant frequency fc=6 kHz is applied to the LPF 501; an appropriate negative value is set in the gain adjuster 503; and a negative feedback is performed, a noise reduction effect as shown in FIG. 23 is obtained. In FIG. 23, as compared with in FIG. 15, the noise increase at a frequency equal to or lower than 2 kHz is reduced, but the amount of the reduction is small. Also, at a frequency equal to or higher than 4 kHz, the noise reduction effect deteriorates.

In this manner, when the output correction section 500 is controlled by using the negative feedback, the noise increase can be suppressed in a certain amount, but the noise increase cannot be completely suppressed, unlike the positive feedback. However, in a control using the positive feedback, the level rises in a lower range, and thus there is a possibility of overflow in a low frequency range in the output correction section 500. In contrast, in a control using the negative feedback, the level drops in a lower range or the level does not rise to a certain level or higher, and therefore the operation of the output correction section 500 can be stabilized. In the positive feedback as well, depending on conditions, the operation of the output correction section 500 can be stabilized. Thus, which of the positive feedback and the negative feedback is to be selected may be determined in accordance with environments and conditions of where the feedback is applied.

Figure 24:
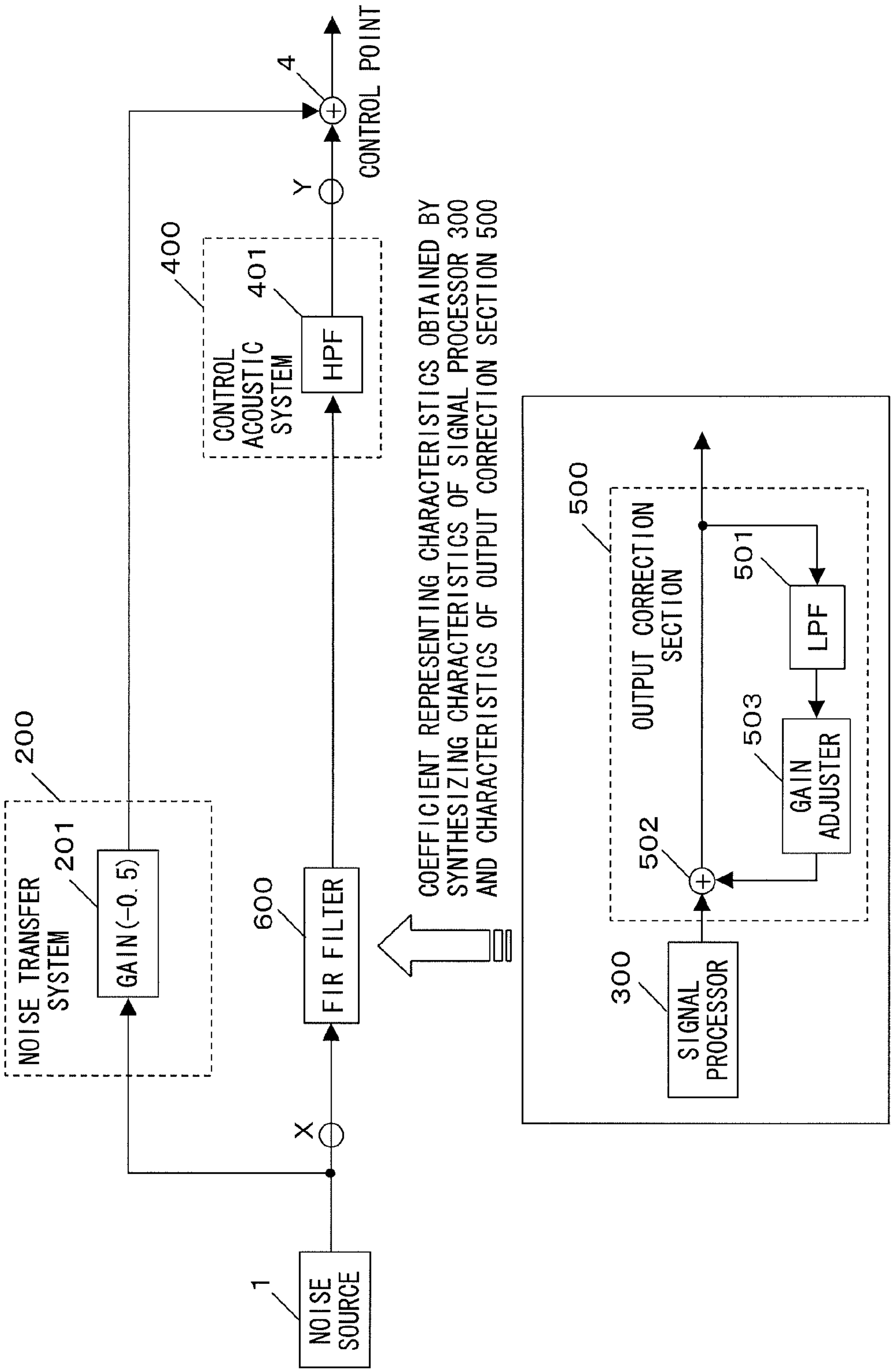
FIG. 24 shows a configuration obtained by synthesizing characteristics of the signal processor 300 and characteristics of the output correction section 500 shown in FIG. 1 and setting characteristics resulting from the synthesis, as a coefficient, to an FIR filter 600.
Figure 25:
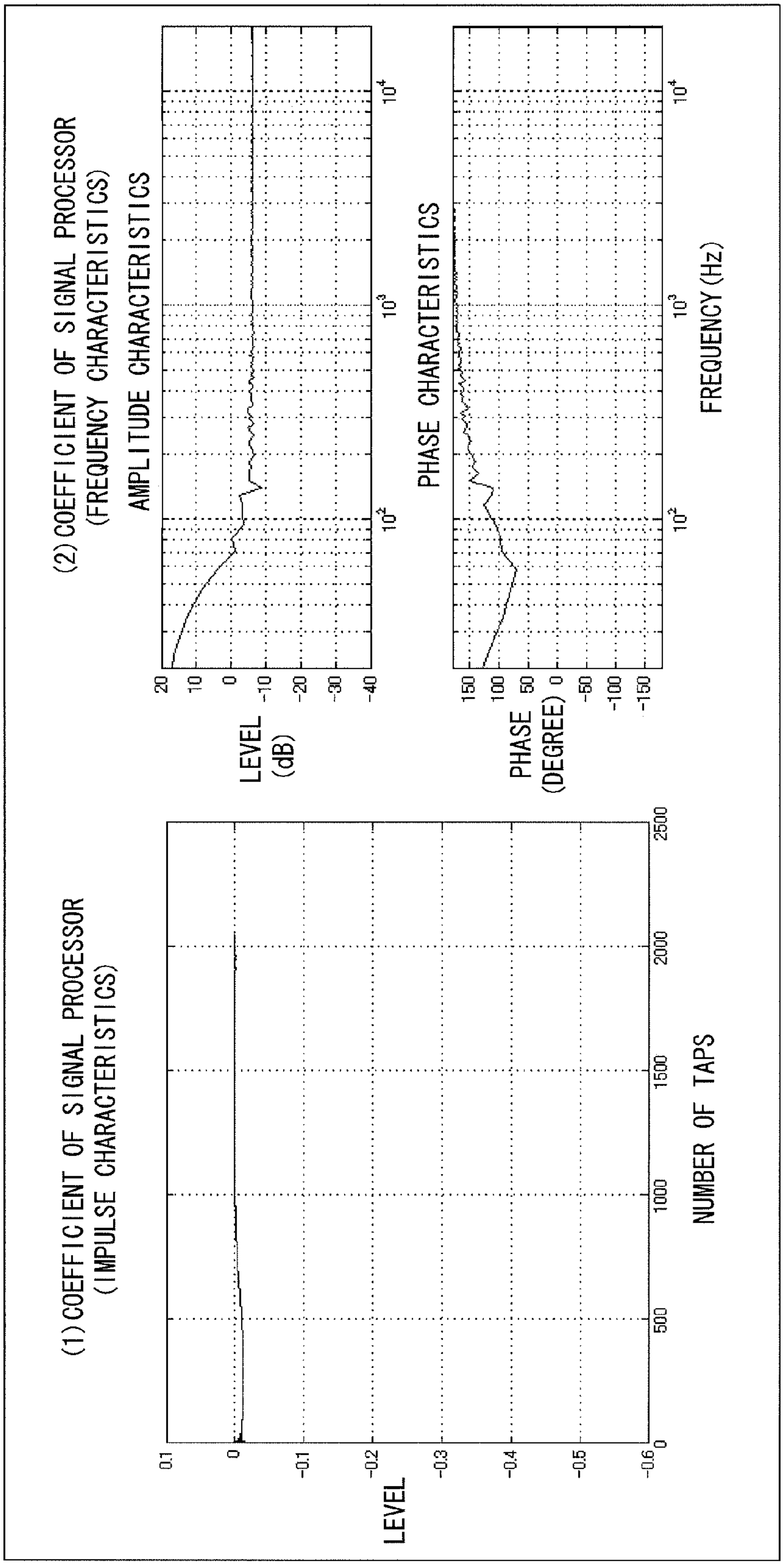
FIG. 25 shows the characteristics of the signal processor 300 in a case where the noise reduction effect shown in FIG. 3 is obtained.

Next, a case where the signal processor 300 and the output correction section 500 of FIG. 1 are synthesized into a signal filter will be described. FIG. 24 shows a configuration obtained by synthesizing the characteristics of the signal processor 300 of FIG. 1 and the characteristics of the output correction section 500 of FIG. 1 and setting characteristics resulting from the synthesis, as a coefficient, to an FIR filter 600.

Figure 26:
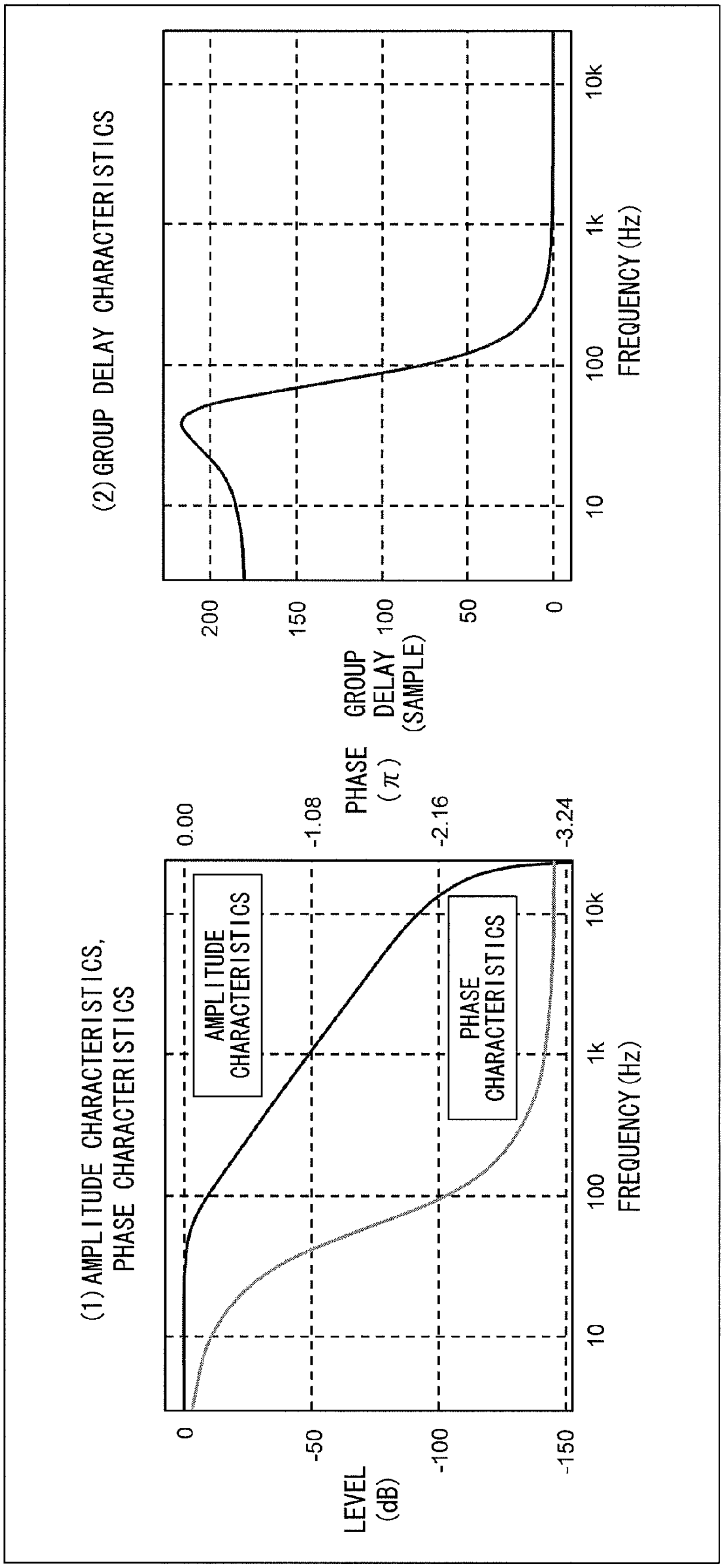
FIG. 26 shows other characteristics of the LPF 501 of the output correction section 500 shown in FIG. 1.
Figure 27:
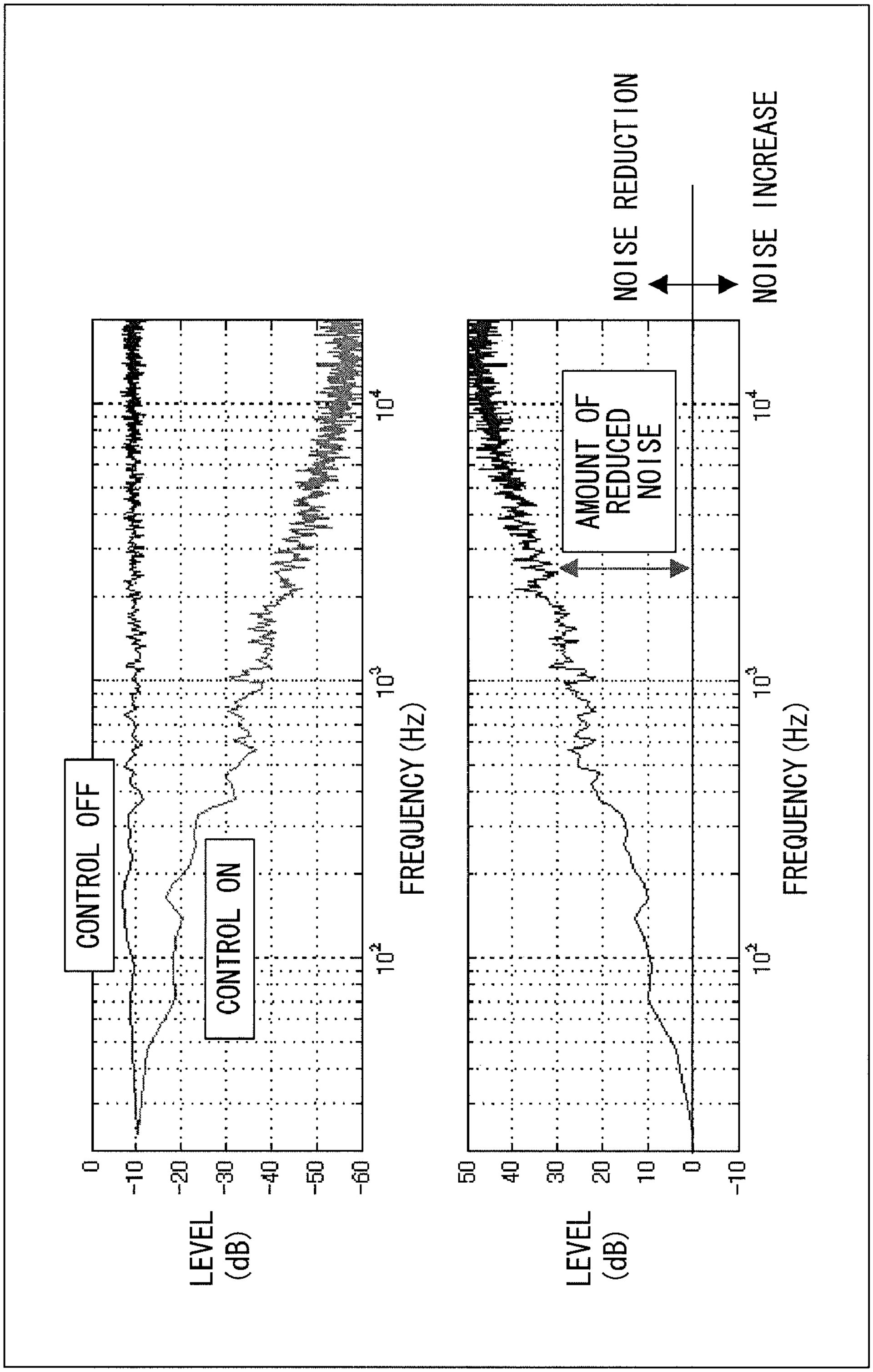
FIG. 27 shows a noise reduction effect at the control point 4 in a case where the output correction section 500 (the characteristics of FIG. 26) shown in FIG. 1 is operated.

Firstly, in the noise control device shown in FIG. 1, from which a noise control device including the FIR filter 600 shown in FIG. 24 originates, the noise reduction effect in a case where a control is performed without the output correction section 500 being operated, is as shown in FIG. 3. In a case where the noise reduction effect shown in FIG. 3 is obtained, the signal processor 300 has characteristics shown in FIG. 25, if the signal processor 300 is designed as an FIR filter having 2048 taps for example. Here, a second-order LPF having a resonant frequency fc=60 Hz and having characteristics shown in FIG. 26 is applied to the LPF 501 of the output correction section 500 of FIG. 1. FIG. 27 shows a noise reduction effect at a control point in a case where the output correction section 500 (the characteristics of FIG. 26) shown in FIG. 1 is operated.

Figure 28:
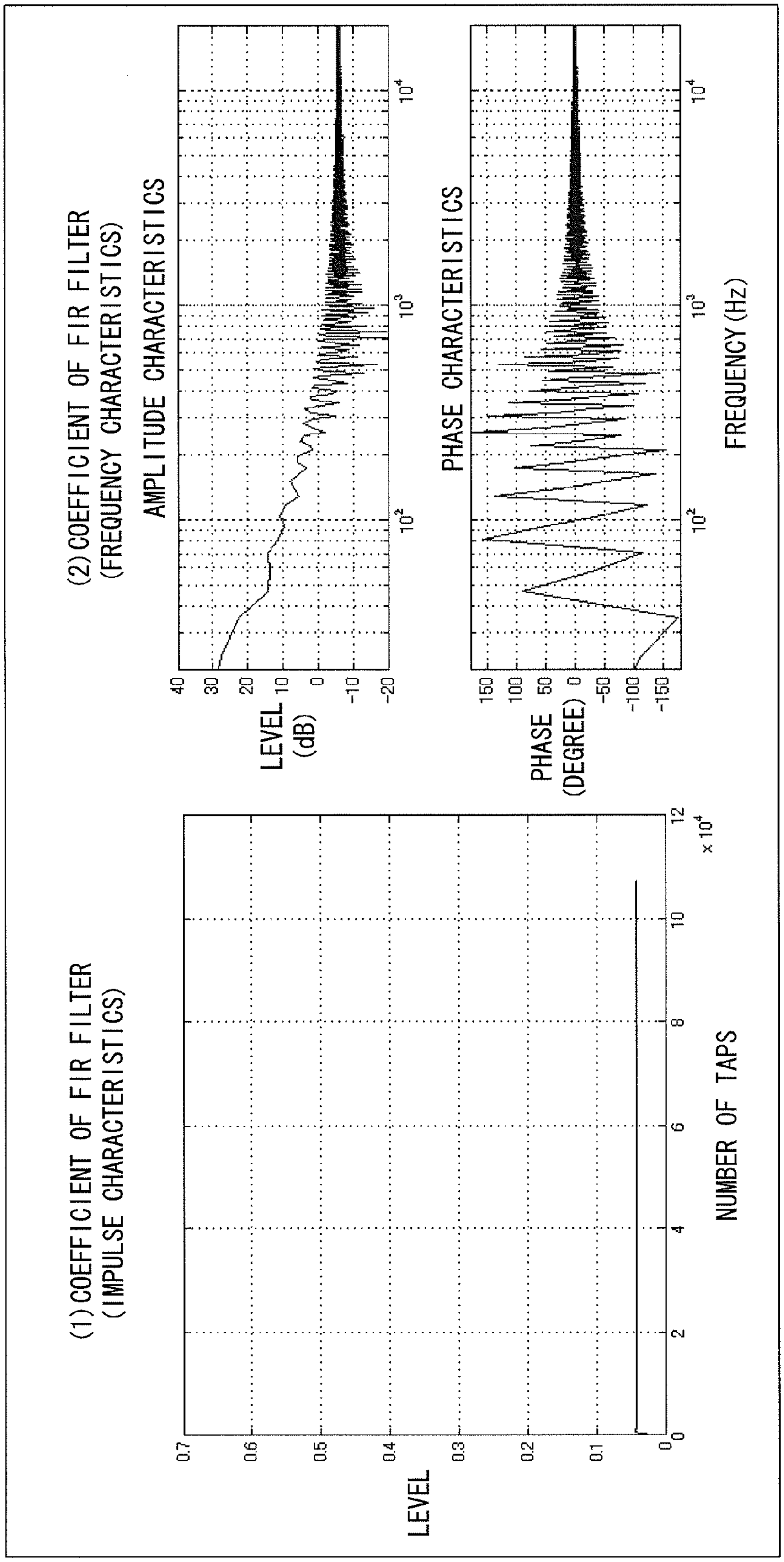
FIG. 28 shows characteristics of the FIR filter 600 shown in FIG. 24.
Figure 29:
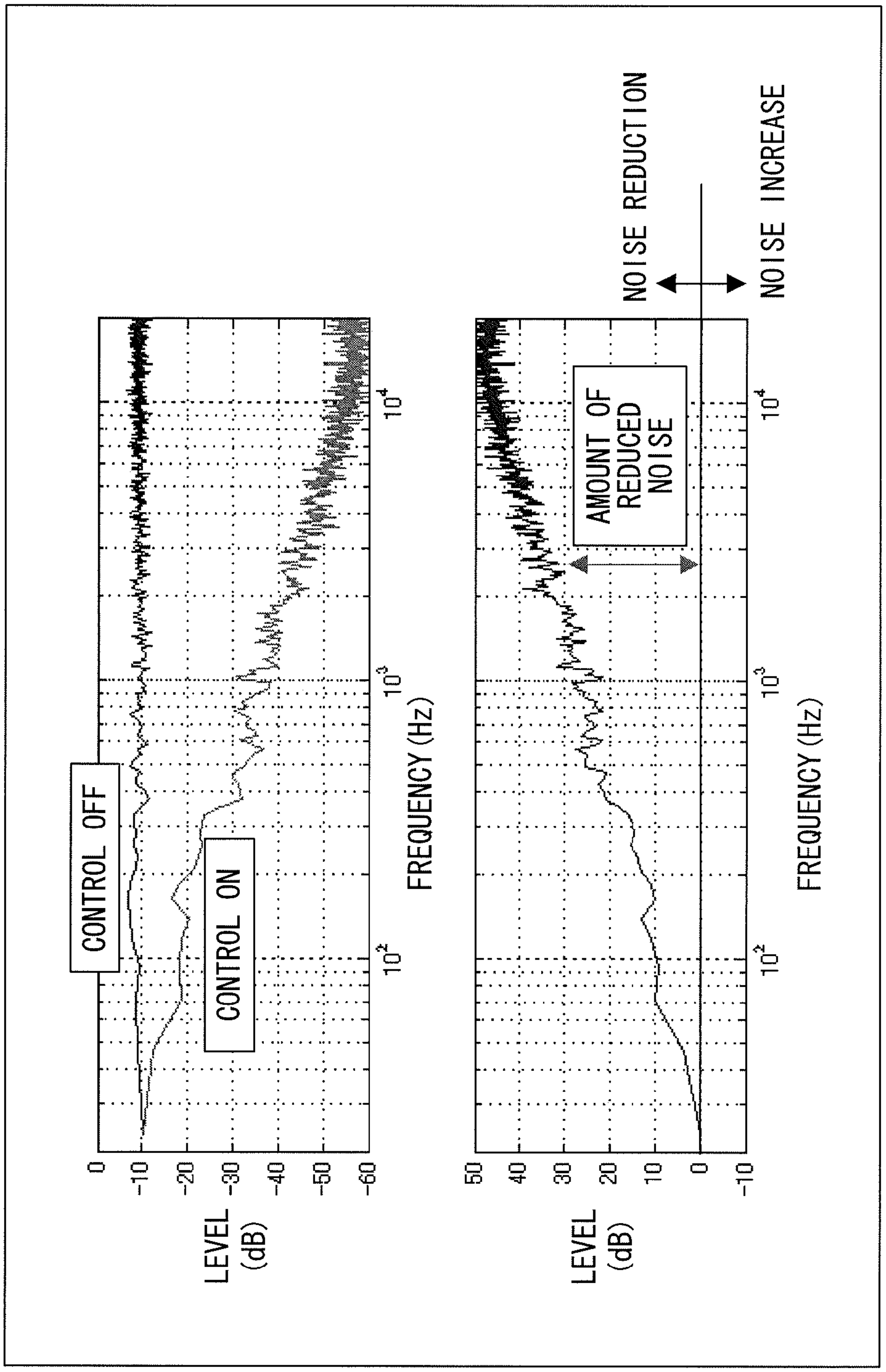
FIG. 29 shows a noise reduction effect at a control point 4 in a case where the FIR filter 600 (when the number of taps is large) shown in FIG. 24 is operated.
Figure 30:
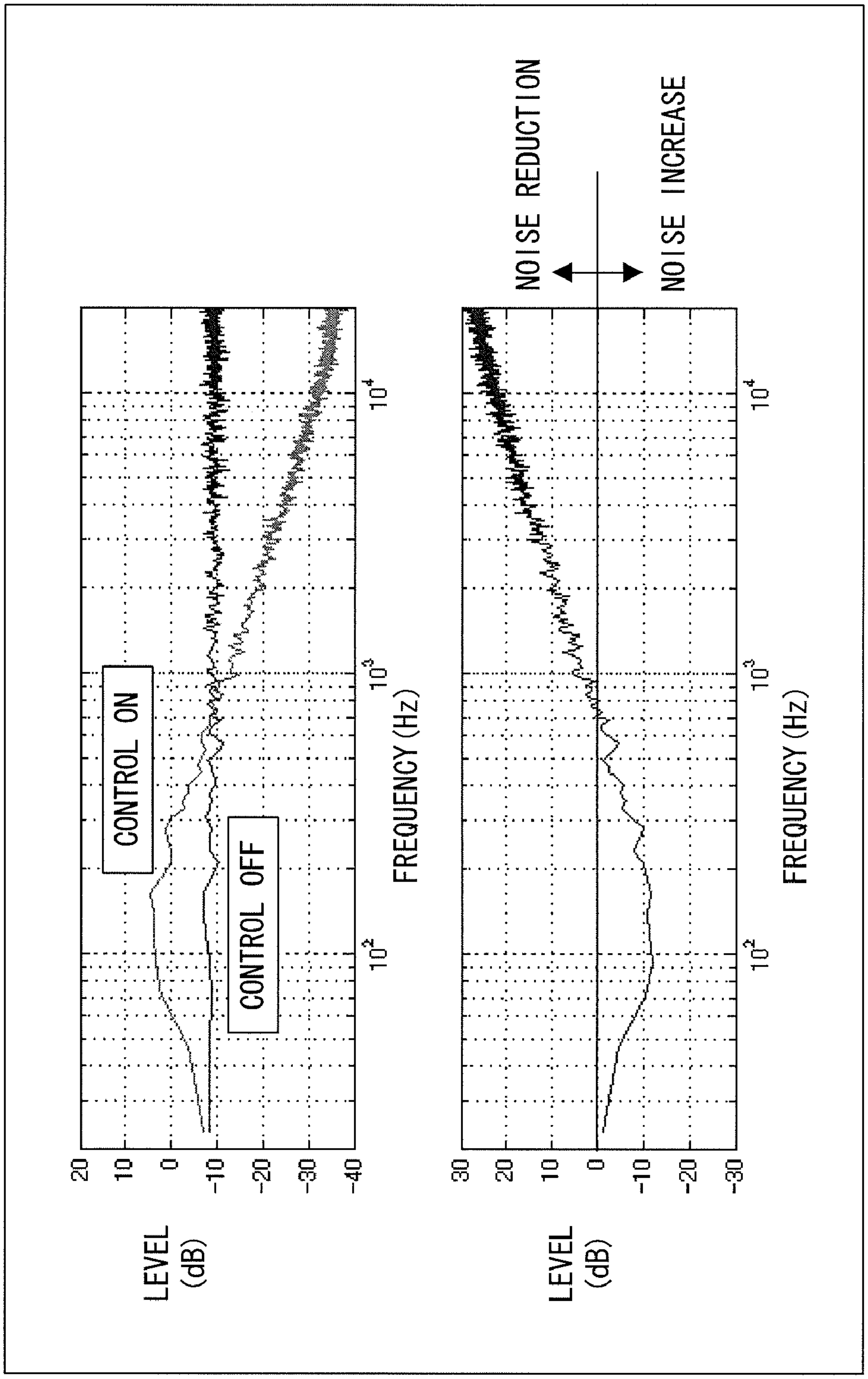
FIG. 30 shows a noise reduction effect at the control point 4 in a case where the FIR filter 600 (when the number of taps is small) shown in FIG. 24 is operated.

The characteristics of the signal processor 300 of FIG. 1 thus obtained, and the characteristics of the output correction section 500 of FIG. 1 thus obtained are synthesized, and approximated by a coefficient of the FIR filter 600 of FIG. 24. FIG. 28 shows characteristics of the FIR filter 600 shown in FIG. 24. The number of taps of the FIR filter 600 is 107571. FIG. 29 shows a noise reduction effect of a noise control device that includes the FIR filter 600 having the characteristics shown in FIG. 28. It can be seen that the noise reduction effect shown in FIG. 29 is substantially equal to the noise reduction effect shown in FIG. 27. Since the number of taps of the FIR filter 600 is 107571, which is large, the noise reduction effect as shown in FIG. 29 is obtained. However, conversely, when the number of taps of the FIR filter 600 is made small, the noise reduction effect deteriorates. FIG. 30 shows a noise reduction effect in a case where the number of taps of the FIR filter 600 is made small. In FIG. 30, the larger the improvement of the effect which results from the correction performed by the output correction section 500 is, the more significant the deterioration of the noise reduction effect becomes. A cause of the deterioration of the noise reduction effect is that the FIR filter 600 of FIG. 24 performs a finite response while the output correction section 500 of FIG. 1 is a feedback system and therefore performs an infinite response.

In this manner, it is possible to synthesize the characteristics of the signal processor 300 of FIG. 1 and the characteristics of the output correction section 500 of FIG. 1, and to represent the characteristics resulting from the synthesis as a coefficient of the FIR filter 600 of FIG. 24. However, it is necessary to increase the number of taps of the FIR filter 600, and resultantly, the amount of operations can be made smaller when the output correction section 500 using the feedback system in FIG. 1 is used.

As described above, the noise control device according to the first embodiment of the present invention can reduce a noise in a frequency band for which the noise control process can be performed within the noise transfer time while suppressing a noise increase in a frequency band for which the noise control process cannot be performed within the noise transfer time.

Second Embodiment

Figure 31:
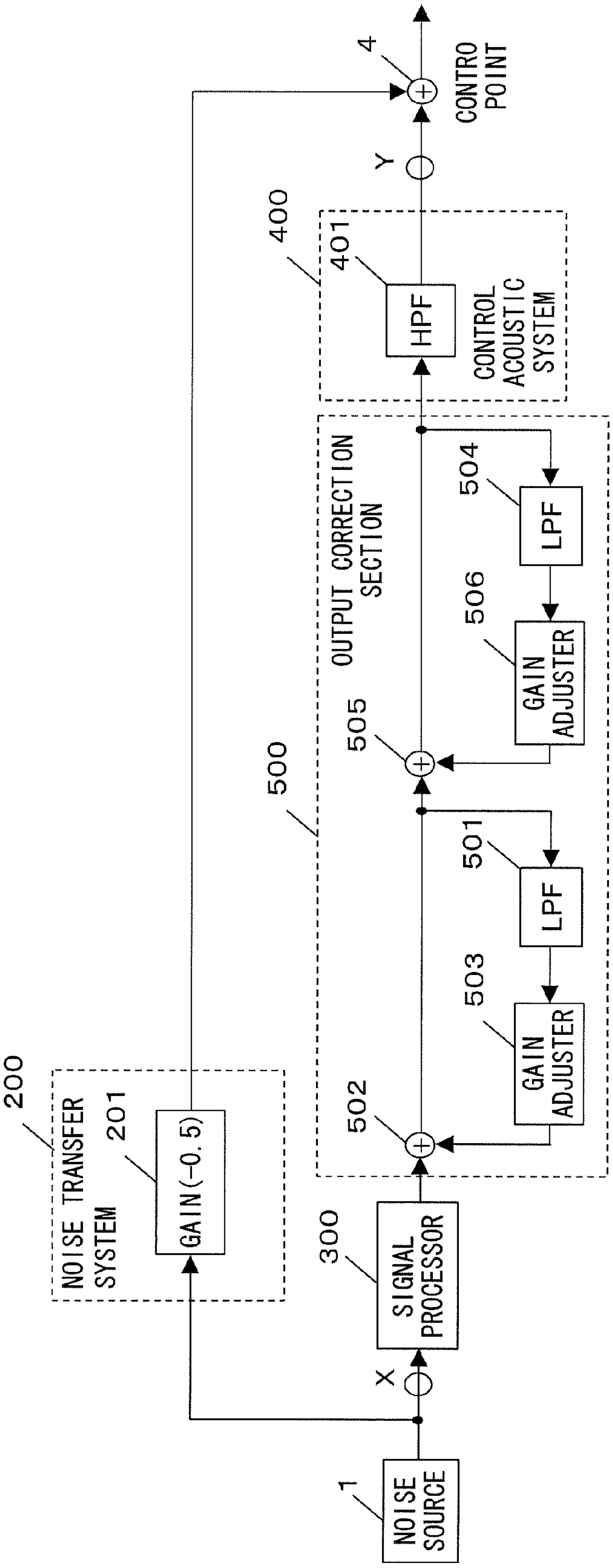
FIG. 31 shows a circuit configuration of a noise control device according to a second embodiment.

In the present embodiment, a case where the output correction section of the noise control device described in the first embodiment includes a plurality of positive feedback sections will be described. FIG. 31 shows a circuit configuration of a noise control device according to the second embodiment.

Figure 32:
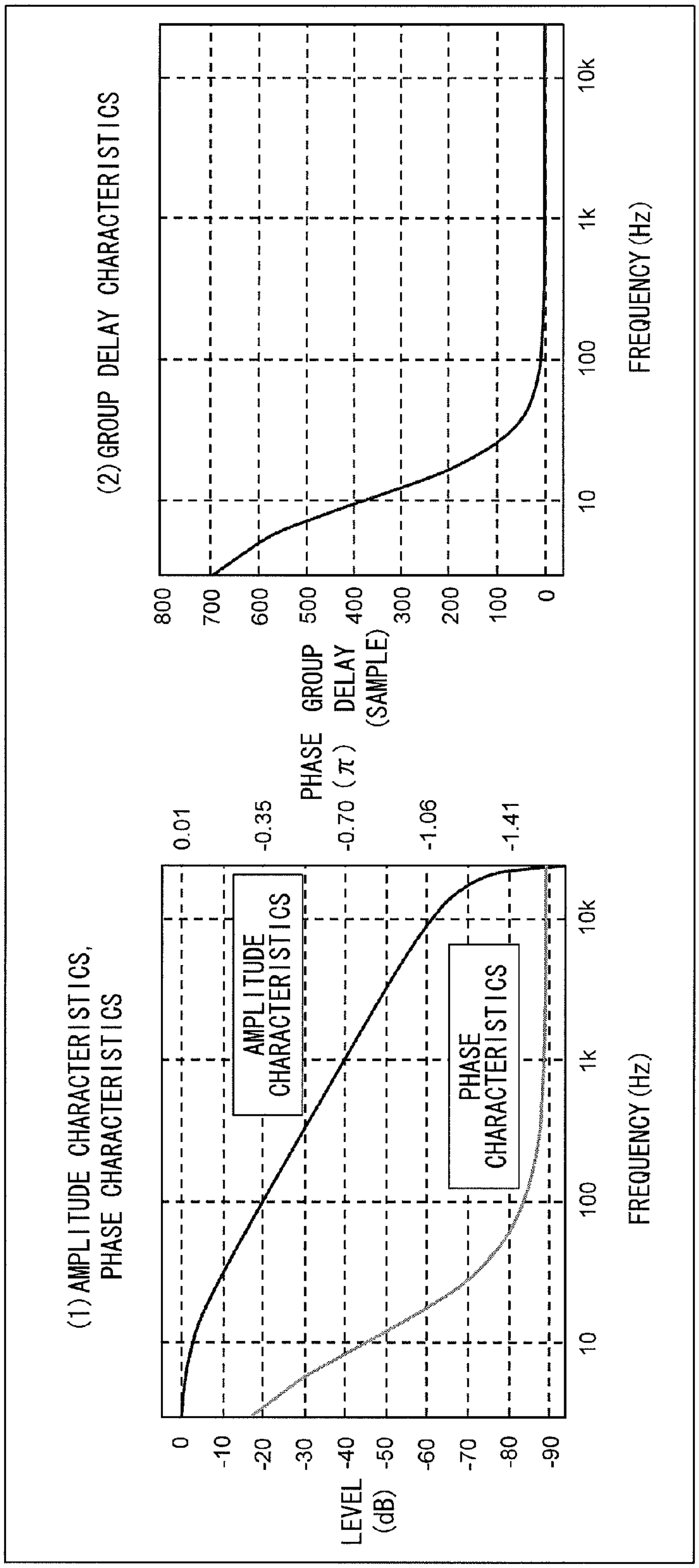
FIG. 32 shows characteristics of a LPF 501 of an output correction section 500 shown in FIG. 31.
Figure 33:
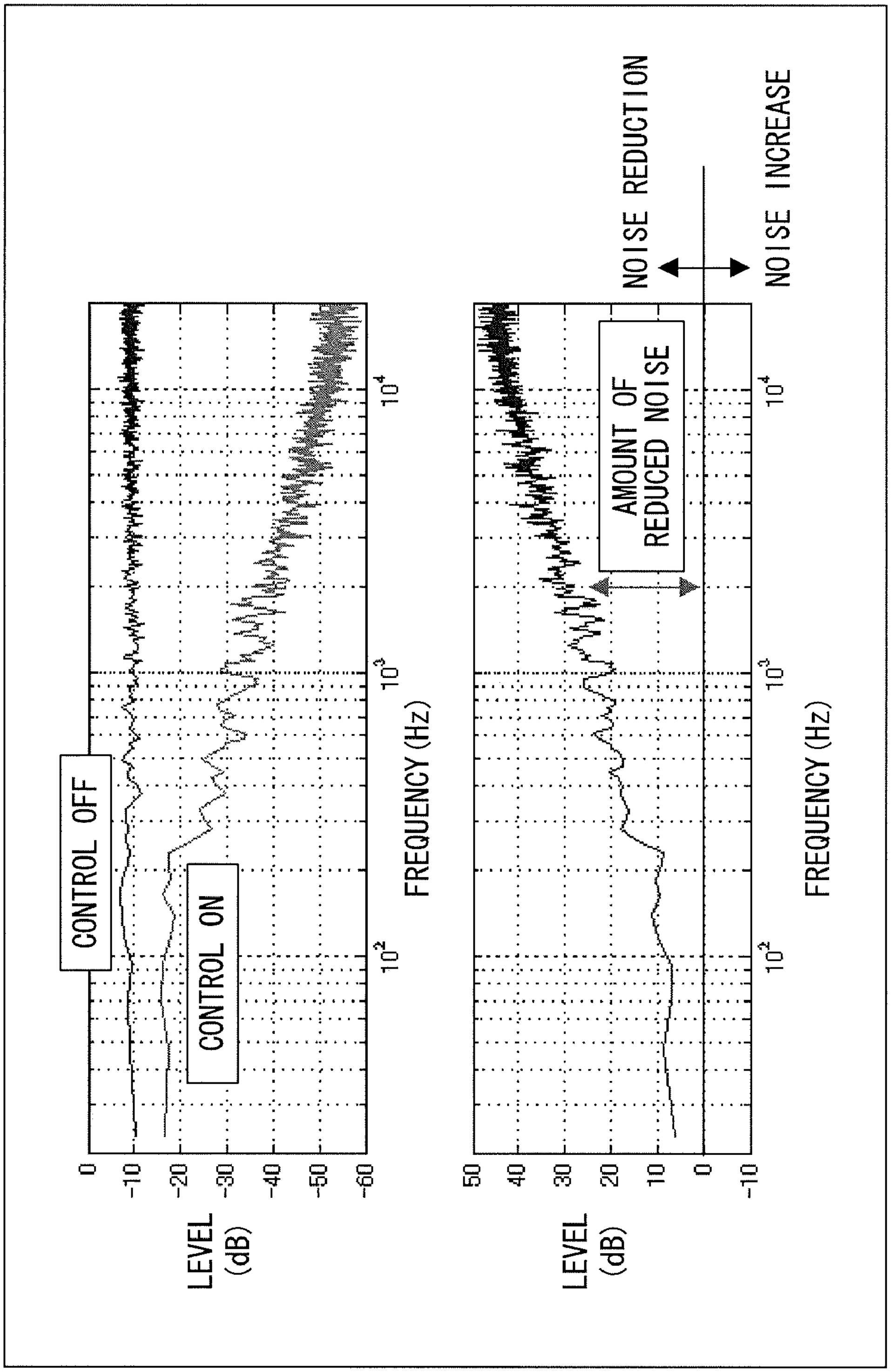
FIG. 33 shows a noise reduction effect at a control point 4 in a case where the output correction section 500 (the characteristics of FIGS. 4 and 32) shown in FIG. 31 is operated.
Figure 34:
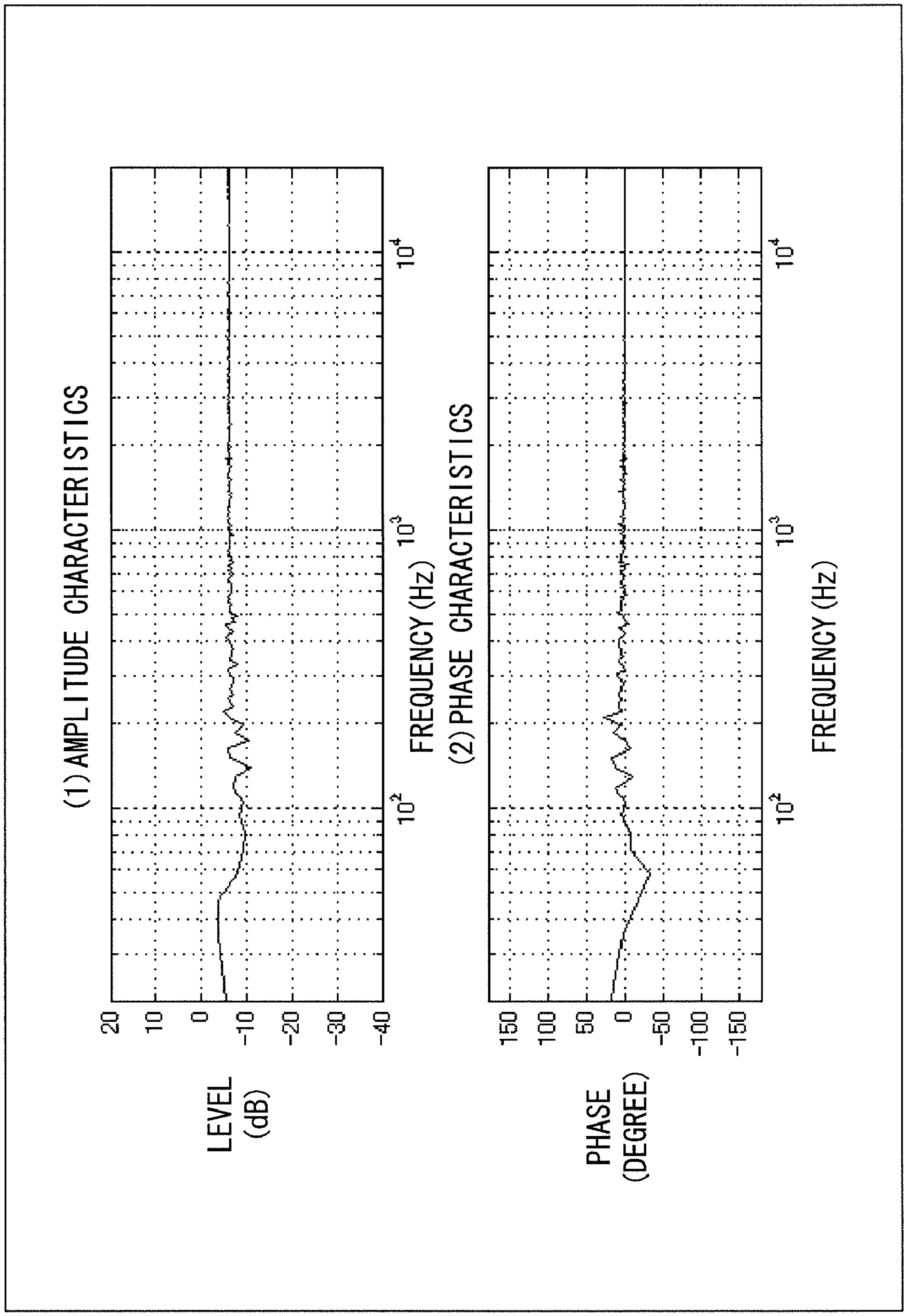
FIG. 34 shows transfer characteristics for transfer from the point X to the point Y in a case where the output correction section 500 (the characteristics of FIGS. 4 and 32) shown in FIG. 31 is operated.

As shown in FIG. 31, an output correction section 500 forms two feedback sections in series, by using LPFs 501 and 504, adders 502 and 505, and gain adjusters 503 and 506. Here, the second-order LPF having a resonant frequency fc=90 Hz shown in FIG. 4 is applied to the LPF 501, and a first-order LPF having a resonant frequency fc=10 Hz shown in FIG. 32 is applied to the LPF 504. In addition, appropriate positive values are set in the gain adjusters 503 and 506, and positive feedbacks are performed. A noise reduction effect obtained at this time is as shown in FIG. 33. In FIG. 33, at a frequency equal to or higher than 100 Hz, a noise reduction effect equivalent to that in FIG. 5 is maintained, while at a frequency equal to or lower than 70 Hz, a noise reduction effect is improved as compared with in FIG. 5. Transfer characteristics for transfer from a point X to a point Y of the noise control device shown in FIG. 31 are as shown in FIG. 34. In FIG. 34, amplitude characteristics are equivalent to those in FIG. 9, and phase characteristics are, at a frequency equal to or lower than 30 Hz, closer to zero degrees than in FIG. 9. That is, when the first-order LPFs having a resonant frequency fc=10 Hz are used in series in the output correction section 500, a noise reduction effect in a lower range can be improved, as compared with in the case of FIGS. 1 and 5 in which the second-order LPF having a resonant frequency fc=90 Hz is singularly used.

Figure 35:
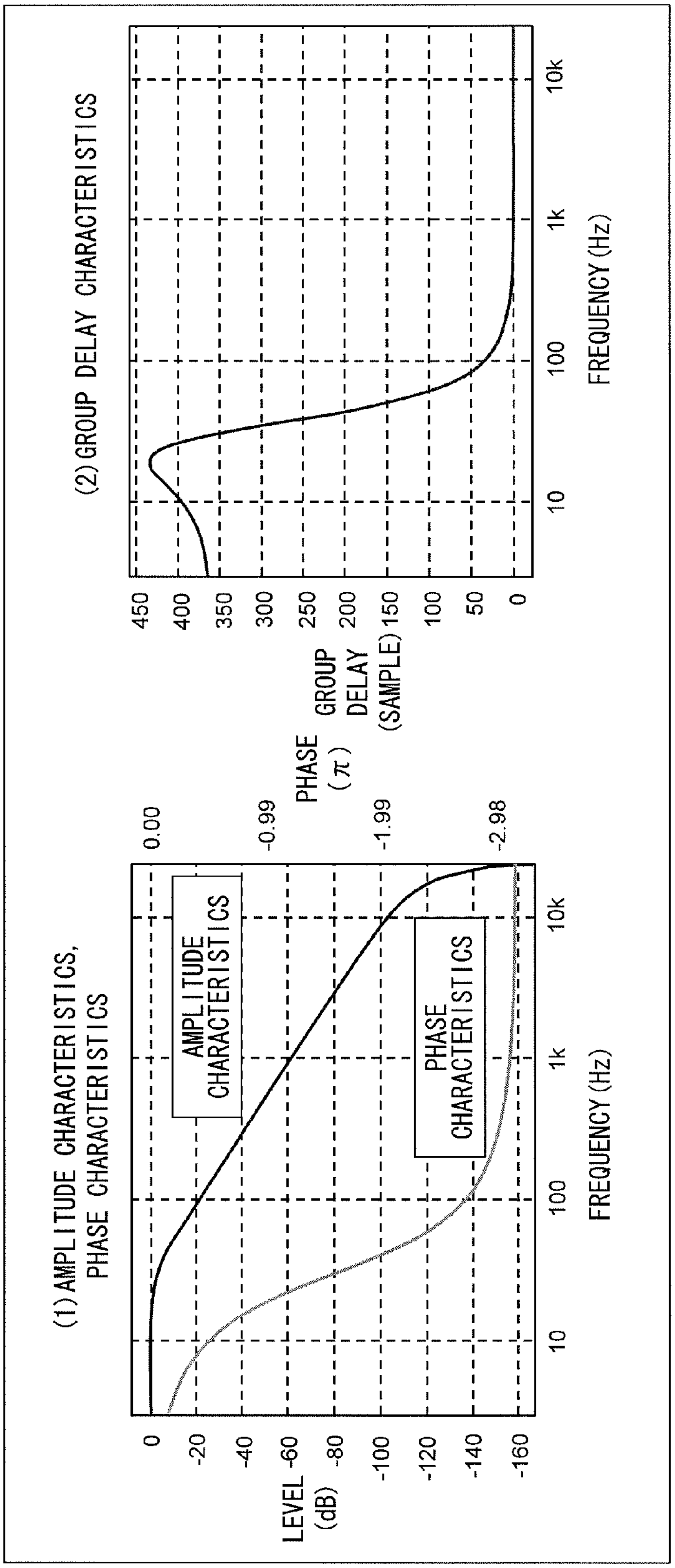
FIG. 35 shows other characteristics of the LPF 501 of the output correction section 500 shown in FIG. 31.
Figure 36:
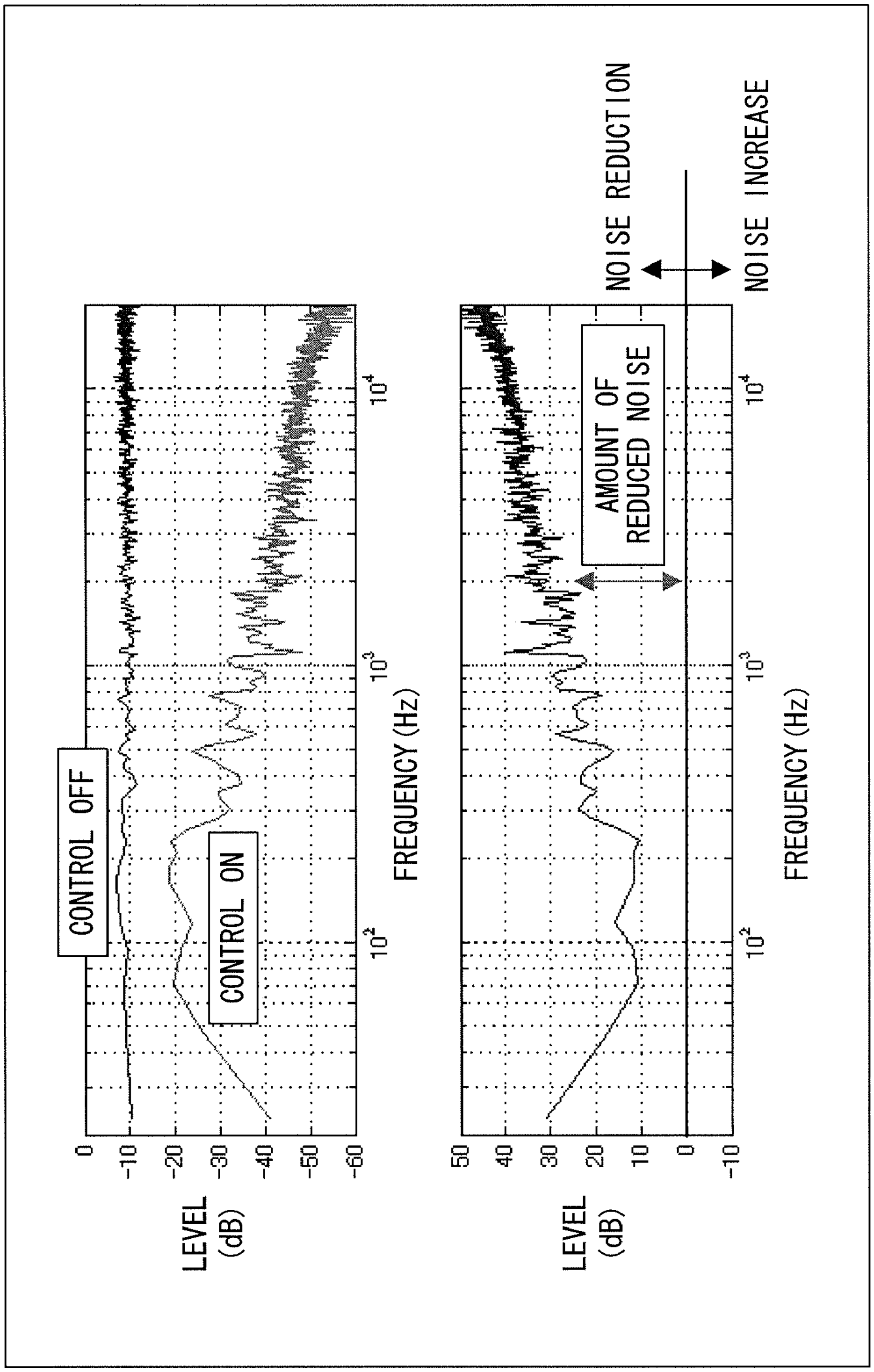
FIG. 36 shows a noise reduction effect at the control point 4 in a case where the output correction section 500 (the characteristics of FIGS. 10 and 35) shown in FIG. 31 is operated.
Figure 37:
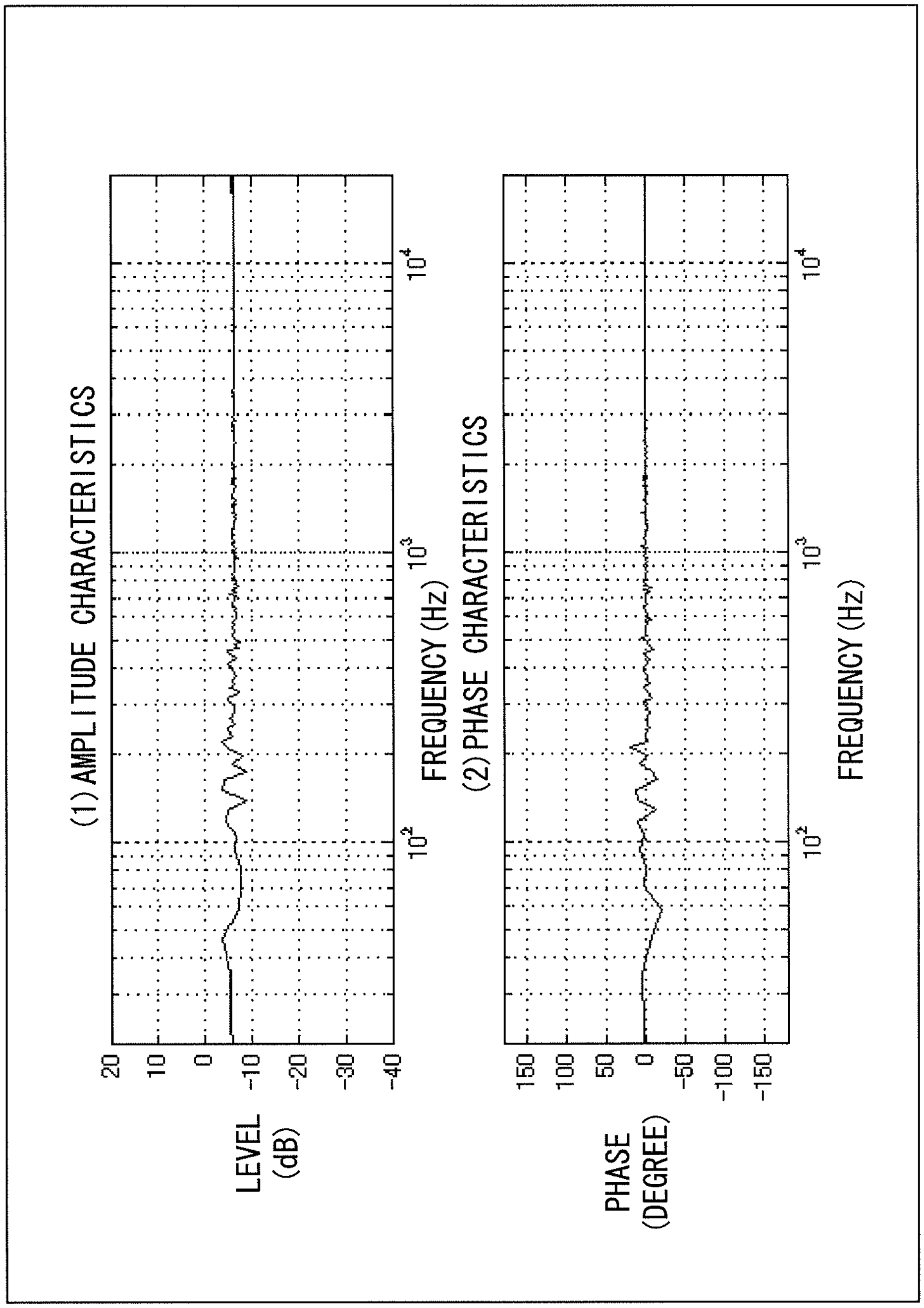
FIG. 37 shows transfer characteristics for transfer from the point X to the point Y in a case where the output correction section 500 (the characteristics of FIGS. 10 and 35) shown in FIG. 31 is operated.

As an example of setting other characteristics to the LPFs 501 and 503 of FIG. 31, the first-order LPF having a resonant frequency fc=60 Hz shown in FIG. 10 is applied to the LPF 501, and a second-order LPF having a resonant frequency fc=30 Hz shown in FIG. 35 is applied to the LPF 503. A noise reduction effect obtained at this time is as shown in FIG. 36. In FIG. 36, at a frequency equal to or higher than 100 Hz, a noise reduction effect equivalent to that in FIG. 11 is maintained, while at a frequency equal to or lower than 100 Hz, a noise reduction effect is largely improved as compared with in FIG. 11. The transfer characteristics for transfer from the point X to the point Y of the noise control device shown in FIG. 31 are as shown in FIG. 37. In FIG. 37, amplitude characteristics are equivalent to those in FIG. 12, and phase characteristics are, at a frequency equal to or lower than 40 Hz, closer to zero degrees than in FIG. 12. That is, when the second-order LPFs having a resonant frequency fc=30 Hz are used in series in the output correction section 500, a noise reduction effect in a lower range can be improved, as compared with in the case of FIGS. 1 and 11 in which the first-order LPF having a resonant frequency fc=60 Hz is singularly used.

Third Embodiment

Figure 38:
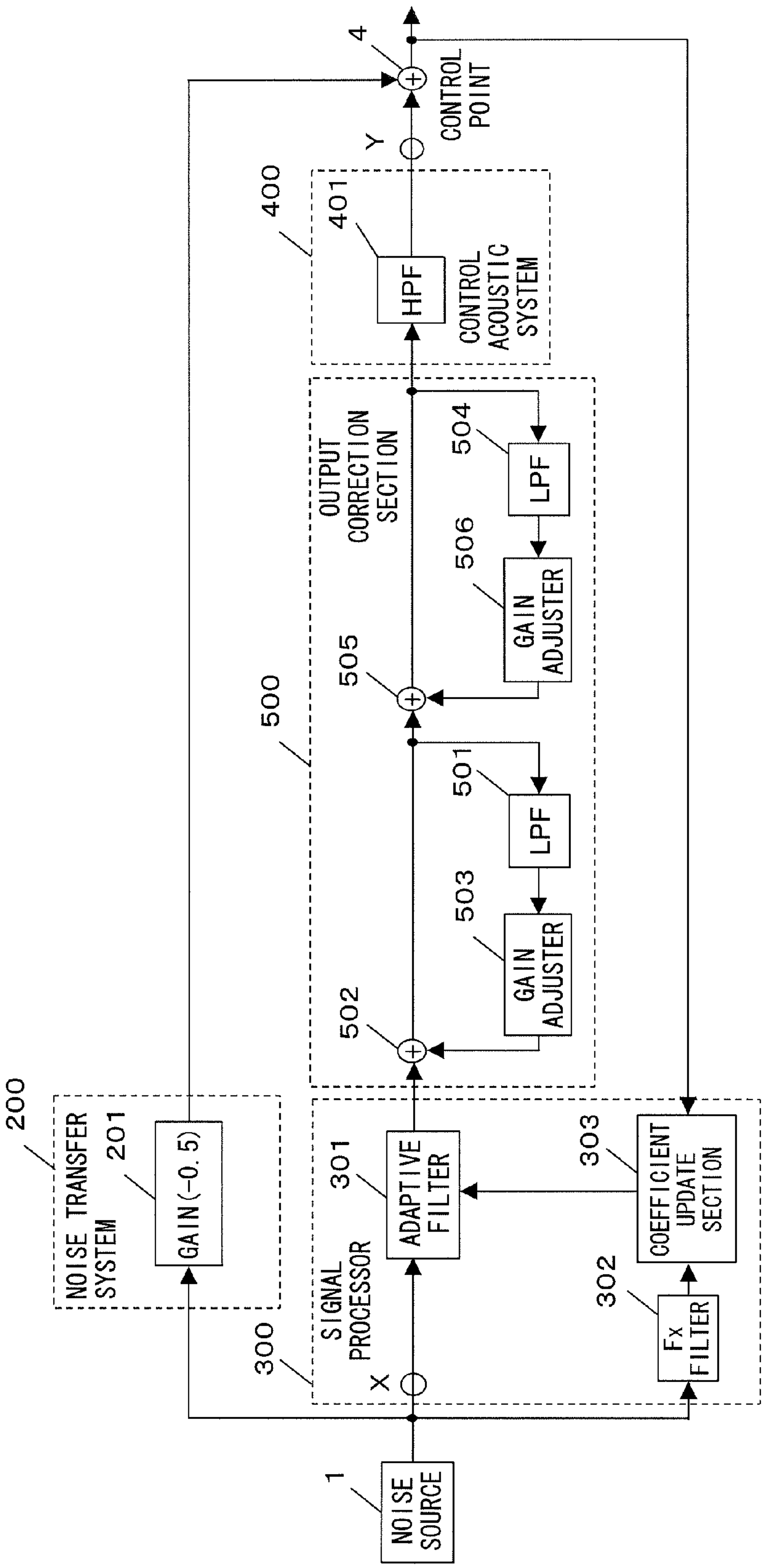
FIG. 38 shows a circuit configuration of a noise control device according to a third embodiment.

In the present embodiment, a case where the signal processor of the noise control device described in the second embodiment is operated as an adaptive filter will be described. FIG. 38 shows a circuit configuration of a noise control device according to the third embodiment. In FIG. 38, the noise control device according to the third embodiment includes an adaptive filter 301 in a signal processor 300.

Figure 39:
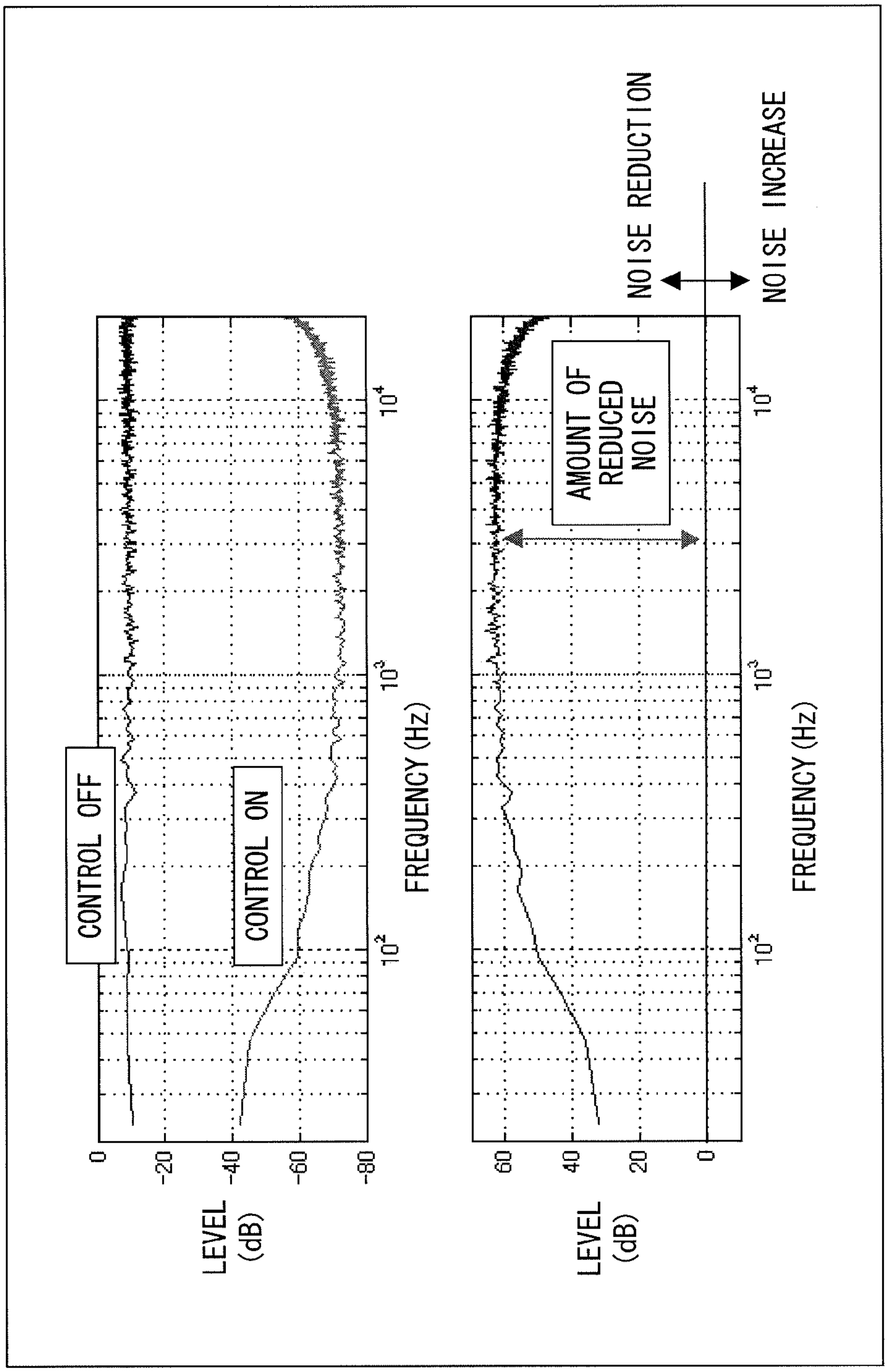
FIG. 39 shows a noise reduction effect of the noise control device shown in FIG. 38.

In FIG. 38, the adaptive filter 301 performs a signal process on a noise signal outputted from the noise source 1, and outputs a resultant signal, as a control signal, to the output correction section 500. The control signal corrected by the output correction section 500 reaches the control point 4 via the control acoustic system 400. At the control point 4, a noise transmitted from the noise source 1 through the noise transfer system 200 and a control sound outputted from the control acoustic system 400 are added, and a resultant sound is, as an error signal, inputted to a coefficient update section 303. Here, characteristics (a coefficient) of an Fx filter 302 of the signal processor 300 approximate to the characteristics obtained by synthesizing the characteristics of the output correction section 500 and the characteristics of the control acoustic system 400. Alternatively, the same process as in the output correction section 500 may be formed in the Fx filter 302, and a filter having characteristics that approximate to the characteristics of the control acoustic system 400 may be connected in series. Then, based on an output signal outputted from the Fx filter 302 and the error signal outputted from the control point 4, the coefficient update section 303 updates a coefficient of the adaptive filter 301 such that the error signal can be Minimized. Thereby, a noise at the control point 4 is reduced. FIG. 39 shows a noise reduction effect of the noise control device shown in FIG. 38. Here, the first-order LPF having a resonant frequency fc=60 Hz shown in FIG. 10 is applied to the LPF 501 of the output correction section 500, and the second-order LPF having a resonant frequency fc=30 Hz shown in FIG. 35 is applied to the LPF 503. Comparing FIG. 39 and FIG. 36, the noise reduction effect is largely improved in FIG. 39.

Figure 40:
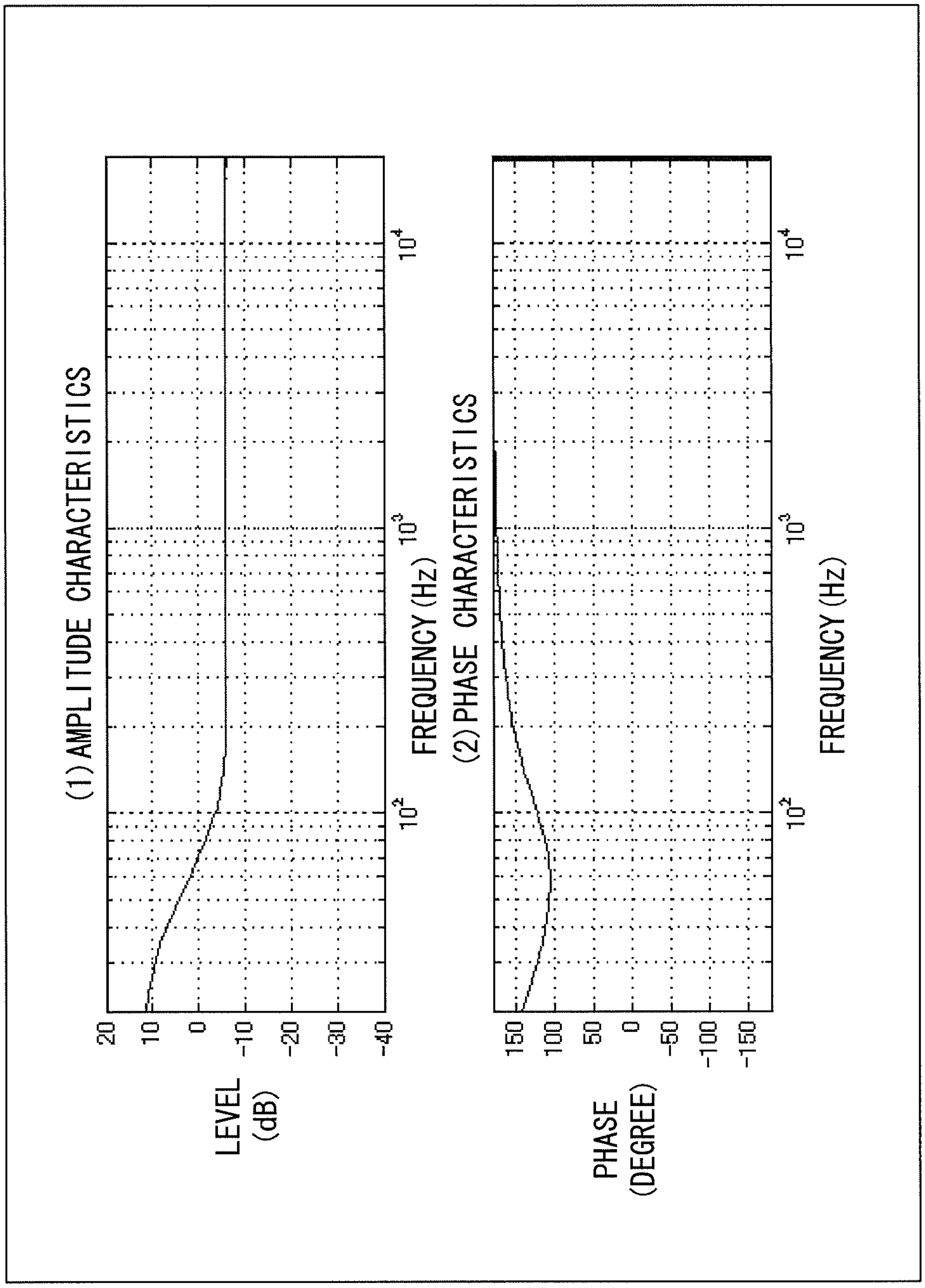
FIG. 40 shows characteristics (a coefficient) of an adaptive filter 301 of the noise control device shown in FIG. 38.
Figure 41:
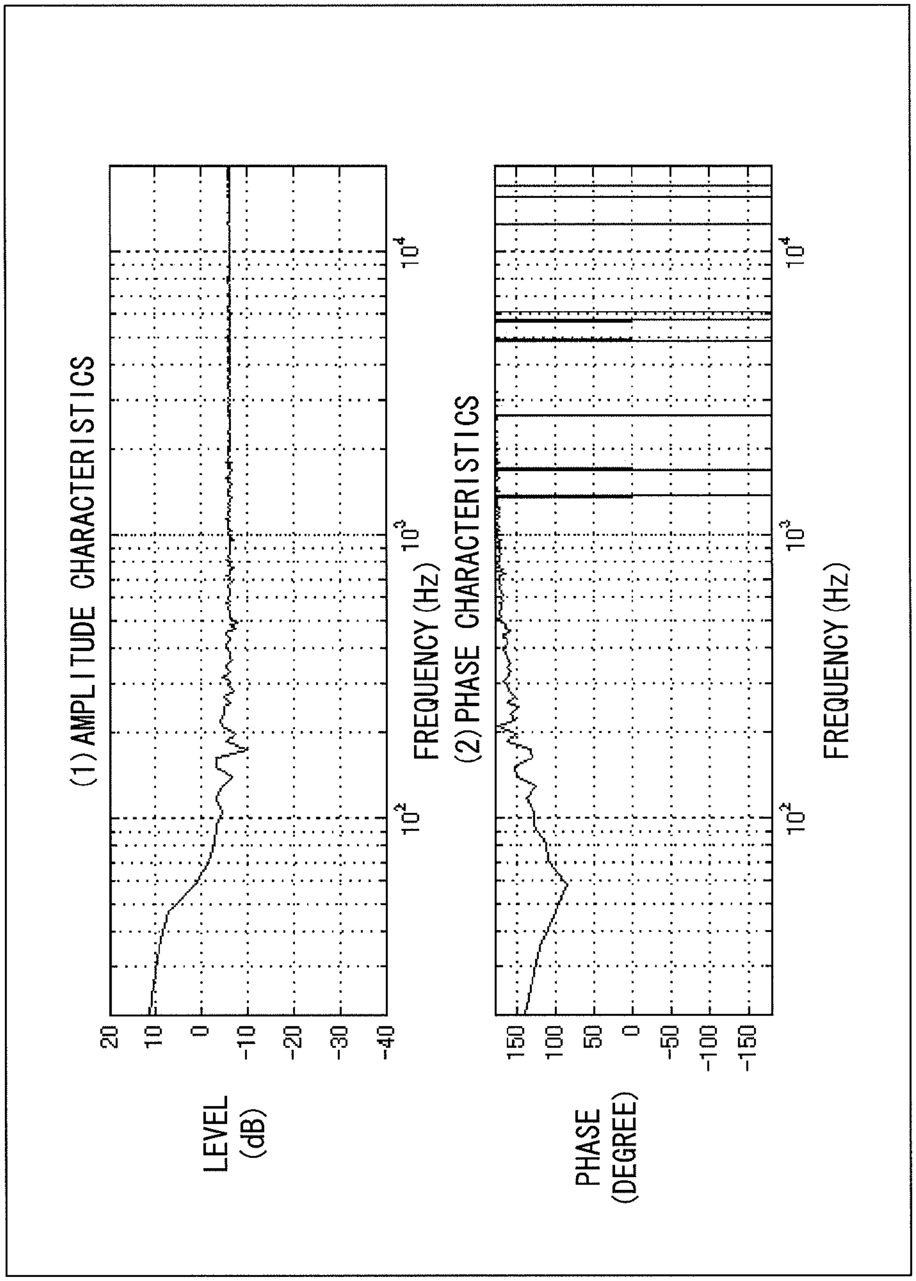
FIG. 41 shows characteristics (a coefficient) of a signal processor 300 of the noise control device shown in FIG. 31.

Here, FIG. 40 shows characteristics (a coefficient) of the adaptive filter 301 of the noise control device shown in FIG. 38. By using the adaptive filter 301 having the characteristics shown in FIG. 40, the noise control device shown in FIG. 38 can exhibit the noise reduction effect shown in FIG. 39. FIG. 41 shows characteristics (a coefficient) of the signal processor 300 of the noise control device shown in FIG. 31. By using the signal processor 300 having the characteristics shown in FIG. 41, the noise control device shown in FIG. 31 can exhibit the noise reduction effect shown in FIG. 34. Comparing FIG. 40 and FIG. 41, it can be seen that the characteristics shown in FIG. 40 are smoother.

Figure 42:
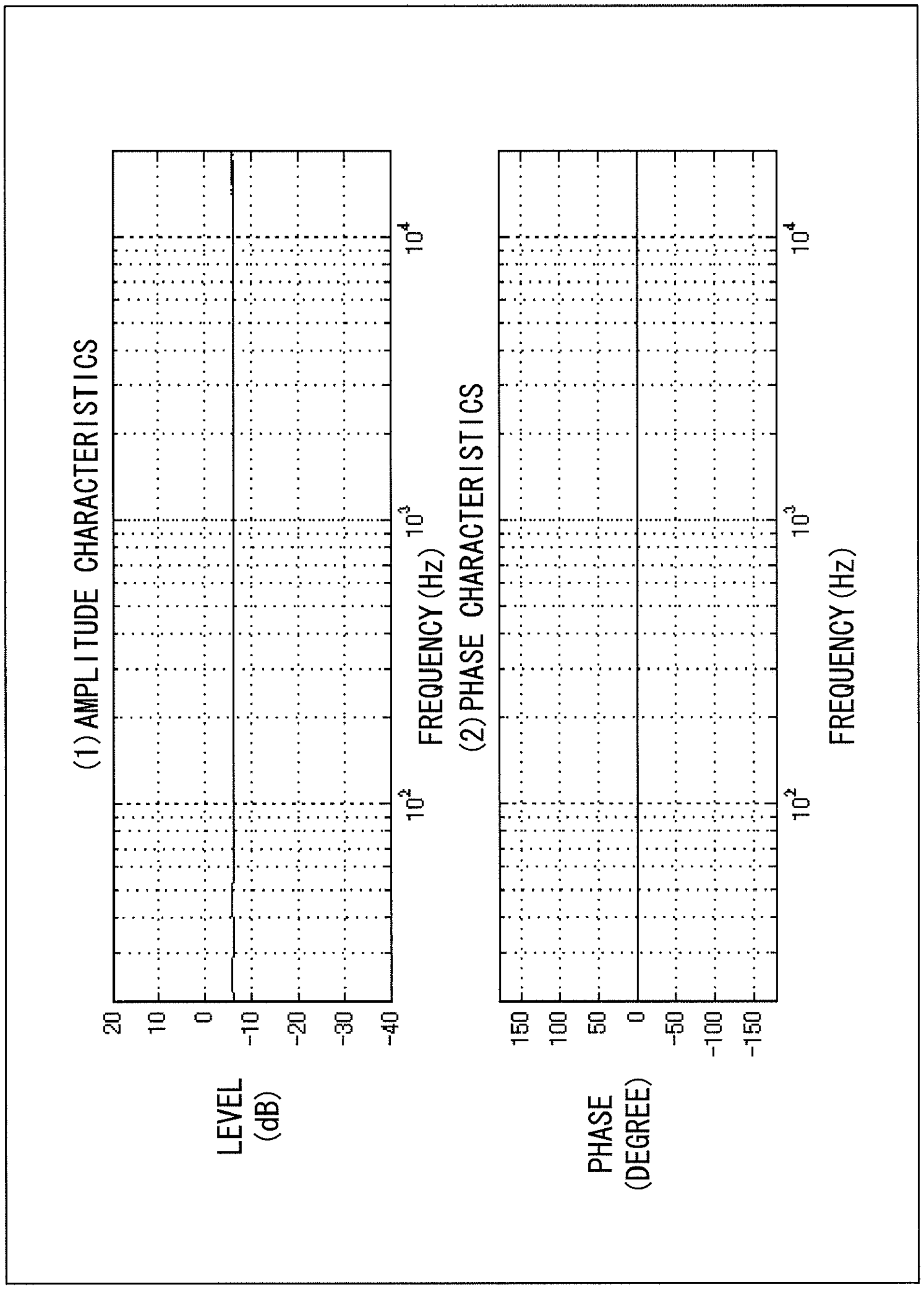
FIG. 42 shows transfer characteristics for transfer from the point X to the point Y of the noise control device shown in FIG. 38.
Figure 43:
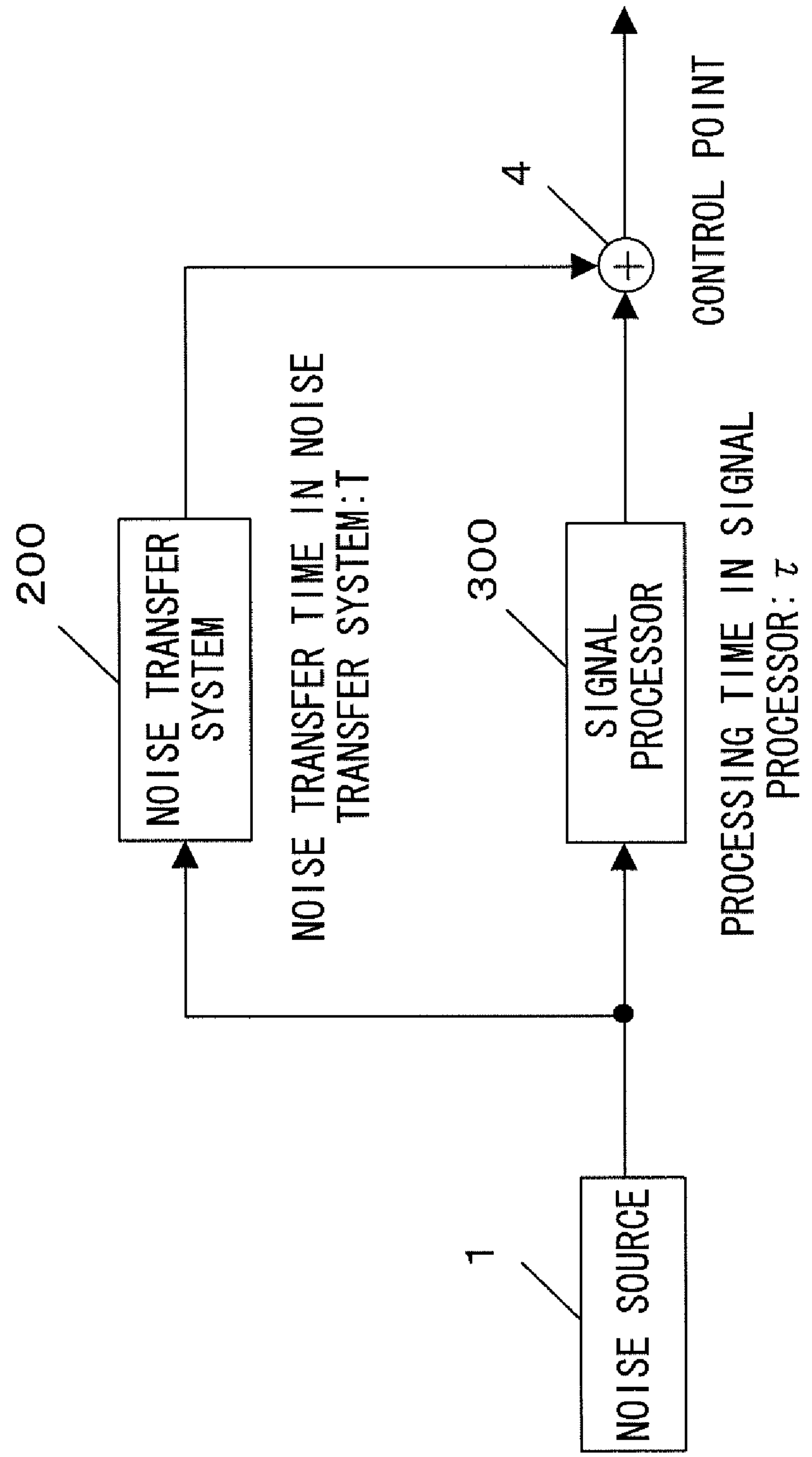
FIG. 43 PRIOR ART
FIG. 43 shows a fundamental configuration of a noise control device using an FF control.
Figure 44:
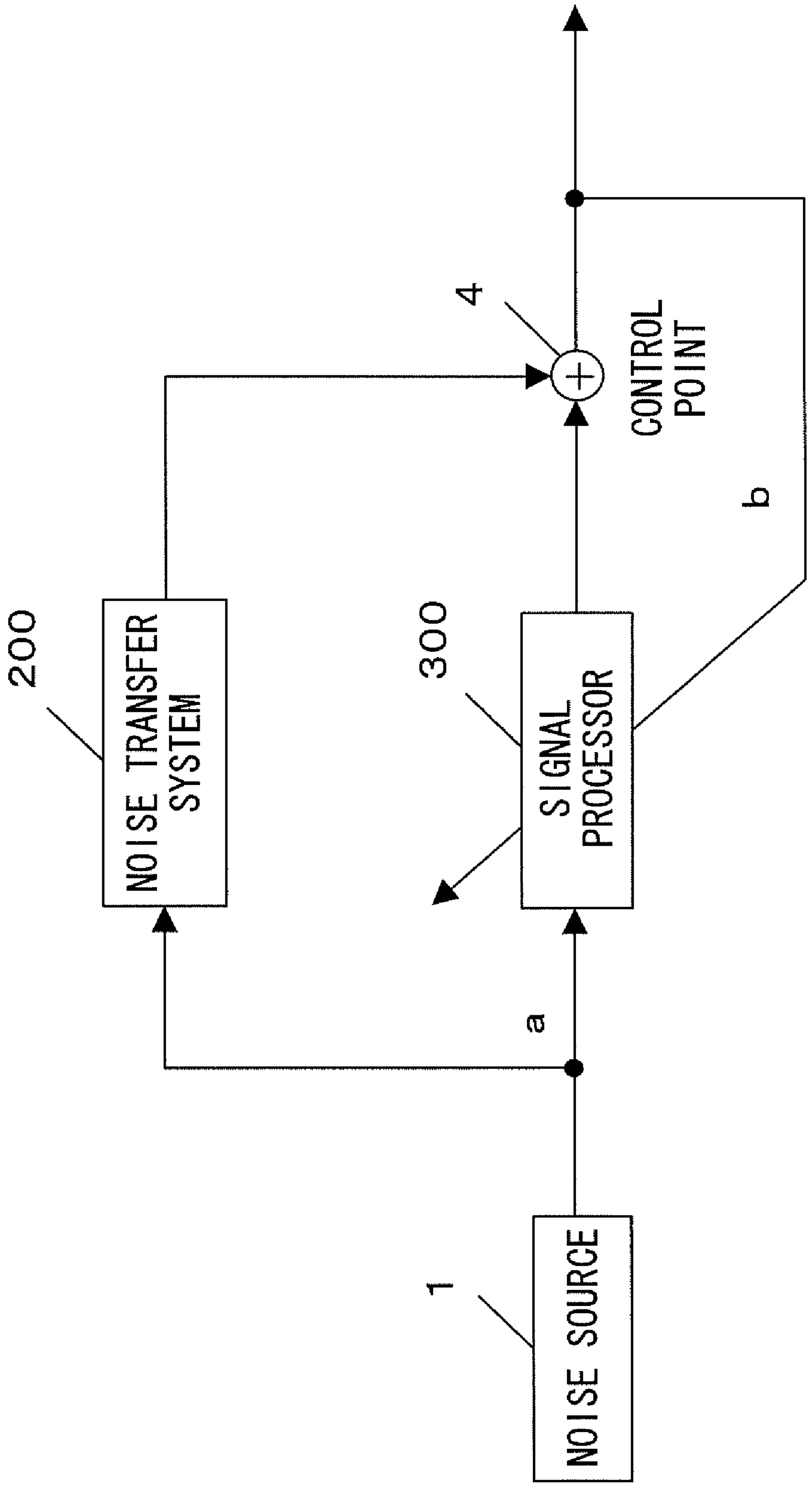
FIG. 44 PRIOR ART
FIG. 44 shows a fundamental configuration of a noise control device in a case where an adaptive FF control is used.
Figure 45:
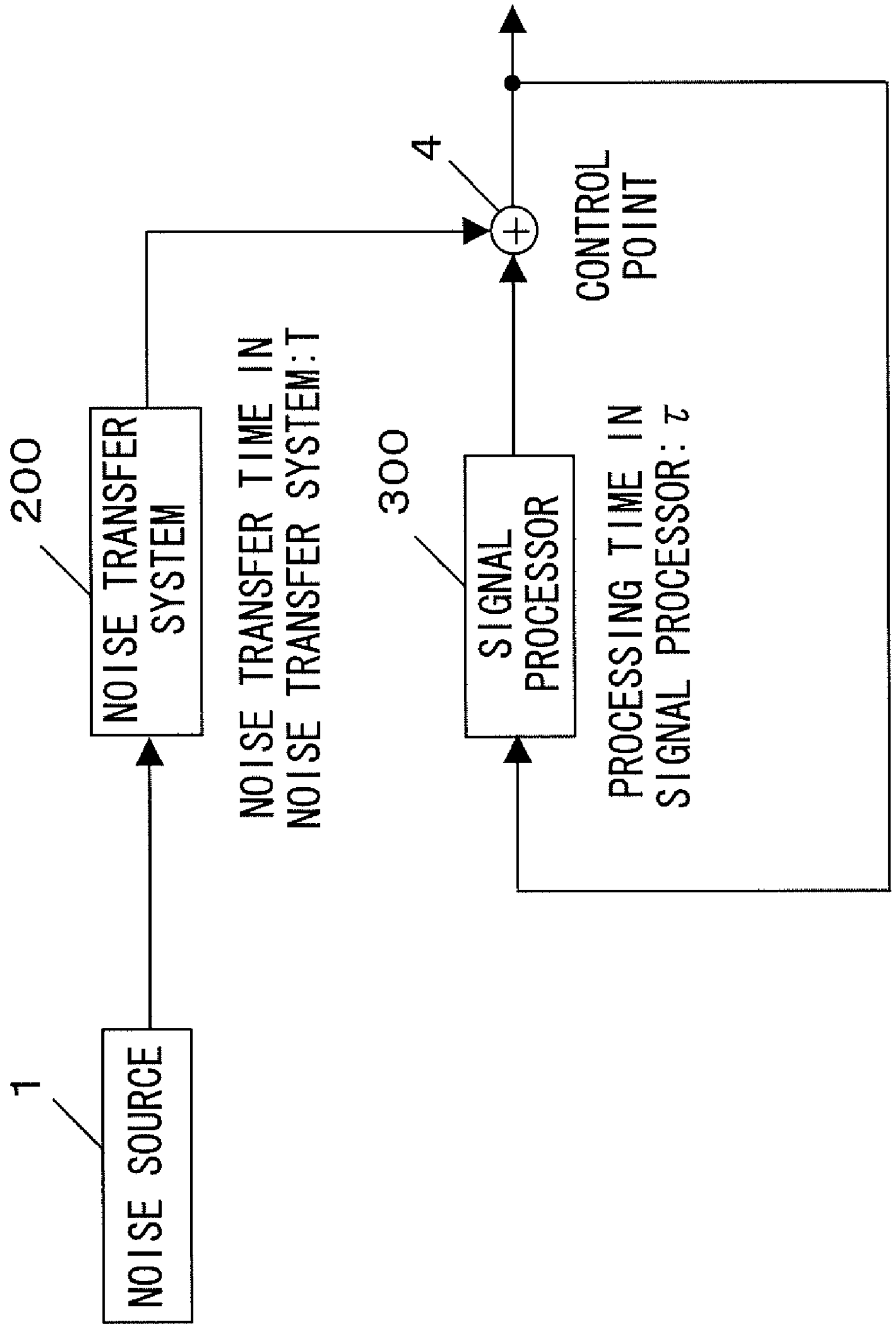
F I G. 4 5 PRIOR ART
FIG. 45 shows a fundamental configuration of a noise control device using an FB control.
Figure 46:
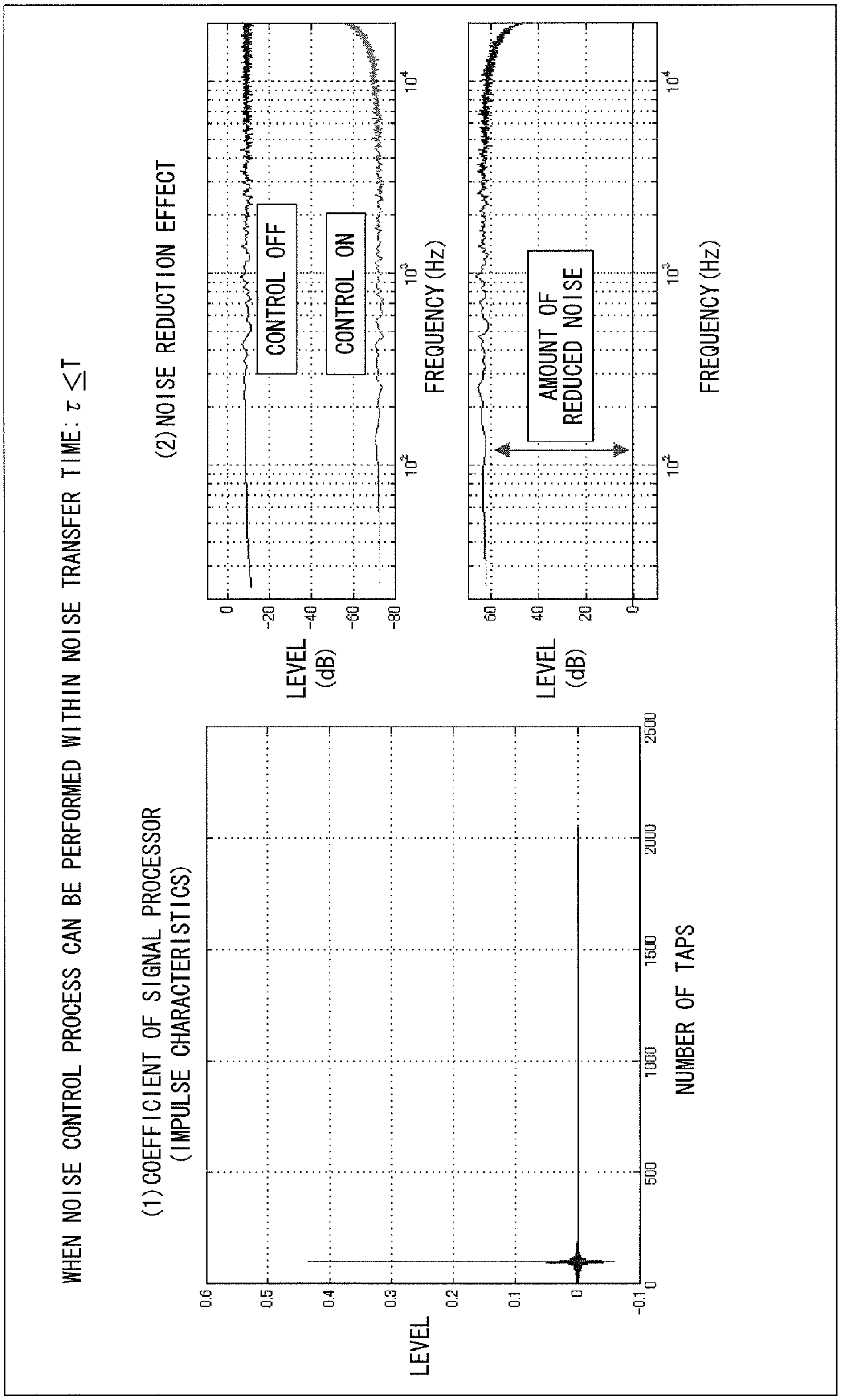
FIG. 46 PRIOR ART
FIG. 46 shows a coefficient of a signal processor 300 and a noise reduction effect at a control point 4, in a case where a noise control process in FIG. 43 or 44 can be performed within a noise transfer time.
Figure 47:
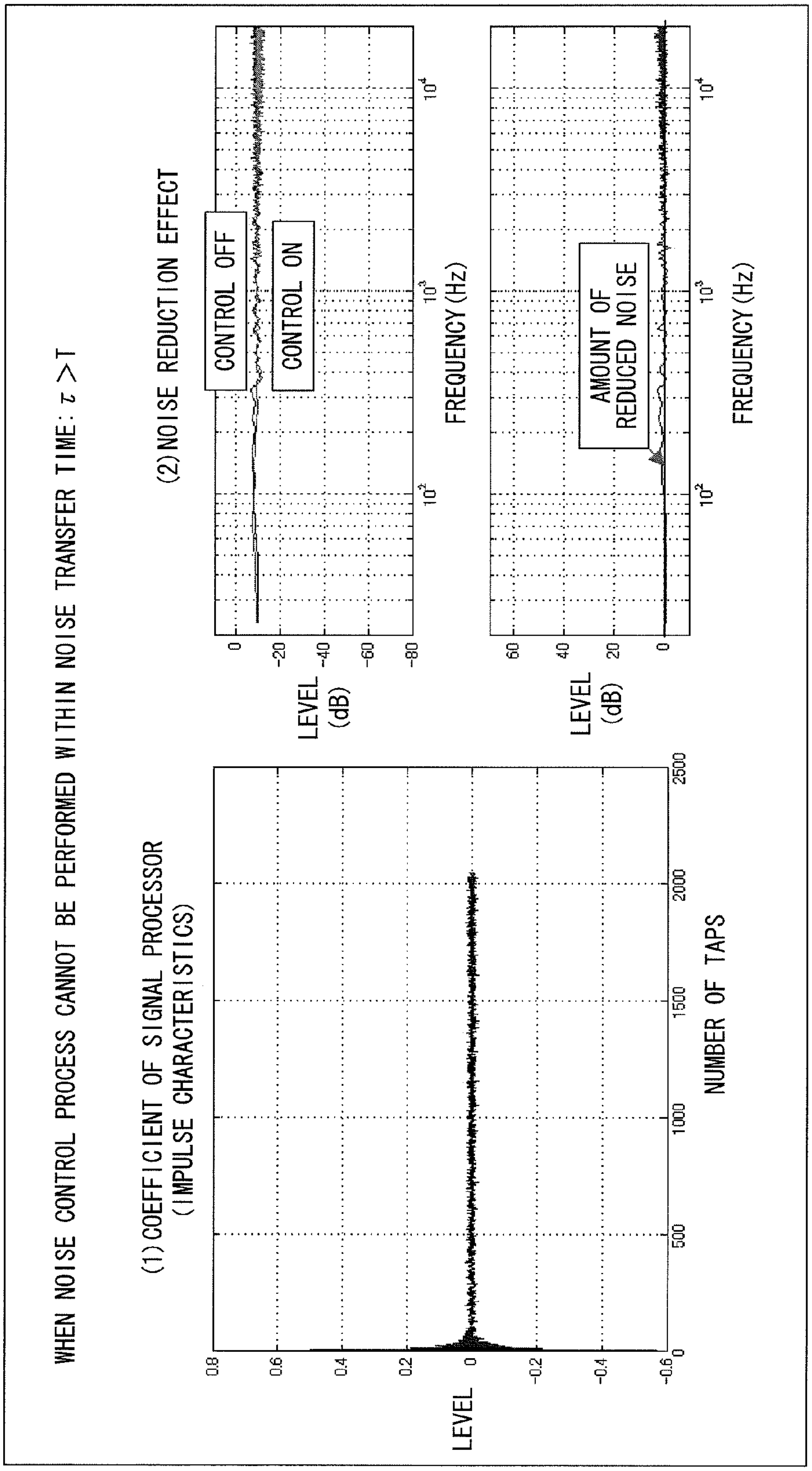
FIG. 47 PRIOR ART
FIG. 47 shows a coefficient of the signal processor 300 and a noise reduction effect at the control point 4, in a case where the noise control process in FIG. 43 or 44 cannot be performed within the noise transfer time.
Figure 48:
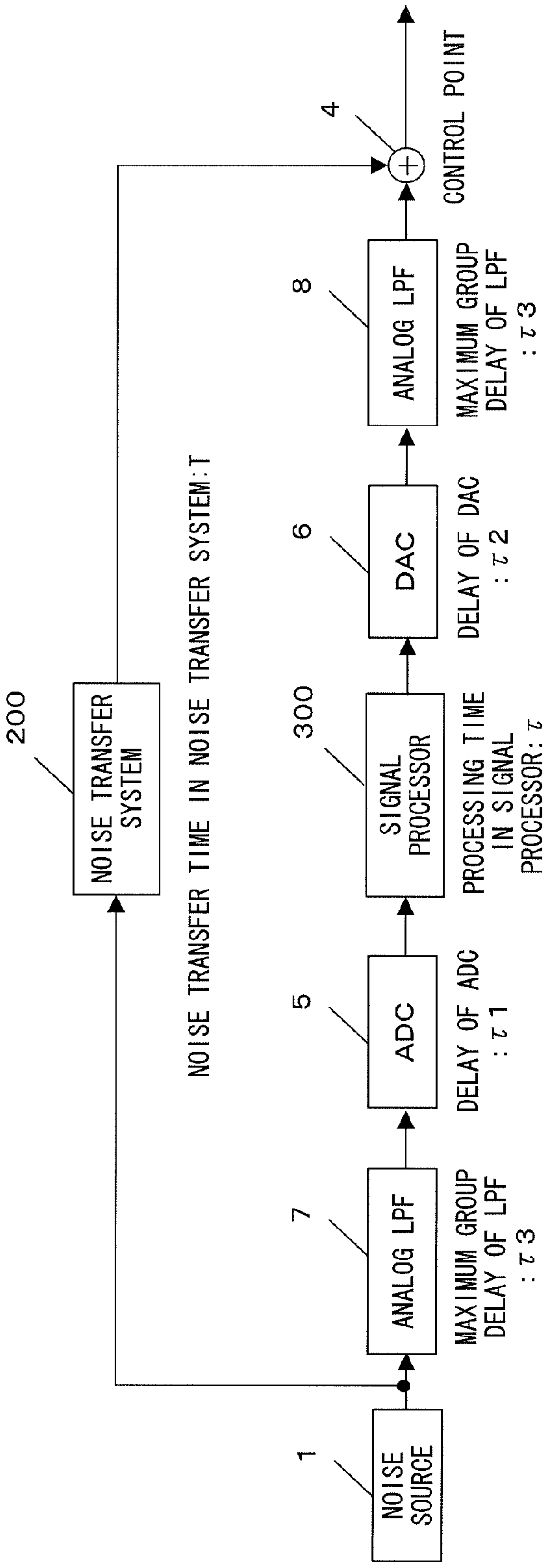
F I G. 4 8 PRIOR ART
FIG. 48 shows a re-description of the noise control device shown in FIG. 43, as a configuration in which an analog is mixed.
Figure 49:
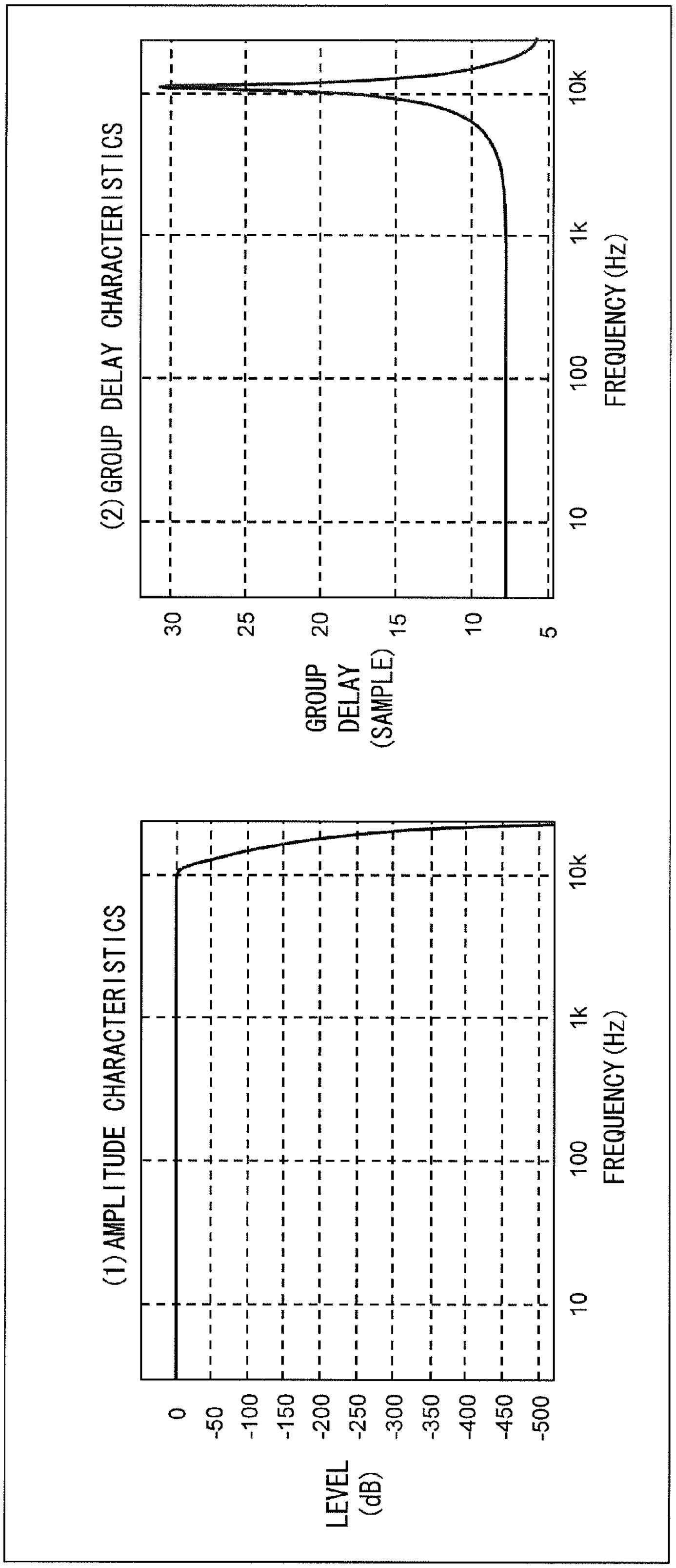
F I G. 4 9 PRIOR ART
FIG. 49 shows characteristics of analog LPFs 7 and 8 shown in FIG. 48.
Figure 50:
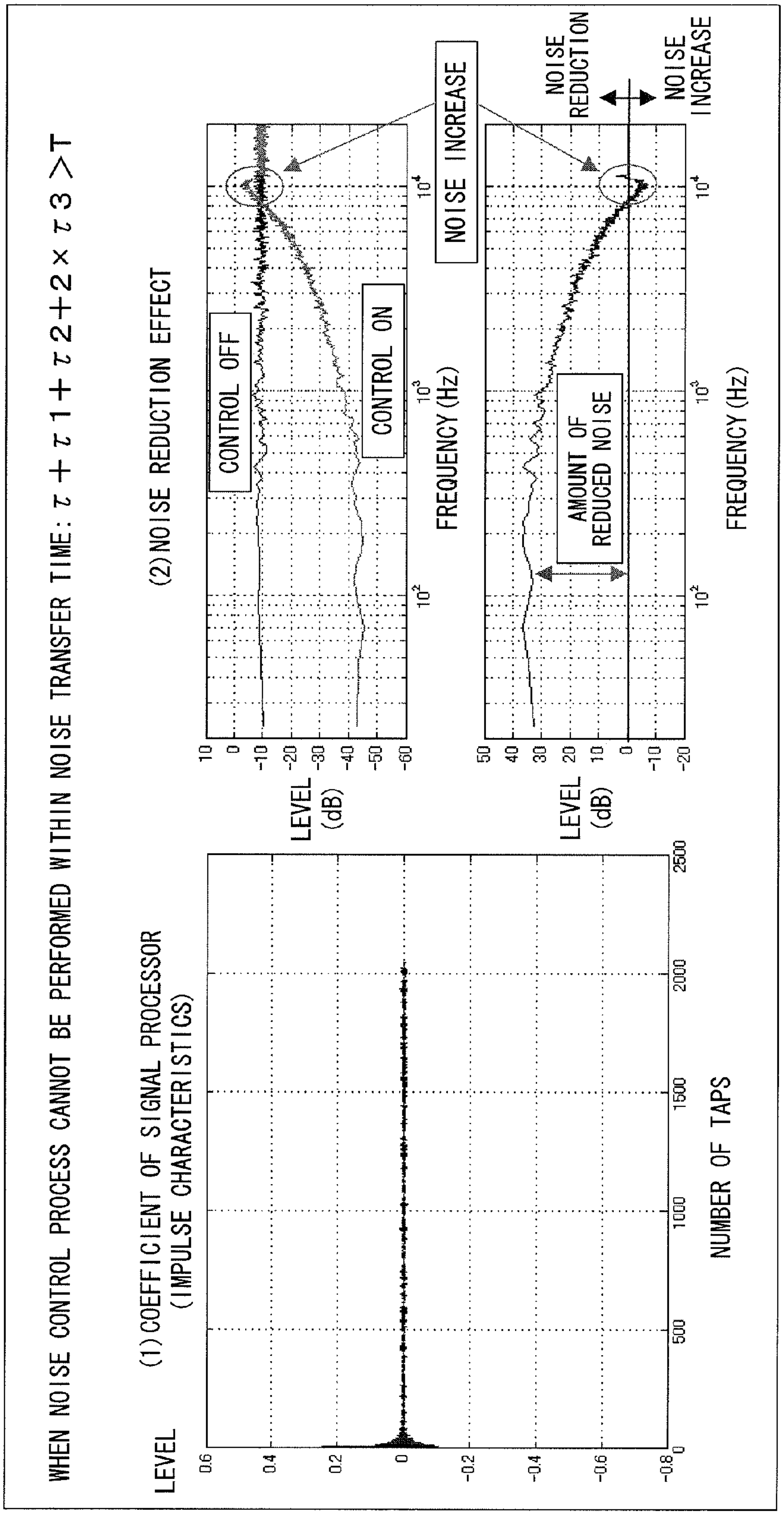
FIG. 50 PRIOR ART
FIG. 50 shows a coefficient of a signal processor 300 and a noise reduction effect at a control point 4, in a case where a noise control process in FIG. 48 cannot be performed within a noise transfer time.
Figure 51:
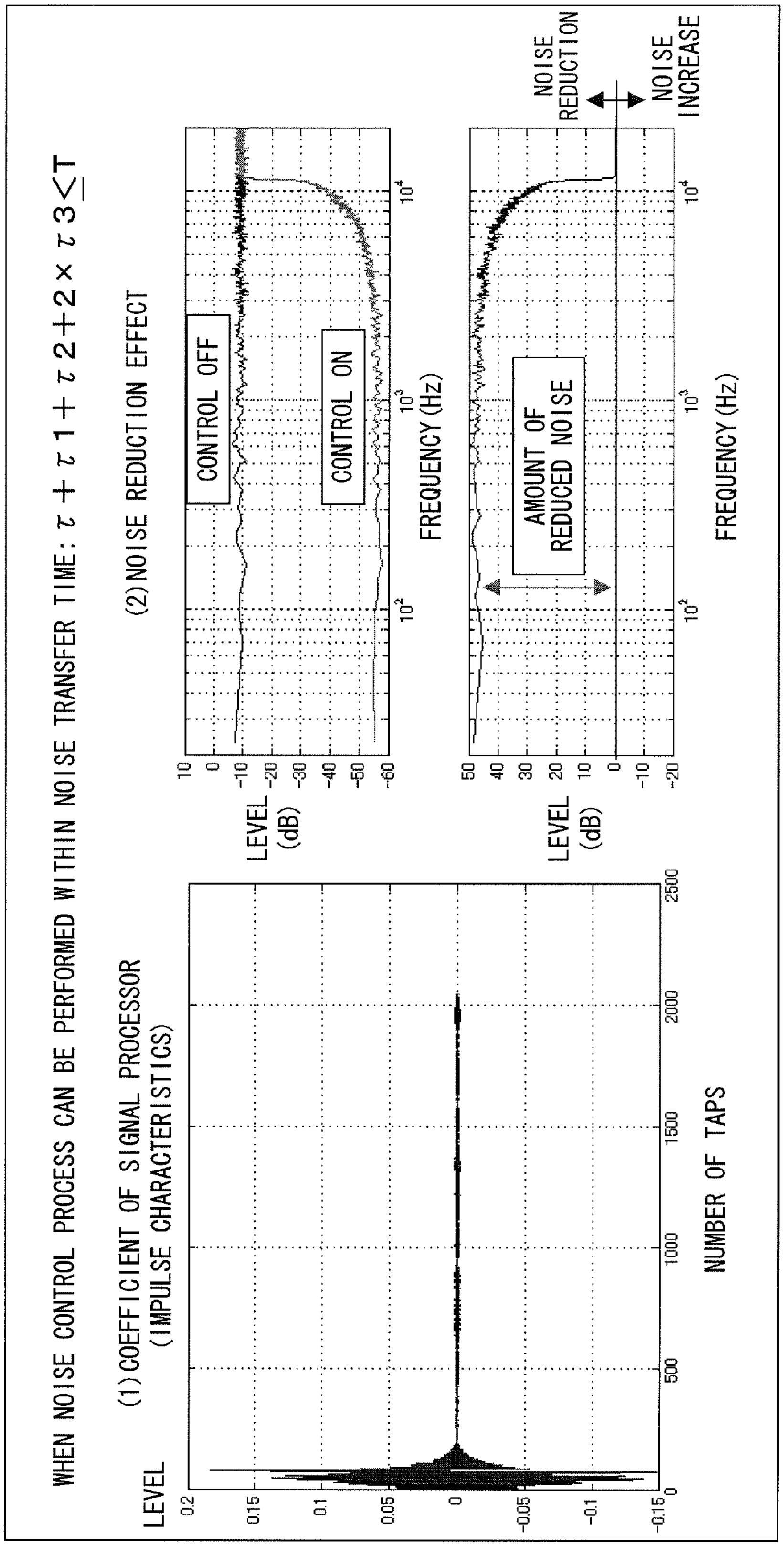
FIG. 51 PRIOR ART
FIG. 51 shows a coefficient of the signal processor 300 and a noise reduction effect at the control point 4, in a case where the noise control process in FIG. 48 can be performed within the noise transfer time.
Figure 52:
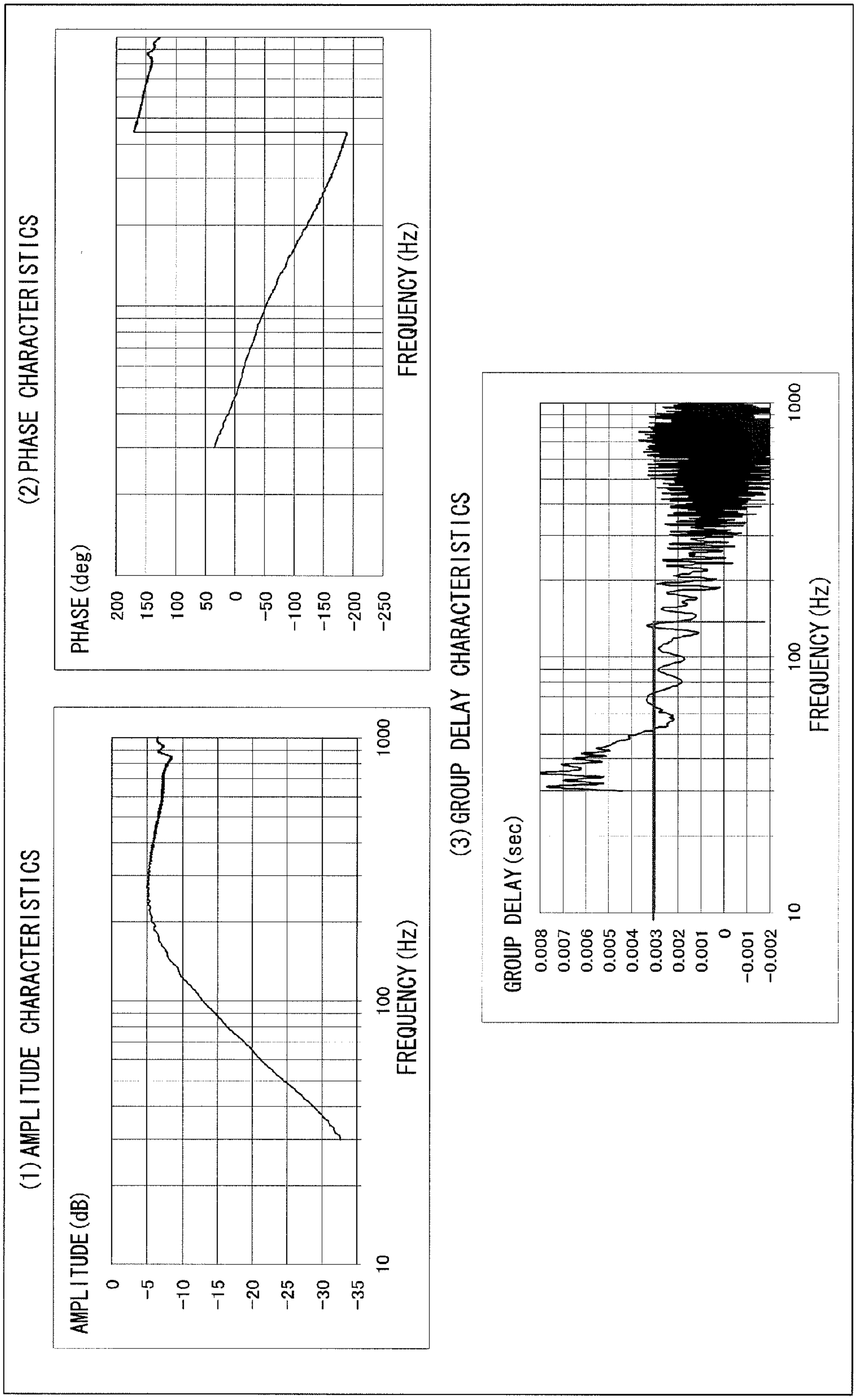
FIG. 52 PRIOR ART
FIG. 52 shows speaker characteristics.
Figure 53:
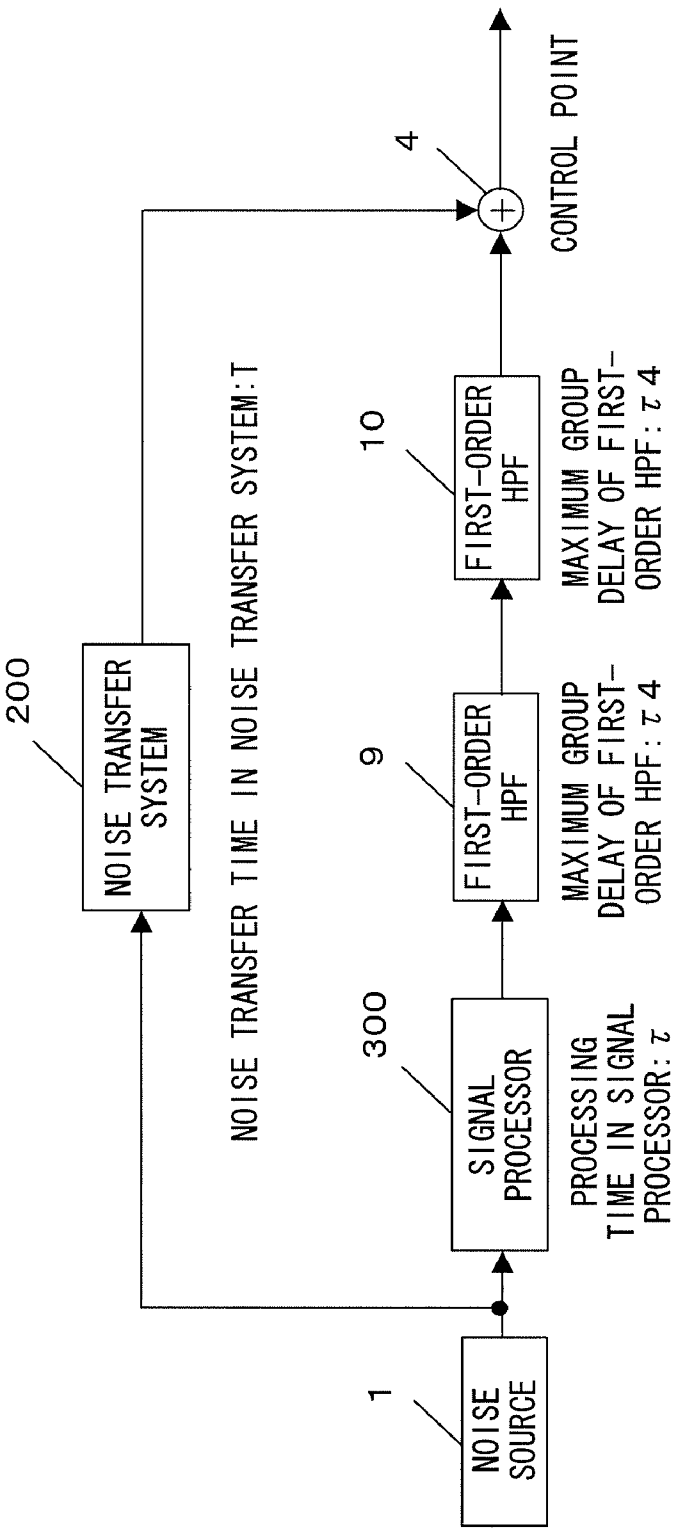
FIG. 53 PRIOR ART
FIG. 53 is a diagram showing HPFs being additionally inserted to an output of the signal processor 300 shown in FIG. 43.
Figure 54:
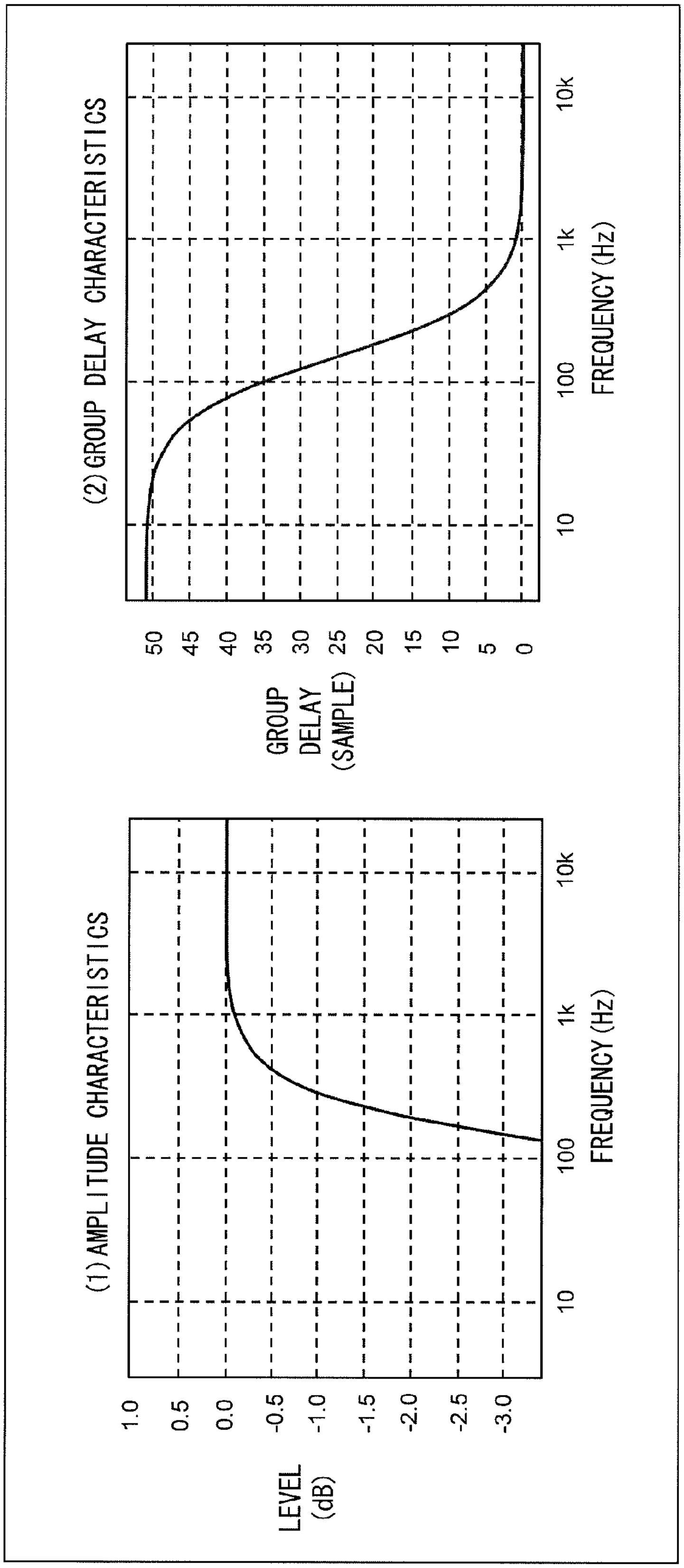
F I G. 5 4 PRIOR ART
FIG. 54 shows amplitude characteristics and group delay characteristics of first-order HPFs 9 and 10 shown in FIG. 53.
Figure 55:
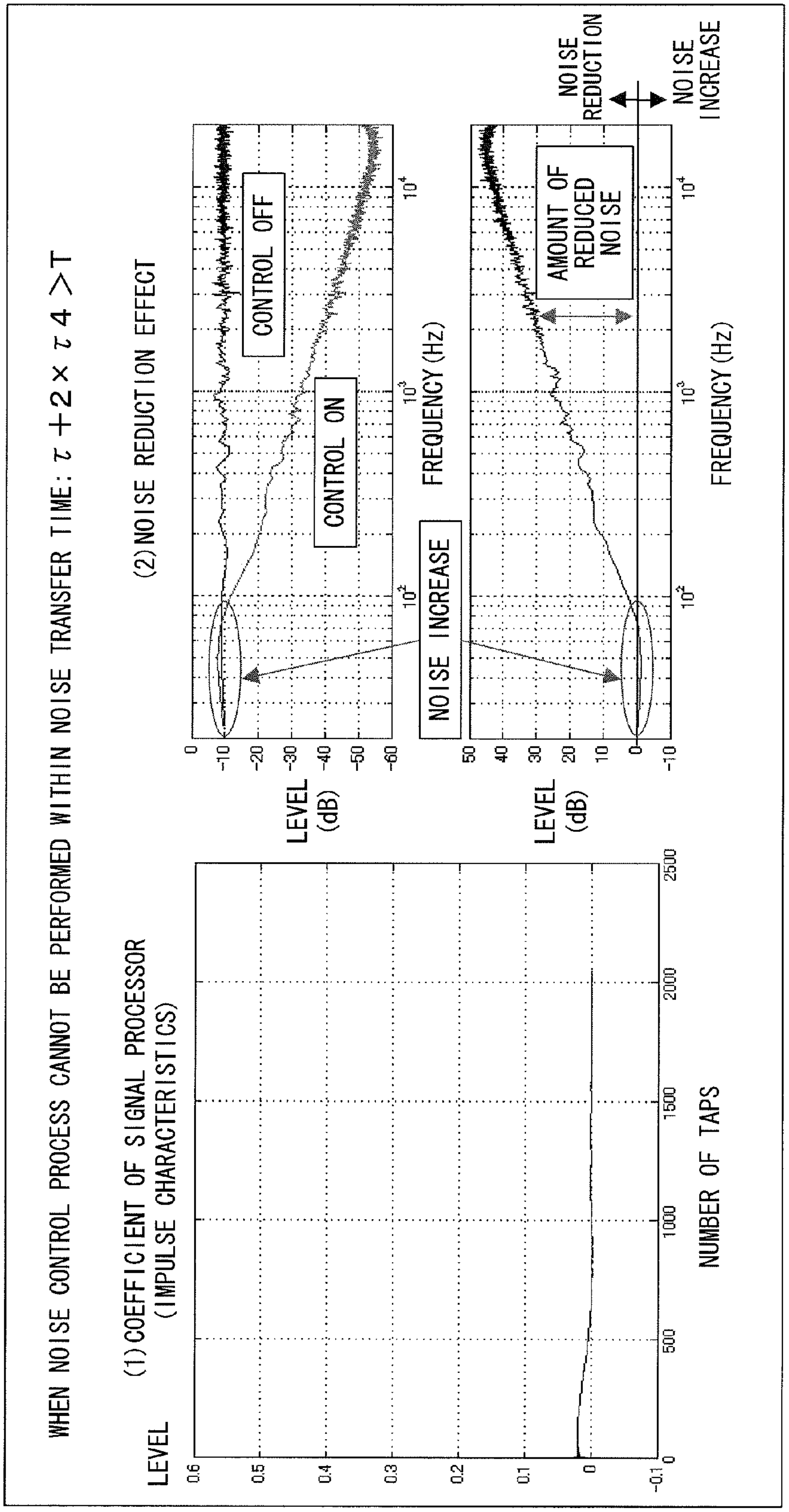
FIG. 55 PRIOR ART
FIG. 55 shows a coefficient of a signal processor 300 and a noise reduction effect at a control point 4, in a case where a noise control process in FIG. 53 cannot be performed within a noise transfer time.
Figure 56:
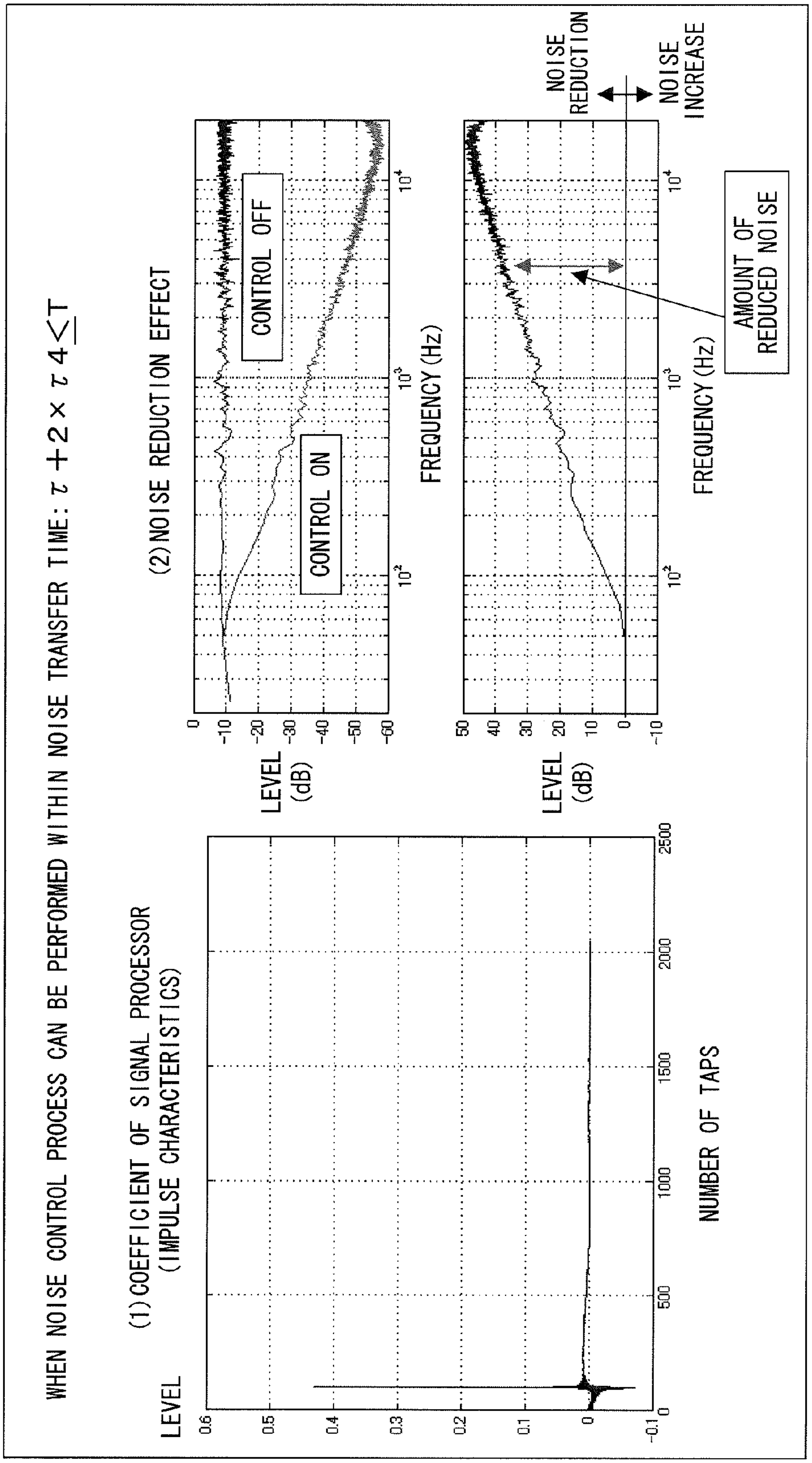
FIG. 56 PRIOR ART
FIG. 56 shows a coefficient of the signal processor 300 and a noise reduction effect at the control point 4, in a case where the noise control process in FIG. 53 can be performed within the noise transfer time.
Figure 57:
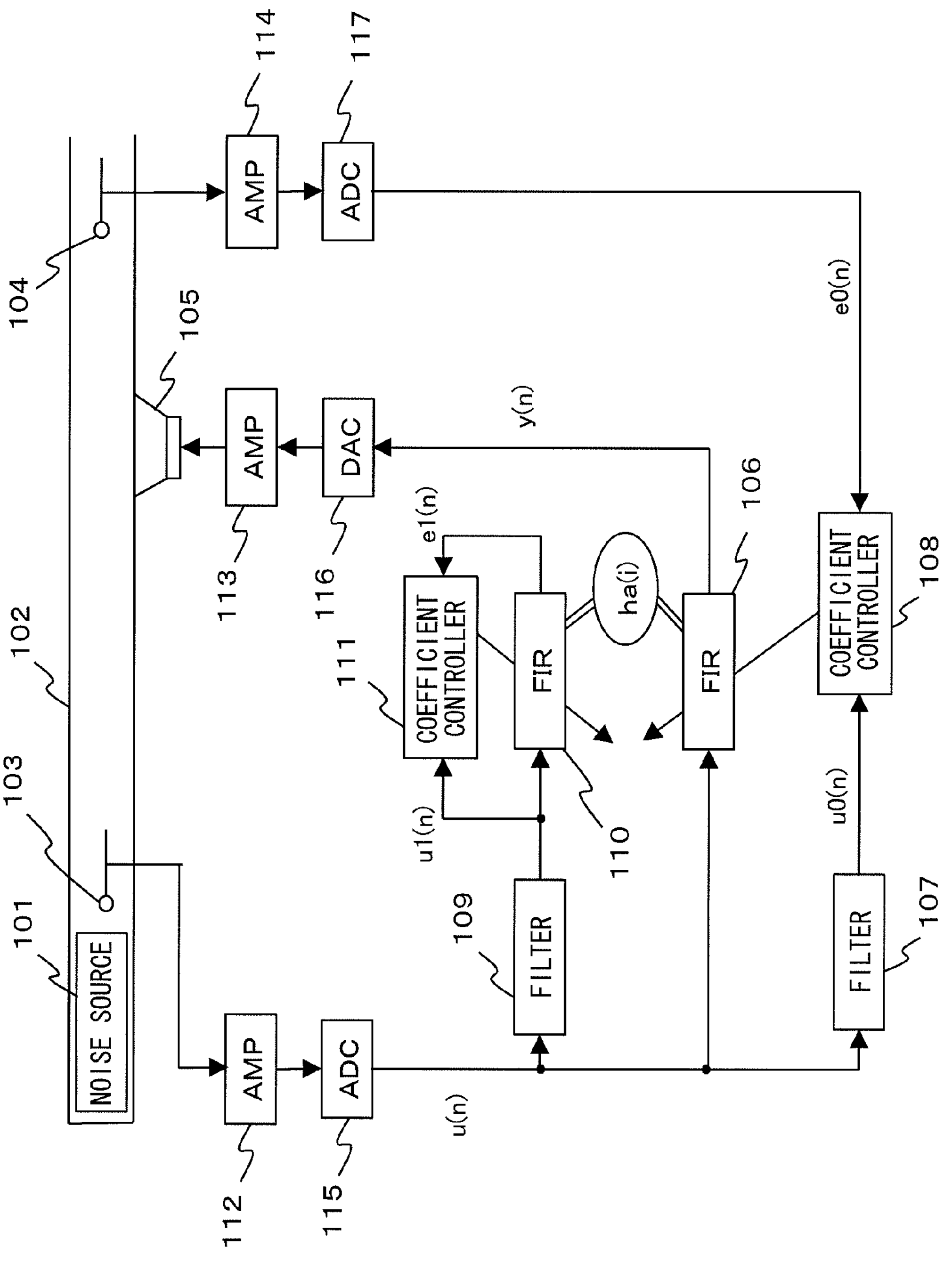
FIG. 57 PRIOR ART
FIG. 57 shows a conventional noise control device.

When the noise reduction effect shown in FIG. 39 is obtained in the noise control device shown in FIG. 38, the transfer characteristics for transfer from the point X to the point Y of the noise control device are as shown in FIG. 42. When the noise reduction effect shown in FIG. 36 is obtained in the noise control device shown in FIG. 31, the transfer characteristics for transfer from the point X to the point Y of the noise control device are as shown in FIG. 37. Obviously, the characteristics shown in FIG. 42 are characteristics that are substantially coincident with the characteristics shown in FIG. 7. On the other hand, in the characteristics shown in FIG. 37, both the amplitude characteristics and the phase characteristics show a minor error relative to the characteristics shown in FIG. 7. The error influences the noise reduction effect shown in FIG. 36.

In this manner, when, as shown in FIG. 38, the signal processor 300 of the noise control device is formed with the adaptive filter 301, and an adaptive process is performed so as to obtain a coefficient of the adaptive filter 301 with the output correction section 500 being operated, a highly accurate control coefficient can be obtained in a full frequency band. Accordingly, the noise control device shown in FIG. 38 can improve the noise reduction effect in a range including a low frequency range to a high frequency range. Needless to say, in the noise control device according to the third embodiment of the present invention, even when there is a frequency band for which the noise control process cannot be performed within the noise transfer time, a noise increase can be suppressed and further a noise can be reduced, in the same manner as in the noise control device according to the first embodiment of the present invention.

While the invention has been described in detail, the foregoing description is in all aspects illustrative and not restrictive. It is understood that numerous other modifications and variations can be devised without departing from the scope of the invention.

What is claimed is:

1. A noise control device that transmits a noise outputted from a noise source via a noise transfer system and synthesizes the transmitted noise and a control sound at a control point to thereby reduce the noise, the noise control device comprising:

a signal processor that detects the noise outputted from the noise source, and generates a control signal based on the noise;

a control acoustic system that generates the control sound for canceling the noise; and an output correction section that corrects the control signal outputted from the signal processor, in a frequency band for which a noise control process time τ, which is a time period from when the noise is outputted from the noise source to pass through the signal processor and the control acoustic system to when the control sound reaches the control point, is larger than a noise transfer time T, which is a time period from when the noise is outputted from the noise source to when the noise reaches the control point via the noise transfer system ($\tau > T$), wherein the control acoustic system generates the control sound based on the control signal outputted from the signal processor or the corrected control signal outputted from the output correction section, and the transmitted noise and the control sound generated by the control acoustic system are synthesized at the control point.

2. The noise control device according to claim 1, wherein the output correction section corrects the control signal outputted from the signal processor such that noise transfer characteristics of the noise that reaches the control point via the noise transfer system and noise control transfer characteristics of the control sound outputted from the control acoustic system have the same amplitude and opposite phases.

3. The noise control device according to claim 1, wherein the output correction section includes:

an adder to which the control signal outputted from the signal processor is inputted;

a filter circuit that extracts a signal in the frequency band from a signal outputted from the adder; and a gain adjuster that adjusts a level of the signal extracted by the filter circuit, wherein the adder: adds the signal of which the level is adjusted by the gain adjuster, to the control signal which is outputted from the signal processor and inputted to the adder; and outputs the corrected control signal to the control acoustic system.

4. The noise control device according to claim 3, wherein the adder, the filter circuit, and the gain adjuster form one feedback system, and the output correction section includes a plurality of the feedback systems, and the plurality of the feedback systems are connected in series.

5. The noise control device according to claim 1, wherein a signal obtained by synthesizing, at the control point, the noise that reaches the control point via the noise transfer system and the control sound outputted from the control acoustic system is inputted to the signal processor, as an error signal, and the signal processor:

detects the noise outputted from the noise source, and uses the detected noise as a reference signal; and generates the control signal based on the reference signal and the error signal, such that a level of the error signal is minimized.

6. The noise control device according to claim 1, wherein the control acoustic system includes a speaker that outputs the control sound, and the noise control device further comprises a microphone that is provided at the control point and picks up a sound obtained by synthesizing the transmitted noise and the control sound generated by the control acoustic system.

7. A noise control device that transmits a noise outputted from a noise source via a noise transfer system and synthesizes the transmitted noise and a control sound at a control point to thereby reduce the noise, the noise control device comprising:

an FIR (Finite Impulse Response) filter that detects the noise outputted from the noise source, and generates a control signal based on the noise; and a control acoustic system that generates the control sound for canceling the noise, wherein the FIR filter corrects the control signal such that noise transfer characteristics of the noise that reaches the control point via the noise transfer system and noise control transfer characteristics of the control sound outputted from the control acoustic system have the same amplitude and opposite phases, in a frequency band for which a noise control process time τ, which is a time period from when the noise is outputted from the noise source to pass through the FIR filter and the control acoustic system to when the control sound reaches the control point, is larger than a noise transfer time T, which is a time period from when the noise is outputted from the noise source to when the noise reaches the control point via the noise transfer system ($\tau > T$), the control acoustic system generates the control sound based on the control signal generated by the FIR filter or the corrected control signal corrected by the FIR filter, and the transmitted noise and the control sound generated by the control acoustic system are synthesized at the control point.

* * * * *